US011504334B2

(12) United States Patent
Perrin et al.

(10) Patent No.: US 11,504,334 B2
(45) Date of Patent: *Nov. 22, 2022

(54) SYNTHETIC PROGESTOGENS AND PHARMACEUTICAL COMPOSITIONS COMPRISING THE SAME

(71) Applicant: LABORATORIOS LEON FARMA SA, Leon (ES)

(72) Inventors: Philippe Perrin, Paris (FR); Jose Luis Velada, Amersfoort (NL); Dominique Drouin, Verrieres-le-Buisson (FR)

(73) Assignee: LABORATORIOS LEON FARMA SA, Leon (ES)

( * ) Notice: Subject to any disclaimer, the term of this patent is extended or adjusted under 35 U.S.C. 154(b) by 0 days.

This patent is subject to a terminal disclaimer.

(21) Appl. No.: 17/856,605

(22) Filed: Jul. 1, 2022

(65) Prior Publication Data
US 2022/0339107 A1 Oct. 27, 2022

Related U.S. Application Data

(63) Continuation of application No. 17/693,243, filed on Mar. 11, 2022, now Pat. No. 11,413,249, which is a continuation of application No. 17/684,261, filed on Mar. 1, 2022, now Pat. No. 11,351,122, which is a continuation of application No. 17/508,785, filed on Oct. 22, 2021, now Pat. No. 11,291,633, which is a continuation of application No. 17/346,139, filed on Jun. 11, 2021, now Pat. No. 11,291,632, which is a continuation of application No. 17/216,419, filed on Mar. 29, 2021, now Pat. No. 11,123,299, which is a continuation of application No. 17/105,300, filed on Nov. 25, 2020, now Pat. No. 10,987,364, which is a continuation of application No. 16/663,949, filed on Oct. 25, 2019, now abandoned, which is a continuation of application No. 13/171,410, filed on Jun. 28, 2011, now Pat. No. 10,849,857.

(60) Provisional application No. 61/368,396, filed on Jul. 28, 2010.

(51) Int. Cl.
A61K 31/585 (2006.01)
A61K 9/20 (2006.01)
A61K 9/28 (2006.01)
A61K 47/38 (2006.01)
A61K 47/10 (2017.01)
A61K 47/32 (2006.01)
A61K 45/06 (2006.01)
A61K 9/16 (2006.01)
A61K 31/567 (2006.01)
A61K 9/48 (2006.01)

(52) U.S. Cl.
CPC .......... A61K 9/2054 (2013.01); A61K 9/1688 (2013.01); A61K 9/2009 (2013.01); A61K 9/2013 (2013.01); A61K 9/2018 (2013.01); A61K 9/2806 (2013.01); A61K 31/567 (2013.01); A61K 31/585 (2013.01); A61K 45/06 (2013.01); A61K 47/10 (2013.01); A61K 47/32 (2013.01); A61K 47/38 (2013.01); A61K 9/2866 (2013.01); A61K 9/4816 (2013.01)

(58) Field of Classification Search
CPC .................................................... A61K 9/2054
USPC ....................................................... 514/170
See application file for complete search history.

(56) References Cited

U.S. PATENT DOCUMENTS

| | | |
|---|---|---|
| 4,129,564 A | 12/1978 | Wiechert et al. |
| 5,314,506 A | 5/1994 | Midler, Jr |
| 6,787,531 B1 | 9/2004 | Hilman et al. |
| 7,786,101 B2 | 8/2010 | Mayerofer |
| 9,603,860 B2 | 3/2017 | Penin et al. |
| 10,179,140 B2 | 1/2019 | Penin et al. |
| 10,603,281 B2 | 3/2020 | Perrin et al. |
| 10,849,857 B2 | 12/2020 | Penin et al. |
| 10,987,364 B1 | 4/2021 | Perrin et al. |
| 11,123,299 B2 | 9/2021 | Penin et al. |
| 11,291,632 B2 | 4/2022 | Perrin et al. |
| 11,291,633 B2 | 4/2022 | Perrin et al. |
| 11,351,122 B1 | 6/2022 | Perrin et al. |
| 2002/0132801 A1 | 9/2002 | Heil |
| 2004/0087563 A1 | 5/2004 | Mayerhofer |
| 2005/0096303 A1 | 5/2005 | Mayerhofer |
| 2005/0220825 A1 | 10/2005 | Funke et al. |
| 2006/0009428 A1 | 1/2006 | Grubb et al. |
| 2006/0275362 A1 | 12/2006 | Davila |
| 2006/0293295 A1 | 12/2006 | Strothmann et al. |
| 2011/0144071 A1 | 6/2011 | Grawe et al. |
| 2019/0269620 A1 | 9/2019 | Perrin et al. |
| 2020/0054566 A1 | 2/2020 | Penin et al. |
| 2021/0128586 A1 | 5/2021 | Penin et al. |
| 2022/0192991 A1 | 6/2022 | Perrin et al. |

FOREIGN PATENT DOCUMENTS

| | | |
|---|---|---|
| DE | 2652761 A1 | 5/1978 |
| DE | 3022337 A1 | 1/1982 |
| EC | SP077844 | 10/2007 |

(Continued)

OTHER PUBLICATIONS

"Micronor 0.35mg Tablets (Ortho) Jan. 2, 1973 Approval [Contraception]: Medical Officers Review; Chemistry," FOI Services, 37 pages, 1972.

(Continued)

Primary Examiner — Nizal S Chandrakumar
(74) Attorney, Agent, or Firm — Seed Intellectual Property Law Group LLP

(57) ABSTRACT

Described herein are synthetic progestogens, such as 6β,7β:15β,16β-Dimethylene-3-oxo-17α-pregn-4-ene-21,17-carbolactone, as well as pharmaceutical compositions comprising the same. Also described are methods of use.

30 Claims, 8 Drawing Sheets

(56) References Cited

FOREIGN PATENT DOCUMENTS

| | | |
|---|---|---|
| EP | 0551700 A1 | 7/1993 |
| EP | 1214076 B1 | 6/2002 |
| EP | 1611892 A2 | 1/2006 |
| EP | 1746101 A1 | 1/2007 |
| JP | 2010503632 A | 2/2010 |
| WO | 9806738 A1 | 2/1998 |
| WO | 0115701 A1 | 3/2001 |
| WO | 0152857 A1 | 7/2001 |
| WO | 2005087194 A1 | 9/2005 |
| WO | 2005087199 A2 | 9/2005 |
| WO | 2005105103 A2 | 11/2005 |
| WO | 2006015956 A1 | 2/2006 |
| WO | 2006061309 A1 | 6/2006 |
| WO | 2006128907 A2 | 12/2006 |
| WO | 2006138503 A2 | 12/2006 |
| WO | 2008003432 A1 | 1/2008 |
| WO | 2008031631 A2 | 3/2008 |
| WO | 2009036999 A1 | 3/2009 |
| WO | 2009100871 A2 | 8/2009 |
| WO | 2009138224 A1 | 11/2009 |
| WO | 2010015298 A2 | 2/2010 |
| WO | 2010015713 A1 | 2/2010 |
| WO | 2012000981 A1 | 1/2012 |

OTHER PUBLICATIONS

"Part 5: Pharmaceutical Manufacturing" & "Chapter 55: Pharmaceutical Necessities," Remington: The Science and Practice of Pharmacy, 21st Edition, ed. Beringer et al., p. 880 & 1059-1086, 2005. (7 pages).
"World Contraceptive Patterns 2013," United Nations, Department of Economic and Social Affairs, Population Division, 2 pages, 2013.
"YAZ® (drospirenone and ethinyl estradiol) Tablets," Bayer HealthCare Pharmaceuticals, p. 1-45, 2010.
Abdollahi et al., "Obesity: risk of venous thrombosis and the interaction coagulation factor levels and oral contraceptive use," Thromb. Haemost. 89(3):493-498, 2003.
Amy, "Contraception for women: an evidence based overview," BMJ 339:563-568, 2009. (10 pages).
Archer et al., "Drospirenone-only oral contraceptive: results from a multicenter noncomparative trial of efficacy, safety and tolerability," Contraception 92:439-444, 2015.
Arias, R.D. et al., Changes in bleeding patterns with depot medroxyprogesterone acetate subcutaneous injection 104 mg, Contraception 74:234-238, 2006.
Blanco-Molina et al., "Progestin-only contraception and venous thromboembolism," Thrombosis Research 129:e257-e262, 2012.
Blode et al., "A 1-year pharmacokinetic investigation of a novel oral contraceptive containing drospirenone in healthy female volunteers," The European Journal of Contraception and Reproductive Health Care 5:256-264, 2000.
Bühler, "Pharmaceutical Technology of BASF Excipients," BASF: the Chemical Company, 3rd revised edition, p. 1-166, 2008.
Casey et al., "Association of body mass index with removal of etonogestrel subdermal implant," Contraception 87:370-374, 2013.
Cedergren, "Maternal Morbid Obesity and the Risk of Adverse Pregnancy Outcome," Obstet. Gynecol. 103(2):219-224, 2004.
Centers for Disease Control and Prevention, "U.S. Medical Eligibility Criteria for Contraceptive Use," MMWR Early Release 59:1-86, 2010.
Connor et al., "Determining Risk Between Depo-Provera Use and Increased Uterine Bleeding in Obese and Overweight Women," J. Am. Board Fam. Pract. 15(1):7-10, 2002.
Corrigan et al., "Some Aspects of the Influence of Formulation on the Bioavailability of Drugs from Solid Dosage Forms," Irish Journal of Medical Science 143(1):197-207, 1974.
Curtis, K.M. et al., Progestogen-only contraceptive use in obese women. Contraception 2009;80(4):346-354.

Dhanjal, "Contraception in women with medical problems," Obstetric Medicine 1:78-87, 2008.
Dinger et al., "Oral contraceptive effectiveness according to body mass index, weight, age, and other factors," Am. J. Obstet. Gynecol. 263:e1-.e9, 2009.
Dragoman et al., "Contraceptive vaginal ring effectiveness is maintained during six weeks use: A prospective study of normal BMI and obese women," Contraception 87(4):432-436, 2013.
Fan et al., "Impact of polymers on dissolution performance of an amorphous gelleable drug from surface-coated beads," Eur. J. Pharm. Sci. 37(1):1-10, 2009. (abstract only).
Flegal et al., "Prevalence of Obesity and Trends in the Distribution of Body Mass Index Among US Adults, 1999-2010," Journal of the American Medical Association 307(5):491-97, 2012.
Fraser et al., "Depo-Provera use in an Australian metropolitan practice," Med. J. Australia 160(9):553-556, 1994.
Golightly et al., "Pharmaceutical excipients. Adverse effects associated with inactive ingredients in drug products (Part I).," Med. Toxicol. Adverse Drug Exp. 3(2):128-165, 1988.
Hampton et al., "Bleeding patterns with monophasic and triphasic low-dose ethinyl estradiol combined oral contraceptives," Contraception 77:415-419, 2008.
Harel et al., "Adolescents' Reasons for and Experience After Discontinuation of the Long-Acting Contraceptives Depo-Provera and Norplant," J. Adolesc. Health 19(2):118-123, 1996.
Hedaya, "8.3.1 Convention Oral Formulations" & "8.3.1.1 Solutions," Basic Pharmacokinetics, 2nd Edition, CRC Press Pharmacy Education Series, 2012. (3 pages).
Hill, "Gynecology Case Challenge: Vaginal Bleeding in a Woman Taking an Injectable Contraceptive," Medscape Women's Health 3(1), p. 1-9, 1998.
Imaizumi et al., "Stability and Several Physical Properties of Amorphous and Crystalline Forms of Indomethacin," Chem. Pharm. Bull. 28(9):2565-2569, 1980.
International Search Report and Written Opinion, dated Jan. 17, 2013, for International Application No. PCT/EP2011/060795, 6 pages.
Kaunitz, "Injectable Depot Medroxyprogesterone Acetate Contraception: An Update for U.S. Clinicians," Int. J. Fertil. 43(2):73-83, 1998.
Keder et al., "Compliance with depot medroxyprogesterone acetate: A randomized, controlled trial of intensive reminders," Am. J. Obstet. Gynecol. 179(3 Pt 1):583-585, 1998.
Kirk et al., "Analysis of androgenic steroid Girard P hydrazones using multistage tandem mass spectrometry," Rapid Communication in Mass Spectrometry 20:1247-1252, 2006.
Krattenmacher, "Drospirenone: pharmacology and pharmacokinetics of a unique progestogen," Contraception 62:29-38, 2000.
Lidegaard et al., "Risk of venous thromboembolism from use of oral contraceptives containing different progestogens and oestrogen doses: Danish cohort study," BMJ 343(d6423):1-15, 2011.
Mantha et al., "Assessing the risk of venous thromboembolic events in women taking progestin-only contraception: a meta-analysis," BMJ 345(e4944):1-10, 2012.
Murthy, "Obesity and Contraception: Emerging Issues," Semin. Reprod. Med. 28(2):156-163, 2010.
Niazi, Handbook of Pharmaceutical Manufacturing Formulations: Compressed Solid Products, Volume One, Second Edition, Informa Healthcare USA, Inc., New York, NY, p. 1-2738, 2009.
Nutley et al., "Treatment of bleeding problems associated with progestin-only contraceptives: survey results," Adv. Contracept. 13(4):419-28, 1997.
O'Neil et al., The Merck Index: An Encyclopedia of Chemicals, Drugs, and Biologicals,14th edition, Merck & Co., Inc., Whitehouse Station, NJ, USA, p. 585, 2006.
OECD/European Union, "Overweight and obesity among adults," Health at a Glance: Europe 2014, OECD Publishing, Paris, FR, p. 56-57, 2014.
Patel et al., "An overview of size reduction technologies in the field of pharmaceutical manufacturing," Asian Journal of Pharmaceutics, p. 216-220, 2008.

(56) References Cited

OTHER PUBLICATIONS

Pomp et al., "Risk of venous thrombosis: obesity and its joint effect with oral contraceptive use and prothrombotic mutations," Br. J. Haematol. 139:289-296, 2007.
Puthli et al., "Formulation and Performance Characterization of Radio-sterilized "Progestin-only" Microparticles Intended for Contraception," AAPS PharmSciTech 10(2):443-452, 2009.
Rosenbaum et al., "Inhibition of ovulation by a novel progestogen (drospirenone) alone or in combination with ethinylestradiol," The European Journal of Contraception and Reproductive Health Care 5:16-24, 2000.
Rosenberg et al., "Unintended Pregnancies and Use, Misuse and Discontinuation of Oral Contraceptives," J. Reprod. Med. 40(5);355-360, 1995.
Rosenberg, "Weight Change With Oral Contraceptive Use and During the Menstrual Cycle: Results of Daily Measurements," Contraception 58:345-349, 1998.
Rowe et al., Handbook of Pharmaceutical Excipients, Sixth Edition, Pharmaceutical Press, London, UK, p. 1-917, 2009.
Sansom, Aust Preset 1999;22:8 8-30 Aug. 1, 1999 (Year: 1999).
Sedgh et al., "Intended and Unintended Pregnancies Worldwide in 2012 and Recent Trends," Studies in Family Planning 45(3):301-314, 2014.
Shigetoh et al., "Higher Heart Rate May Predispose to Obesity and Diabetes Mellitus: 20-Year Prospective Study in a General Population," Am. J. Hypertension 22(2):151-155, 2009.
Sitruk-Ware, "New progestagens for contraceptive use," Human Reproduction Update 12(2):169-178, 2006.
Spence et al., "Increased Dissolution Rate and Bioavailability Through Comicronization with Microcrystalline Cellulose," Pharmaceutical Development and Technology 10:451-460, 2005.
World Health Organization, Medical eligibility criteria for contraceptive use: 4th edition, 2009, WHO Press, Geneva, Switzerland, 129 pages, 2010.
Zhang et al., "Effect of Diluents on Tablet Integrity and Controlled Drug Release," Drug Development and Industrial Pharmacy 26(7):761-765, 2000.

SYNTHETIC PROGESTOGENS AND PHARMACEUTICAL COMPOSITIONS COMPRISING THE SAME

FIELD OF THE INVENTION

The present invention relates to synthetic progestogens, such as 6β,7β:15β,16β-Dimethylene-3-oxo-17α-pregn-4-ene-21,17-carbolactone, as well as pharmaceutical compositions comprising the same, and methods of use.

BACKGROUND OF THE INVENTION

Several contraceptives which comprise synthetic progestogens and no oestrogen are commercially available. These contraceptives called "progestogen-only contraceptives" encompass implants, uterine delivery systems and pills.

Progestogen only contraceptives ("POC") have the advantage of avoiding the combined administration of estrogens as compared to traditional contraceptive combined pills. POCs, however, display several major drawbacks. Because of their low contraceptive reliability, POCs have to be taken each day at the same time without a pill-free or placebo interval.

The bleeding patterns for women who take POCs may be also be altered deeply as compared to the natural menstrual cycle, since amenorrhea or unscheduled bleeding or spotting may occur. Accordingly, POCs are poorly used and are usually indicated for women who cannot tolerate estrogen, for women in post-partum period and for women who are breast-feeding (Amy, Tripathi, 2009, BMJ, 339, 563-568; Mandisk, 2008, OBSTETRIC MEDICINE, 1, 78-87).

Drospirenone (CAS: 67392-87-4; 6β3,7β3:15β,16β-Dimethylene-3-oxo-17α-pregn-4-ene-21,17-carbolactone) is a synthetic progestogen with a pharmacological profile very closely related to that of natural progesterone. Drospirenone ("DRSP") is devoid of androgenic, glucocorticoid and anti-glucocorticoid activity but does possess potent antimineralocorticoid and antiandrogenic properties. It was shown that oral daily doses of at least 3 mg of drospirenone are able to inhibit ovulation over a single treatment cycle of 21 days. The combination of 3 mg drospirenone/30 µg ethinylestradiol provides a reasonable contraceptive safety margin by inhibiting ovulation with a low frequency of follicular maturation (Rosenbaum et al., 2000, THE EUROPEAN JOURNAL OF CONTRACEPTION AND REPRODUCTIVE HEALTH CARE, 5, 16-24).

Drospirenone (DRSP) is thus an appropriate progestin ingredient which may avoid the side-effects occurring with conventional synthetic progestogens such as weight gain and breast tension when combined with an estrogen for use as a contraceptive. DRSP is also likely to minimize fluid retention and to have neutral effects on metabolic and vascular risks (Blode et al., 2000, THE EUROPEAN JOURNAL OF CONTRACEPTION AND REPRODUCTIVE HEALTH CARE, 5, 256-264; Sitruk-Ware, 2006, HUMAN REPRODUCTION UPDATE, 12, 169-178). It has been also reported that drospirenone may treat moderate acne because of its well-established anti-androgenic properties.

Drospirenone as a contraceptive ingredient is available only in oral combined pills such as those marketed under the name of Yasmin® (3 mg DRSP/30 µg ethinylestradiol), Yaz® (3 mg DRSP/20 µg ethinylestradiol) and Yasminelle® (3 mg DRSP/20 µg ethinylestradiol). These pills comprise ethinylestradiol which acts to increase the ovulation inhibitory effect of drospirenone and to ensure contraception and cycle stability. The patent application WO2008031631 describes combined oral contraceptives in which drospirenone is used as a progestative agent and ethinylestradiol is replaced by the phytoestrogen 8-prenylnaringenin. These contraceptives may be included in modified release formulations of 8-prenylnaringenin and drospirenone which may continuously distribute the active ingredients for the gastro-intestinal transit time of generally 12 h-16 h.

The commercially available contraceptives Yasmin®, Yaz® and Yasminelle® comprise drospirenone in a micronized form which promotes its rapid dissolution in vitro and ensures its good oral bioavailability. It is also the case for Angeliq® which is a hormone replacement medicament combining drospirenone and estradiol. However, such formulations are characterized by a high plasma concentration peak for drospirenone after oral intake. High plasma concentrations are not preferred in patients treated with drospirenone because of a correlation between high $C_{max}$ and certain undesirable side effects as well as poor general tolerance when hormonal levels fluctuate too much each and every day.

Accordingly, there is still a need in the art for novel contraceptive kits and for novel pharmaceutical compositions comprising drospirenone.

SUMMARY OF THE INVENTION

The present invention provides pharmaceutical compositions and kits comprising pharmaceutical compositions, and methods for administering pharmaceutical compositions for preventing pregnancy in a patient. The pharmaceutical compositions may comprise active drugs such as active contraceptive drugs. Specifically, the active drugs may comprise progestogen-only contraceptives ("POC") for inhibiting ovulation. In specific embodiments, the pharmaceutical compositions and kits and methods of administering the pharmaceutical compositions allow for novel dosing regimens of POCs and provide pharmacokinetic profiles that reflect these novel dosing regimens.

In one embodiment, the pharmaceutical composition of the present invention may comprise an active contraceptive drug, wherein the pharmaceutical composition allows for a 28 day daily dosing regimen, and wherein after initial administration of the active contraceptive drug has established its contraceptive effect in a patient, the patient may skip up to 4 doses within any 28 day daily dosing regimen period. In a specific embodiment, the skipped up to 4 doses may be on non-consecutive days. In another specific embodiment, the skipped up to 4 doses may be on consecutive days. In another embodiment of the present invention, the pharmaceutical composition may further allow during the 28 day daily dosing regimen for the patient to skip up to two non-consecutive days of the active contraceptive drug, provided the active contraceptive drug skipped dose is taken within about 24 hrs after the up to two skipped non-consecutive days. In another embodiment, the active contraceptive drug may inhibit ovulation. In another embodiment, the contraceptive effect may comprise inhibiting ovulation.

In another specific embodiment, the active contraceptive drug may be a progestogen-only contraceptive (POC). In another specific embodiment, the POCs may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In a specific embodiment, the POC may be drospirenone. In another specific embodiment, each daily dose of drospirenone may comprise a dosage amount of at least about 2 mg.

In another specific embodiment, the pharmaceutical compositions may also have a particular pharmacokinetic profile. In one embodiment, the present invention may be a pharmaceutical composition wherein each daily dose of the active contraceptive drug, when orally administered to a patient in fasting conditions, provides a pharmacokinetic profile for the active contraceptive drug having:

i) a $T_{max}$ ranging from about 2.2 hrs to 6 hrs; and
ii) a mean $C_{max}$ which is less than about 30 ng/ml.

In a specific embodiment, the pharmacokinetic profile for the active contraceptive drug may additionally comprise an $AUC_{0\ h\text{-}tlast}$ which is at least 300 ng·h/ml. In another specific embodiment, the $AUC_{0\ h\text{-}tlast}$ may be at least 350 ng·h/ml. In another specific embodiment, the mean $C_{max}$ may range from about 15 ng/ml to about 30 ng/ml. In another specific embodiment, the active contraceptive drug with the above pharmacokinetic parameters may be a POC. In another specific embodiment, the POC may be drospirenone. In another embodiment, drospirenone may be the only administered active contraceptive drug.

In another specific embodiment, a kit may comprise the pharmaceutical compositions described above. In a specific embodiment, the kit may comprise one or more packaging units wherein each packaging unit comprises up to 28 daily active dosage units comprising an active contraceptive drug in a pharmaceutical composition, wherein the pharmaceutical composition allows for a 28 day daily dosing regimen, and wherein after initial administration of the active drug has established its contraceptive effect in a patient, the patient may skip up to 4 doses within any 28 day daily dosing regimen period. In a specific embodiment, the skipped up to 4 doses may be on non-consecutive days. In another specific embodiment, the skipped up to 4 doses may be on consecutive days. In another embodiment of the present invention, the kits may provide pharmaceutical compositions that further allow during the 28 day daily dosing regimen for the patient to skip up to two non-consecutive days of the active contraceptive drug, provided the active contraceptive drug skipped dose is taken within about 24 hrs after the up to two skipped non-consecutive days. In another embodiment, the active contraceptive drug may inhibit ovulation. In another embodiment, the contraceptive effect may comprise inhibiting ovulation.

The present invention also includes methods of administering the pharmaceutical compositions described above. In one embodiment, the methods of the present invention may comprise administering a composition comprising an active contraceptive drug, wherein the pharmaceutical composition allows for a 28 day daily dosing regimen, and wherein after initial administration of the active contraceptive drug has established its contraceptive effect in a patient, the patient may skip up to 4 doses within any 28 day daily dosing regimen period. In a specific embodiment, the skipped up to 4 doses may be on non-consecutive days. In another specific embodiment, the skipped up to 4 doses may be on consecutive days. In another embodiment of the present invention, the methods may comprise administering pharmaceutical compositions which further allows during the 28 day daily dosing regimen for the patient to skip up to two non-consecutive days of the active contraceptive drug, provided the active contraceptive drug skipped dose is taken within about 24 hrs after the up to two skipped non-consecutive days. In another specific embodiment, the kits may comprise pharmaceutical compositions comprising an active contraceptive drug with the above-described pharmacokinetic parameters. In another specific embodiment, the active contraceptive drug may be a progestogen-only contraceptive (POC). In another specific embodiment, the POC may be drospirenone. In another embodiment, drospirenone may be the only administered active contraceptive drug.

In another embodiment of the present invention, the patient may have a higher risk for developing a complication from the administration of an estrogen than the general population. In a specific embodiment, the complication from the administration of an estrogen may be due to the patient having one or more conditions or characteristics selected from the group consisting of a higher risk for developing thromboembolism than the general population, acquired or genetic thrombophilia or hypercoagulability, an age of 35 years or over who smoke cigarettes, a higher risk for stroke than the general population, sickle-cell disease or sickle-cell anemia, a higher risk than the general population for myocardial infarction, and women currently lactating.

In another embodiment of the present invention, the patient may be a woman and have one or more conditions or characteristics selected from the group consisting of being predisposed to hyperkalemia, suffering from kidney, liver or adrenal diseases, and being on daily, long-term treatment for a chronic condition with medications predisposed to hyperkalemia. In a specific embodiment, the medications predisposed to hyperkalemia may be selected from one or more of the group consisting of a non steroidal anti-inflammatory, potassium-sparing diuretics, potassium supplementation medication, angiotensin-converting enzyme (ACE) inhibitors, angiotensin-II receptor antagonists and heparin. In another specific embodiment, the patient may be in need to improve tolerance for s drospirenone. In another specific embodiment, the patient may be preparing for Hormone Replacement Therapy medicaments.

In another embodiment, the methods of the present invention may comprise producing a pharmacokinetic profile of an active drug in a patient, wherein the pharmacokinetic profile comprises a mean $T_{max}$ ranging from about 2.2 hrs to about 6 hrs, and a mean $C_{max}$ which is less than about 30 ng/ml, wherein the pharmacokinetic profile is measured in said patient after orally administering a single daily dosage unit of said active drug to said patient in fasting conditions. In another specific embodiment, the pharmacokinetic profile may additionally comprise an $AUC_{0\ h\text{-}tlast}$ which is at least about 300 ng·h/ml. In another specific embodiment, the $AUC_{0\ h\text{-}tlast}$ may be at least about 350 ng·h/ml. In another specific embodiment, the active drug may be an active contraceptive drug. In another embodiment, the active contraceptive drug may inhibit ovulation. In another specific embodiment, the active contraceptive drug may be a POC. In another specific embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In another specific embodiment, the POC may be drospirenone. In another specific embodiment, drospirenone may be the only administered active drug that inhibits ovulation.

In another embodiment of the present invention, the methods may include administering to a patient the compositions provided above. In another embodiment, the patient may be a woman and have one or more conditions or characteristics selected from the group consisting of being predisposed to hyperkalemia, suffering from kidney, liver or adrenal diseases, and being on daily, long-term treatment for a chronic condition with medications predisposed to hyperkalemia. In a specific embodiment, the medications predisposed to hyperkalemia may be selected from one or more of the group consisting of a non steroidal anti-inflammatory, potassium-sparing diuretics, potassium supplementation medication, angiotensin-converting enzyme (ACE) inhibitors, angiotensin-II receptor antagonists and heparin. In another specific embodiment, the patient may be in need to improve tolerance for s drospirenone. In another specific embodiment, the patient may be preparing for Hormone Replacement Therapy medicaments.

In another embodiment of the present invention, the pharmaceutical compositions may include active drugs that produce certain pharmacokinetic profiles. In a specific embodiment, the pharmaceutical composition may comprise an active drug, wherein a single daily dosage unit of the composition, when orally administered to a patient in fasting conditions provides a pharmacokinetic profile for the active drug having:
 i) a $T_{max}$ ranging from about 2.2 hrs to 6 hrs; and
 ii) a mean $C_{max}$, which is less than about 30 ng/m.

In another specific embodiment, the pharmacokinetic profile may also include an $AUC_{0\ h\text{-}tlast}$ which is at least 300 ng·h/ml. In another specific embodiment, the $AUC_{0\ h\text{-}tlast}$ may be at least 350 ng·h/ml. In another specific embodiment, the active drug may be an active contraceptive drug. In another embodiment, the active contraceptive drug may inhibit ovulation. In another specific embodiment, the active contraceptive drug may be a POC. In another embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In another embodiment, the POC may be drospirenone. In another specific embodiment of the present invention, each daily dosage unit may comprise a dosage amount of at least about 2 mg.

In another embodiment, the patient may be a woman and have one or more conditions or characteristics selected from the group consisting of being predisposed to hyperkalemia, suffering from kidney, liver or adrenal diseases, and being on daily, long-term treatment for a chronic condition with medications predisposed to hyperkalemia. In a specific embodiment, the medications predisposed to hyperkalemia may be selected from one or more of the group consisting of a non steroidal anti-inflammatory, potassium-sparing diuretics, potassium supplementation medication, angiotensin-converting enzyme (ACE) inhibitors, angiotensin-II receptor antagonists and heparin. In another specific embodiment, the patient may be in need to improve tolerance for s drospirenone. In another specific embodiment, the patient may be preparing for Hormone Replacement Therapy medicaments.

In another embodiment of the present invention, the pharmaceutical compositions may comprise active drugs characterized by dissolution tests. In a specific embodiment, a pharmaceutical composition may comprise an active drug, wherein:
 (a) a daily active oral dosage unit of the composition comprises an amount of said active drug of at least 2 mg, and
 (b) the daily active oral dosage unit comprises the active drug in a form such that when subjected to an in vitro dissolution test according to the USP XXIII Paddle Method:
  (i) no more than 50% of the active drug initially present in the daily active dosage unit is dissolved within 30 minutes, and
  (ii) at least 50% of the active drug is dissolved in a time range from 3 hours to 4 hours.

In another specific embodiment, the active drug may be an active contraceptive drug. In another embodiment, the active contraceptive drug may inhibit ovulation. In another specific embodiment, the active contraceptive drug may be a POC. In another embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In another embodiment, the POC may be drospirenone. In another embodiment, each daily dosage unit of drospirenone may comprise a dosage amount of at least about 2.0 mg to about 6.0 mg. In a specific embodiment, the each daily dosage unit of drospirenone may comprise a dosage amount of at least about 3.0 mg to about 4.5 mg.

The present invention may also include kits that comprise one or more packaging units wherein each packaging unit comprises dosage units with an active drug that provides certain pharmacokinetic parameters. In a specific embodiment, the kit may comprise one or more packaging units wherein each packaging unit comprises 21 to 28 daily active dosage units comprising an active drug and wherein a single active dosage unit, when orally administered under fasting conditions, is adapted to provide a pharmacokinetic profile for the active drug consisting of one or more of the pharmacokinetic parameters selected from the group consisting of:
 i) a $T_{max}$ ranging from about 2.2 hrs to 6 hrs; and
 ii) a mean $C_{max}$ which is less than about 30 ng/ml.

In another specific embodiment, the pharmacokinetic profile may also comprise an $AUC_{0\ h\text{-}tlast}$ which is at least 300 ng·h/ml. In another specific embodiment, the AUC$_{0\ h\text{-}tlast}$ may be at least 350 ng·h/ml. In another embodiment, the mean C$_{max}$ may range from about 15 ng/ml to about 30 ng/ml. In another specific embodiment, the active drug may be an active contraceptive drug. In another embodiment, the active contraceptive drug may inhibit ovulation. In another specific embodiment, the active contraceptive drug may be a POC In another embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In another embodiment, the POC may be drospirenone.

In another embodiment, the patient may be a woman and have one or more conditions or characteristics selected from the group consisting of being predisposed to hyperkalemia, suffering from kidney, liver or adrenal diseases, and being on daily, long-term treatment for a chronic condition with medications predisposed to hyperkalemia. In a specific embodiment, the medications predisposed to hyperkalemia may be selected from one or more of the group consisting of a non steroidal anti-inflammatory, potassium-sparing diuretics, potassium supplementation medication, angiotensin-converting enzyme (ACE) inhibitors, angiotensin-II receptor antagonists and heparin. In another specific embodiment, the patient may be in need to improve tolerance for s drospirenone. In another specific embodiment, the patient may be preparing for Hormone Replacement Therapy medicaments. In another specific embodiment, each daily dosage unit of drospirenone may comprise a dosage amount of at least about 2 mg. In another specific embodiment, the amount of drospirenone in each daily active unit dosage may range from about 2.0 mg to about 6.0 mg. In another specific embodiment, the amount of drospirenone in each daily active unit dosage may range from about 3.0 mg to about 4.5 mg.

The kits of the present invention may also include contraceptive kits comprising one or more packaging units that comprise dissolution tests of an active drug, such as drospirenone. In a specific embodiment, the contraceptive kit may comprise one or more packaging units wherein each packaging unit comprises 21 to 28 daily active dosage units and wherein
  (a) the amount of drospirenone in each daily active dosage unit is at least 2 mg without estrogen, and
  (b) each daily active dosage unit comprises drospirenone in a form such that when subjected to an in vitro dissolution test according to the USP XXIII Paddle Method:
    (i) no more than 50% of the drospirenone initially present in the said daily active dosage unit is dissolved within 30 minutes and (ii) at least 50% of the said drospirenone is dissolved in a time range from 3 hours to 4 hours.

In a specific embodiment, drospirenone may be the sole contraceptive ingredient. In another specific embodiment, the amount of drospirenone in each daily active unit dosage may range from about 2.0 mg to about 6.0 mg. In another specific embodiment, the amount of drospirenone in each daily active unit dosage may range from about 3.0 mg to about 4.5 mg.

One embodiment of the present invention may include pharmaceutical compositions comprising progestogen-only contraceptive (POC) defined by a d50 particle size. In a specific embodiment, the POC may have a d50 particle size which ranges from about 10 μm to about 60 μm. In a specific embodiment, the d50 particle size may range from about 10 μm to about 30 μm. In another specific embodiment, the surface area of the particles may be from about 2000 cm$^2$/g to about 8500 cm$^2$/g. In another specific embodiment, the surface area of the particles may be from one or more selected from the group consisting of about 2000 cm$^2$/g, about 2500 cm$^2$/g, about 3000 cm$^2$/g, about 3500 cm$^2$/g, about 4000 cm$^2$/g, about 4500 cm$^2$/g, about 5000 cm$^2$/g, about 5500 cm$^2$/g, about 6000 cm$^2$/g, about 6100 cm$^2$/g, about 6200 cm$^2$/g, about 6300 cm$^2$/g, about 6400 cm$^2$/g, about 6500 cm$^2$/g, about 6600 cm$^2$/g, about 6700 cm$^2$/g, about 6800 cm$^2$/g, about 6900 cm$^2$/g, about 7000 cm$^2$/g, about 7500 cm$^2$/g, about 8000 cm$^2$/g and about 8500 cm$^2$/g.

In another embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In another embodiment, the POC may be drospirenone. In another embodiment, the particles may have the pharmacokinetic profiles as characterized above.

One embodiment of the present invention may also include methods comprising sizing drsopirenone to a particular d50 particle size. In a specific embodiment, the methods may comprise sizing drospirenone to a d50 particle size which ranges from about 10 μm to about 60 μm by subjecting drospirenone to one or mills selected from the group consisting of a ball mill, a hammer mill, a fluid energy mill, a rod mill, a cutting mill and an oscillating granulator. In a specific embodiment, the methods may further comprise the step of subjecting drospirenone to a vibrating sieve. In another embodiment, the methods may comprise sizing drospirenone to a d50 particle size which ranges from about 10 μm to about 60 μm by:
  (i) dissolving drospirenone in a water-miscible solvent; and
  (ii) dispersing the resulting solution in cold water under stirring so that to induce the precipitation of drospirenone.

In another specific embodiment, the methods may further comprise the step of subjecting drospirenone to a vibrating sieve. In a specific embodiment of the present invention, the water-miscible solvent may be selected from one or more of the group consisting of methanol, ethanol, isopropanol, dimethylformamide, tetrahydrofuran, dioxane or dimethyl sulfoxide, dimethylacetamide and acetone. In another specific embodiment, the water-miscible solvent may be dimethylacetamide.

In another embodiment of the present invention, the pharmaceutical compositions may comprise a progestogen-only contraceptive (POC), wherein the pharmaceutical composition allows for a 28 day daily dosing regimen, and wherein after initial administration of POC has inhibited ovulation in a patient, the patient may skip up to 4 doses within any 28 day daily dosing regimen period. In another embodiment, the pharmaceutical composition may further allow during the 28 day daily dosing regimen for the patient to skip up to two non-consecutive days of the POC, provided the POC skipped dose is taken within about 24 hrs after the up to two skipped non-consecutive days. In a specific embodiment, the skipped up to 4 doses may be on non-consecutive days. In another specific embodiment, the skipped up to 4 doses may be on consecutive days. In another embodiment, the POC may inhibit ovulation.

In another embodiment of the present invention, the pharmaceutical compositions may comprise drospirenone, wherein the pharmaceutical composition allows for a 28 day daily dosing regimen, and wherein after initial administration of drospirenone has inhibited ovulation in a patient, the patient may skip up to 4 doses within any 28 day daily dosing regimen period. In another embodiment, the pharmaceutical composition may further allow during the 28 day daily dosing regimen for the patient to skip up to two non-consecutive days of the drospirenone, provided the drospirenone skipped dose is taken within about 24 hrs after the up to two skipped non-consecutive days. In a specific embodiment, the skipped up to 4 doses may be on non-consecutive days. In another specific embodiment, the skipped up to 4 doses may be on consecutive days. In another embodiment, the drospirenone may inhibit ovulation.

In another embodiment of the present invention, the methods of the present invention may include administering compositions that comprise a progestogen-only contraceptive (POC), wherein the pharmaceutical composition allows for a 28 day daily dosing regimen, and wherein after initial administration of POC has inhibited ovulation in a patient, the patient may skip up to 4 doses within any 28 day daily dosing regimen period. In another embodiment, the pharmaceutical composition may further allow during the 28 day daily dosing regimen for the patient to skip up to two non-consecutive days of the POC, provided the POC skipped dose is taken within about 24 hrs after the up to two skipped non-consecutive days. In a specific embodiment, the skipped up to 4 doses may be on non-consecutive days. In another specific embodiment, the skipped up to 4 doses may be on consecutive days. In another embodiment, the POC may inhibit ovulation.

In another embodiment of the present invention, the methods of the present invention may include administering compositions that comprise drospirenone, wherein the pharmaceutical composition allows for a 28 day daily dosing regimen, and wherein after initial administration of drospirenone has inhibited ovulation in a patient, the patient may skip up to 4 doses within any 28 day daily dosing regimen period. In another embodiment, the pharmaceutical composition may further allow during the 28 day daily dosing regimen for the patient to skip up to two non-consecutive days of the drospirenone, provided the drospirenone skipped dose is taken within about 24 hrs after the up to two skipped non-consecutive days. In a specific embodiment, the skipped up to 4 doses may be on non-consecutive days. In another specific embodiment, the skipped up to 4 doses may be on consecutive days. In another embodiment, the drospirenone may inhibit ovulation.

In another embodiment of the present invention, the kits may comprise one or more packaging units wherein each packaging unit comprises up to 28 daily active dosage units comprising a progestogen-only contraceptive (POC) in a pharmaceutical composition, wherein the pharmaceutical composition allows for a 28 day daily dosing regimen, and wherein after initial administration of POC has inhibited ovulation in a patient, the patient may skip up to 4 doses within any 28 day daily dosing regimen period. In another embodiment, the pharmaceutical composition may further allow during the 28 day daily dosing regimen for the patient to skip up to two non-consecutive days of the POC, provided the POC skipped dose is taken within about 24 hrs after the up to two skipped non-consecutive days. In a specific embodiment, the skipped up to 4 doses may be on non-consecutive days. In another specific embodiment, the skipped up to 4 doses may be on consecutive days. In another embodiment, the POC may inhibit ovulation.

In another embodiment of the present invention, the kits may comprise one or more packaging units wherein each packaging unit comprises up to 28 daily active dosage units comprising drospirenone in a pharmaceutical composition, wherein the pharmaceutical composition allows for a 28 day daily dosing regimen, and wherein after initial administration of drospirenone has inhibited ovulation in a patient, the patient may skip up to 4 doses within any 28 day daily dosing regimen period. In another embodiment, the pharmaceutical composition may further allow during the 28 day daily dosing regimen for the patient to skip up to two non-consecutive days of the drospirenone, provided the drospirenone skipped dose is taken within about 24 hrs after the up to two skipped non-consecutive days. In a specific embodiment, the skipped up to 4 doses may be on non-consecutive days. In another specific embodiment, the skipped up to 4 doses may be on consecutive days. In another embodiment, the drospirenone may inhibit ovulation.

BRIEF DESCRIPTION OF THE FIGURES

FIG. 1 shows the cumulative distribution curve (cdf, filled diamonds) and the probability density function curve (pdf, filled squares) for drospirenone (DRSP) batch 080053. The distribution experimental data were obtained by laser diffraction method. X-coordinate: particle size (µm) in log scale. Left Y-coordinate: cumulative distribution in percentage. Right Y-coordinate: probability density function.
FIG. 2 shows the in vitro dissolution profiles for tablet (A-3 mg) obtained from DRSP batch 080053 as described in Example 1 (inventive, curve no 2) and comparative tablets, namely Yasminelle® (curve no 4), tablets CO1-3 mg (curve no 3) and tablets CO2-3 mg (curve no 1). Each tablet comprises 3 mg of DRSP. The in vitro dissolution profiles were determined by the USP XXIII Paddle Method as described in Example 2. X-coordinate: time in hours, Y-coordinate: mean dissolution percentage of DRSP relating to the initial amount of DRSP contained in the tested tablet.
FIG. 3a shows DRSP plasma mean concentration versus time curves obtained after the oral administration of a single tablet of reference product, i.e. Yasminelle® (empty squares) or after the oral administration of a single tablet obtained from DRSP batch 080053 as described in Example 1 (test product, filled squares). In both cases, the DRSP dosage was 3 mg. These clinical data were obtained during a monocentric, open, randomized, single-dose, two period crossover clinical trial conducted on 14 healthy female volunteers as described in Example 3 part 1. Each volunteer received randomly, an oral single dose of 1 tablet of the test product or one tablet of Yasminelle® on two single occasions, always under fasting conditions. Study periods were separated by a real wash-out phase of 7 days. In each study, blood samples were collected before the administration of the tablet (pre-dose, time 0) and at 0:30, 1:00, 1:30, 2:00, 3:00, 4:00, 5:00, 6:00, 8:00, 12:00, 24:00, 48:00 and 72:00 hours post dosing for assaying the DRSP plasma concentration. The X-coordinate: time after the oral administration of the tablet (in hours); and Y-coordinate: mean plasma concentration of DRSP in ng/ml (arithmetic mean).

FIG. 3b shows DRSP plasma mean concentration versus time curves obtained after the oral administration of a single tablet of reference product i.e. Yasminelle® (empty squares) or after the oral administration of a single tablet CO1-3 mg (filled diamonds) or after the oral administration of a single tablet CO2-3 mg (filled squares) under fasting conditions (see Example 3, part 2). The X-coordinate: time after the oral administration of the tablet (in hours); the Y-coordinate: mean plasma concentration of DRSP in ng/ml (arithmetic mean).

FIG. 4a and FIG. 4b show the experimental DRSP plasma mean concentration versus time curves: (i) for the oral administration of a single tablet of Yasminelle® (comparative, filled squares); and (ii) for the oral administration of a single tablet as described in Example 1 (A-3 mg, invention, empty triangles). Both Yasminelle® tablet and tablet A-3 mg contains 3 mg of DRSP. FIGS. 4a and 4b also show the predicted mean DRSP plasma concentration versus time curve (invention, empty diamonds) obtained for the oral administration of a tablet similar to that described in Example 1, but containing 4 mg of DRSP (tablet A-4 mg). Such a curve was extrapolated from the experimental pharmacokinetic data obtained in the clinical trial described in Example 3, part 1. The X-coordinate: time after the oral administration of the tablet (in hours); the Y-coordinate: mean plasma concentration of DRSP in ng/ml.

FIG. 4c shows the mean plasma DRSP concentration versus time curves resulting from the repeated administration of one tablet of Yasminelle® (curve no 1), that of one tablet A-3 mg (curve no 3), and that of one tablet A-4 mg (curve no 2), every 24 hours. These curves were obtained by extrapolation of experimental pharmacokinetic data obtained in the clinical trial described in Example 3. The X-coordinate: time after the oral administration of the first tablet (in hours); the Y-coordinate: mean plasma concentration of DRSP in ng/ml.

FIG. 5a shows the mean in vitro dissolution profile for tablets obtained from DRSP batch No PR100003 as described in Example 5 (see part 1). The tablet comprises 4 mg of DRSP. The X-coordinate: time in hours; the Y-coordinate: mean dissolution percentage of DRSP relating to the initial amount of DRSP contained in the tested tablet.

FIG. 5b shows DRSP plasma mean concentration versus time curves obtained after the oral administration of a single tablet of reference product, i.e. Yasminelle® (empty squares) or after the oral administration of a single tablet B-4 mg (filled squares) under fasting conditions (see Example 5, part 2). The X-coordinate: time after the oral administration of the tablet (in hours); the Y-coordinate: mean plasma concentration of DRSP in ng/ml.

FIGS. 6a and 6b show the results of a clinical trial aiming to illustrate the contraceptive efficiency of the contraceptive compositions according to the invention. The methodology of the clinical trial is described in Example 4. Briefly, the treatment period comprises two treatment cycles in which the subjects took one pill of 4 mg DRSP (tablet B-4 mg) from day 1 to day 24 and one placebo tablet from day 25 to day 28 of each treatment cycle at a fixed hour. On day 5 and day 13 of the second cycle, the pill intake was delayed for 24 hours (i.e. no pill was taken on day 5 and day 13 and that 2 pills were taken on day 6 and day 14, respectively). The complete study consisted of a 56-day treatment period and a 28-day post-treatment follow-up period. The pill corresponds to tablet B-4 mg.

FIG. 6a shows the variation of the individual plasma levels of progesterone during the treatment period and the follow-up period. The X-coordinate: time in days after the first pill intake; the Y-coordinate: progesterone level in ng/ml.

FIG. 6b shows the variation of the individual plasma levels of estradiol during the treatment period and the follow-up period. The X-coordinate: time in days after the first pill intake; the Y-coordinate: estradiol level in pg/ml.

DETAILED DESCRIPTION OF THE INVENTION

Figure 1:
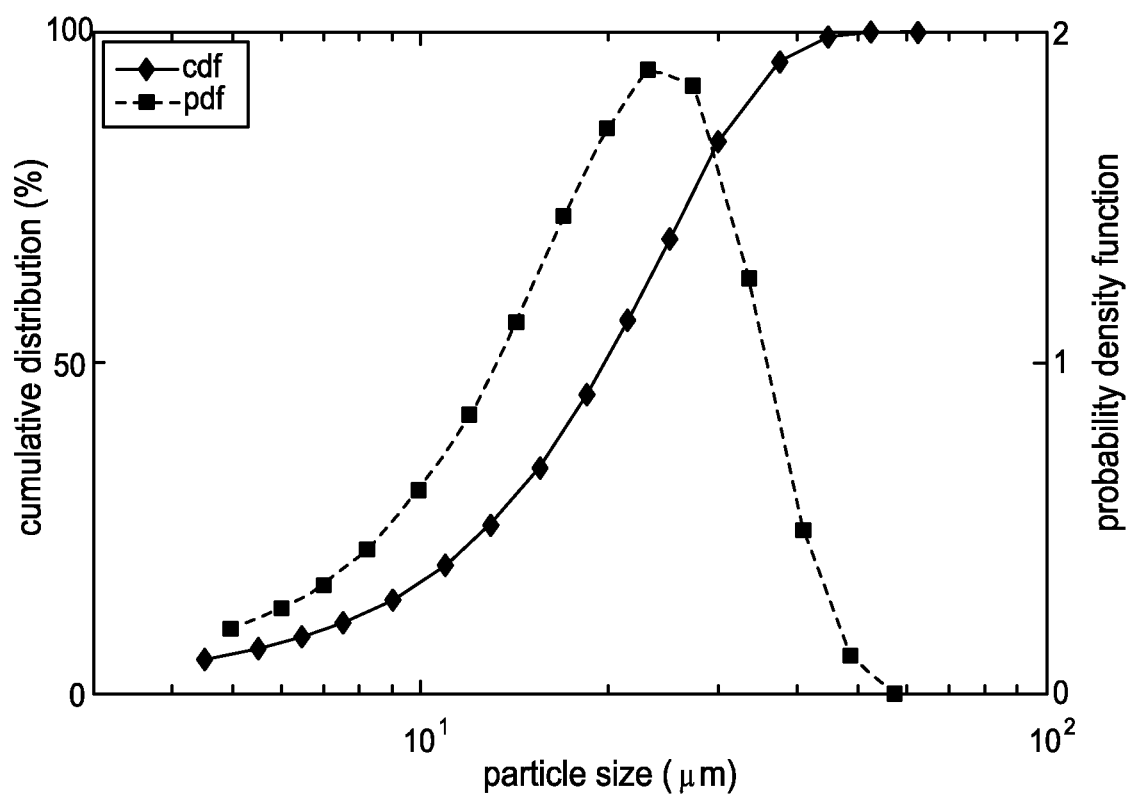
FIG. 1: Particle Size Distribution

The present invention relates to pharmaceutical compositions and contraceptive kits comprising a plurality of active daily dosage units. Each active daily dosage unit may include a pharmaceutical composition comprising an active drug. In a specific embodiment, each daily dosage unit may include a pharmaceutical composition comprising an active drug such as a progestogen-only contraceptive (POC). In another specific embodiment, each daily dosage unit may include a pharmaceutical composition comprising drospirenone. In preferred embodiments, the said pharmaceutical composition may include drospirenone, without estrogen. In other words, the contraceptive kit comprises a progestogen-only contraceptive kit. Drospirenone may be the sole contraceptive agent present within the pharmaceutical composition. The active daily dosage unit enables to prevent pregnancy when daily administered to a woman of child-bearing age over a period of 21 to 28 consecutive days. The number of active daily dosage units in the contraceptive kit may vary depending on the contraceptive method in which the contraceptive kit is intended to be used.

In order to disclose the contraceptive kit of the invention in a manner sufficiently clear and complete, the pharmaceutical composition of the active daily dosage units of the kit and the contraceptive method for which the kit is dedicated are fully-described in Sections 1 and 2, respectively, hereunder. In Section 3, specific embodiments of the contraceptive kit of the invention are also described.

1. Pharmaceutical Compositions

The commercially available drospirenone-containing contraceptive pills comprise both ethinyl-estradiol and micronized drospirenone. According to European patent EP1214076B1, the micronized form of drospirenone promotes its rapid dissolution in vitro. This rapid dissolution in vitro is claimed to be a necessary condition for obtaining a good bioavailability via the oral route. The rapid dissolution rate of drospirenone in vitro is assessed to be correlated to a rapid absorption in vivo of DRSP which avoids its degradation by gastric or intestine environments. Several other patents and patent applications, such as WO2006128907, or WO2009138224, describe drospirenone compositions which exhibit a rapid dissolution of drospirenone in vitro.

Accordingly, the international application WO2006128907 teaches that surfactants may enhance the dissolution rate of non-micronized drospirenone having a specific surface area lower than 10 000 cm$^2$/g. The international application WO2009138224 provides that the dissolution rate of drospirenone may be significantly improved by co-milling drospirenone with an appropriate carrier so as to obtain drospirenone in an amorphous state.

As mentioned in EP1214076B1, a rapid dissolution of drospirenone in vitro generally means that at least 70% of the drospirenone is dissolved within 30 minutes when the composition is subjected to an in vitro dissolution assay such as USP XXIII Paddle Method II.

Surprisingly, in view of these data, the present invention showed, through in vivo pharmacokinetic assays, that a rapid dissolution of drospirenone in vitro is not required for obtaining a good oral bioavailability. In this respect, the present invention provides a drospirenone-containing composition with a slow dissolution rate of drospirenone in vitro and which exhibits a similar mean AUC value (Area Under the Curve) as compared to Yasminelle® when orally administered to female patients.

Moreover, the present invention relates to DRSP-containing compositions which also display a significantly mean reduced $C_{max}$ value (Maximum Plasma Concentration) associated with a delayed mean $t_{max}$ value for drospirenone as compared to Yasminelle®. The decrease of DRSP $C_{max}$ improves the tolerance of the DRSP-containing composition by reducing or avoiding side-effects, in particular those related to the plasma level of potassium.

Drospirenone has an anti-mineralocorticoid property which leads to an increase of potassium excretion and also, to an increase of potassium plasma level. It has been suggested that the $C_{max}$ of drospirenone correlates to the $C_{max}$ of potassium released after drospirenone administration. Such an increase of potassium plasma concentration after drospirenone administration may lead to hyperkalemia which is known to induce various disorders such as dizziness, palpitations, muscle weakness and even cardiac arrhythmia.

When orally administered, the DRSP-containing compositions according to the invention, induces a reduced plasmatic $C_{max}$ for drospirenone. A reduced $C_{max}$ for DRSP is expected to reduce the release of potassium in plasma. Consequently, in the case of the compositions according to the invention, the tolerance for drospirenone may be improved especially for women who are predisposed to hyperkalemia, to women who suffer from kidney, liver or adrenal diseases, and for women who are on daily, long-term treatment for a chronic condition with medications predisposed to hyperkalemia. Medications predisposed to hyperkalemia include, without being limited to, non steroidal anti-inflammatory drugs, potassium-sparing diuretics, potassium supplementation, angiotensin-converting enzyme (ACE) inhibitors, angiotensin-II receptor antagonists and heparin.

Consequently, the DRSP-containing compositions according to the invention may be particularly appropriate to prepare any oral medicament in which the mean $C_{max}$ value for DRSP should be controlled in order to improve the tolerance for drospirenone. For example, the compositions according to the invention may be used for preparing Hormone Replacement Therapy medicaments (HRT).

Since the DRSP-containing composition of the invention combined a reduced $C_{max}$ with a delayed $t_{max}$ and an $AUC_{0\ h\text{-}tlast}$ sufficient to provide a contraceptive effect, the said compositions are appropriate for use in progestogen-only pills. As illustrated in Example 5, part 3, the compositions according to the present invention provide an efficient and stable contraceptive drospirenone blood level when daily administered to a female patient. Thus, the co-administration of an oestrogen to ensure contraception and cycle stability is not required. Since the mean $C_{max}$ value is significantly reduced, the contraceptive compositions of the invention provides a more stable plasma concentration of drospirenone, i.e. a DRSP plasma concentration with low fluctuations between two consecutive administrations. Such a feature further reduces the incidence of unscheduled spotting and bleeding and, thus, significantly improves the bleeding profile as compared to conventional POCs.

As described in Example 5, the compositions of the present invention remains a contraceptive even when a placebo period is introduced in the contraceptive regimen and some daily pills are missed. Accordingly, the compositions will exhibit a higher contraceptive reliability than other progestogen only pills, which will allow the patients to be less compliant with treatment without risking unwanted pregnancy.

Also the contraceptive compositions of the invention— which do not contain estrogen—will be as efficient as a combined oral pill without inducing the side effects related to estrogen, in particular, without increasing the risk of cardiovascular events. Thus, in some embodiments of the invention, the pharmaceutical compositions may be appropriate to be used as an oral contraceptive. In some other specific embodiments, the pharmaceutical composition of the invention may be used as a progestogen-only pill.

As used herein "progestogen-only contraceptive", or "progestogen-only pill" means a pill or a contraceptive which comprises progestogens as sole contraceptive agents and does not comprise any estrogen.

By "composition having an improved pharmacokinetic profile for drospirenone" as used herein, is thus meant that the oral administration of a single daily dosage unit of said drospirenone-containing composition provides a pharmacokinetic profile for drospirenone characterized by a delayed mean $t_{max}$ and a reduced mean $C_{max}$ as compared to the administration of a single daily dosage unit of Yasminelle®. The pharmacokinetic profile of Yasminelle® is described in Example 3

In some embodiments, the invention may provide a pharmaceutical DRSP-containing composition that when orally administered as a single daily dosage unit of said composition, is adapted to provide a pharmacokinetic profile for DRSP having a mean $C_{max}$ which is less than 85% of the mean $C_{max}$ obtained after the oral administration of a single dosage unit of Yasminelle®. The pharmaceutical DSRP-containing composition according to the present invention may further be characterized by, when orally administered, a single daily dosage unit of the composition is adapted to provide a pharmacokinetic profile for DRSP having a mean $t_{max}$ which is at least 150% of the mean $t_{max}$ obtained after the oral administration of a single dosage unit of Yasminelle®

Thus, the administration of a single dosage unit of the composition may provide a mean $AUC_{0\ h\text{-}tlast}$ which is sufficient to produce the pharmaceutical or the biological effect which is sought by the administration of drospirenone.

In the present invention, the pharmaceutical or biological effect generally refers to a contraceptive effect.

When the compositions of the invention are used as a contraceptive, it may be further required that the mean $AUC_{0\ h\text{-}tlast}$ obtained upon the administration of a single daily dosage unit of said composition is at least 70% of the mean $AUC_{0\ h\text{-}tlast}$ obtained in the case of Yasminelle®. In other words, in some embodiments of the invention, the daily dosage unit of the pharmaceutical composition according to the invention may possess a combination of physical and/or chemical features such that, when orally administered, the daily dosage unit is adapted to provide a pharmacokinetic profile having the following characteristics:

(i) a mean $C_{max}$ which is no more than 85% of the mean $C_{max}$ obtained after the oral administration of a single dosage unit of Yasminelle® and (ii) a mean $t_{max}$ which is at least 150% of the mean $t_{max}$ obtained after the oral administration of a single dosage unit of Yasminelle®, and, optionally, a mean $AUC_{0\ h\text{-}tlast}$ which is at least 70% of the mean $AUC_{0\ h\text{-}tlast}$ obtained after the oral administration of a single dosage unit of Yasminelle®.

In some embodiments, the mean $AUC_{0\ h\text{-}tlast}$ may be at least 85% of the mean $AUC_{0\ h\text{-}tlast}$ obtained after the oral administration of a single dosage unit of Yasminelle®. In some embodiments, the pharmaceutical compositions of the invention display one or more of the previous mentioned pharmacokinetic characteristics. The $AUC_{0\ h\text{-}tlast}$, the $c_{max}$ and the $t_{max}$ are determined based on the drospirenone plasma concentration versus time curve. According to the present invention, for a given drospirenone-containing composition, the drospirenone plasma concentration versus time curve may be determined by following plasma drospirenone concentration over a period of about 72 h after a single oral intake of one daily dosage unit of the said drospirenone-containing composition.

The single oral administration of the said drospirenone-containing composition, in one embodiment, may be preferably performed in fasting conditions i.e. without food and not close to mealtime (in general, approximately 6 h-10 h after meal) since food ingestion may modify the absorption rate of drospirenone in the gastrointestinal tract.

The $t_{max}$ and $C_{max}$ values refer to the maximum DRSP plasma concentration and the time to reach it, respectively, after the oral administration of a single daily dosage unit of the DRSP-containing composition of interest. In other words, $t_{max}$ and $C_{max}$ refer to the characteristics of drospirenone plasma concentration peak observed after the oral intake of a single daily dosage unit of the composition of interest.

The $AUC_{0\ h\text{-}tlast}$ corresponds to the area obtained by integration of the drospirenone plasma concentration versus time over the interval [0 h-tlast], the point '0 h' referring to the oral intake of a single daily dosage unit of the composition of interest and the point "$t_{last}$" refers to the last time for which plasma concentration of DRSP can be quantifiable.

DRSP plasma concentration may be determined by well-known methods. For example, an appropriate method of quantification comprises the extraction of DRSP from human plasma and then its quantification using liquid chromatography coupled with tandem mass spectrometry.

In a preferred embodiment, one skilled in the art may adapt the analytical method described by Kirk el al (Rapid Communication in Mass Spectrometry, 2006; 20:1247-1252). Such a method comprises a step of derivatization of drospirenone with Girard P hydrazine solution in order to increase the response of DRSP during the subsequent MS analysis. This method is generally appropriate to quantify DRSP in human EDTA plasma over a concentration range from about 0.25 to about 100 ng/ml.

As used herein, the mean $AUC_{0\ h\text{-}tlast}$, the mean $C_{max}$ and the mean $t_{max}$ refer to arithmetic mean values determined from individual pharmacokinetic data obtained for a group of healthy female volunteers of child-age bearing subjected to a single oral administration of one daily dosage unit of a drospirenone-containing composition. The group of healthy female volunteers may comprise enough women to provide statistically confident pharmacokinetic results. Preferably, the said group comprises at least ten healthy women of child-bearing age.

As used herein, a healthy woman of child-bearing age refers to a pre-menopause Caucasian female between 18 and 40 years, with normal body weight and with no health problem, in particular, with no metabolism, renal, liver or gynaecologic disorders. A "normal body weight" refers to a body mass index (BMI) ranging from 18 to 29 kg/m$^2$.

Preferably, such volunteers have not taken any hormone-containing compositions within 3 months prior to the trial to determine the pharmacokinetic parameters of interest.

The mean $C_{max}$, $t_{max}$ and $AUC_{0\ h\text{-}tlast}$ for Yasminelle® and for the drospirenone-containing composition according to the invention are determined for the same group of female patients. Between the administration of the single daily dosage unit of Yasminelle® and that of the DRSP-containing composition according to the invention, the female volunteers may be subjected to a washout period of at least 7 days. The mean $c_{max}$, the mean $t_{max}$ and the mean $AUC_{0\ h\text{-}tlast}$ for DRSP may be determined from raw individual pharmacokinetic data by well-known statistical methods of the prior art.

For example, all endpoints listed above may be determined in a model-independent way. The highest concentration really measured and the time at which it was registered after each dose in any given volunteer may be regarded as $C_{max}$ and $t_{max}$ respectively according to the algorithm of the program NC_PKP.sas.

The daily dosage unit of the DRSP containing-composition of the invention may comprise at least 2 mg of drospirenone. A daily amount of DRSP from 3 mg to 4.5 mg may be preferred when the composition of the invention is used as contraceptive.

As used herein, Yasminelle® is a combined oral pill commercialized by Bayer/Schering. The daily dosage unit of Yasminelle® is a coated tablet which comprises 3 mg of micronized drospirenone and ethinylestradiol betadex clathrate in an amount corresponding to 20 µg of ethinylestradiol. The tablet further comprises lactose monohydrate, maize starch and magnesium stearate as main excipients. The coating of the tablet comprises hypromellose, talc, titane oxide and iron oxide red.

As used herein, Yasminelle® (marketed under the name of Jasminelle® in France) refers to the pharmaceutical product covered by the French Marketing Authorization related to CIS number (Code d'Identification de Spécialité) 65052799 and revised on Sep. 17, 2009.

In a preferred embodiment, the pharmacokinetic parameters (namely $C_{max}$, $t_{max}$ and $AUC_{0\ h\text{-}tlast}$) are determined after the first oral administration of a single unit dosage of the DRSP-containing composition of interest, said first oral administration occurring in fasting conditions.

In a more general aspect, the present invention may provide a pharmaceutical composition comprising an active drug, when orally administered as a single daily dosage unit of said composition, is adapted to provide a pharmacokinetic profile for said active drug having a mean $C_{max}$ which is less than about 30 ng/ml. The pharmaceutical composition comprising an active drug may be further characterized in that, when orally administered, a single daily dosage unit of said composition is adapted to provide a pharmacokinetic profile for said active drug having a mean $t_{max}$ which is at least about 2.2 h.

In another embodiment, the mean $AUC_{0\ h\text{-}tlast}$ obtained upon the administration of a single daily dosage unit of said composition may be at least about 300 ng*ml/h. The daily dosage unit of the pharmaceutical composition according to the invention may possesses a combination of physical and/or chemical features such that, when orally administered, the daily dosage unit is adapted to provide a pharmacokinetic profile having the following characteristics:
  (i) a mean $C_{max}$ which is less than about 30 ng/ml
  (ii) a mean $t_{max}$ of at least about 2.2 h; and, optionally,
  (iii) a mean $AUC_{0\ h\text{-}tlast}$ of at least about 300 ng*h/ml.

In another specific embodiment, the $T_{max}$ may range from about 2.2 hrs to 6 hrs. In another specific embodiment, said $AUC_{0\ h\text{-}tlast}$ may be at least 350 ng·h/ml.

In another embodiment of the present invention, the active drug, when orally administered and provides such a pharmacokinetic profile, may be a drug that inhibits ovulation. In a specific embodiment, the active drug may be a progestogen-only contraceptive (POC). In another specific embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In a specific embodiment, the POC may be drospirenone.

In a specific embodiment, the present invention may provide a pharmaceutical DRSP-containing composition, when orally administered as a single daily dosage unit of said composition, is adapted to provide a pharmacokinetic profile for DRSP having a mean $C_{max}$ which is less than about 30 ng/ml. The said pharmaceutical DRSP-containing compositions may be further characterized in that, when orally administered, a single daily dosage unit of said composition is adapted to provide a pharmacokinetic profile for DRSP having a mean $t_{max}$ which is at least about 2.2 h.

The administration of a single dosage unit of the said composition including DRSP may provide a mean $AUC_{0\ h\text{-}tlast}$ which is sufficient to produce the pharmaceutical or the biological effect which is sought by the administration of drospirenone. Accordingly, when the compositions of the invention are used as a contraceptive, it may be further required that the mean $AUC_{0\ h\text{-}tlast}$ obtained upon the administration of a single daily dosage unit of said composition is at least about 300 ng*ml/h. In other words, in some embodiments, the daily dosage unit of the pharmaceutical composition according to the invention may possess a combination of physical and/or chemical features such that, when orally administered, the daily dosage unit is adapted to provide a pharmacokinetic profile having the following characteristics:
  (i) a mean $C_{max}$ which is less than about 30 ng/ml
  (ii) a mean $t_{max}$ of at least about 2.2 h
  and, optionally, a mean $AUC_{0\ h\text{-}tlast}$ of at least about 300 ng*h/ml In some embodiments, the pharmaceutical composition of the invention may display all the previous mentioned pharmacokinetic characteristics.

As used herein, the term "about" before a "specific value" defines a range from "the specific value minus at least 10% of the specific value" to "the specific value plus at least 10% of the specific value". For example, "about 50" defines a range from 45 or less to 55 or more. In addition, it may define a range where "the specific value minus at least 20% of the specific value" to "the specific value plus at least 20% of the specific value" Further, it may define a range where "the specific value minus at least 30% of the specific value" to "the specific value plus at least 30% of the specific value" and so on.

A mean $AUC_{0\ h\text{-}tlast}$ of at least about 300 ng*h/mL includes a mean $AUC_{0\ h\text{-}tlast}$ of at least about 310 ng*h/mL, at least about 320 ng*h/mL, at least about 330 ng*h/mL, at least about 340 ng*h/mL, at least about 350 ng*h/mL, at least about 360 ng*h/mL, at least about 370 ng*h/mL, at least about 380 ng*h/mL, at least about 390 ng*h/mL, at least about 400 ng*h/mL, at least about 410 ng*h/mL at least about 420 ng*h/mL, at least about 430 ng*h/mL. In some embodiments, the mean $AUC_{0\ h\text{-}tlast}$ is at least about 350 ng*h/ml.

A mean $t_{max}$ of at least about 2.2 h includes a mean $t_{max}$ of at least about 2.5 h, of at least about 3.0 h, of at least about 3.5 h, of at least about 4 h. In a specific embodiment, the mean $t_{max}$ does not exceed 6 hours in order to not significantly impair the bioavailability of DRSP. Thus, the mean $t_{max}$ preferably may range from about 2.2 h to about 6 h. In some embodiments, a $t_{max}$ ranges from about 3.0 h to about 4.0 h.

A mean $C_{max}$ which is less than about 30 ng/ml includes a $C_{max}$ less than about 28 ng/ml, less than about 26 ng/ml, less than about 24 ng/ml, less than about 22 ng/ml, less than about 20 ng/ml, less than about 19 ng/ml, less than about 18 ng/ml, less than about 17 ng/ml, less than about 16 ng/ml, less than about 15 ng/ml, less than about 14 ng/ml. In some embodiments, the mean $C_{max}$ ranges from about 15 ng/ml to about 30 ng/ml. In other embodiments, the mean $C_{max}$ ranges from about 15 ng/ml to about 26 ng/ml.

In certain embodiments, the daily dosage unit of the pharmaceutical composition according to the invention may be adapted to provide a pharmacokinetic profile having the following characteristics:
  (i) a mean $C_{max}$ ranges from 15 ng/ml to 30 ng/ml,
  (ii) a mean $t_{max}$ ranges from 2.2 h to 6 h, and
  (iii) optionally, a mean $AUC_{0\ h\text{-}tlast}$ of at least about 300 ng*h/ml,
  when the said daily dosage unit is administered under fasting condition.

In a specific embodiment, the pharmacokinetic parameters (namely $C_{max}$, $t_{max}$ and $AUC_{0\ h\text{-}tlast}$) may be determined after the first oral administration of a single unit dosage of the active drug, said first oral administration occurring in fasting conditions.

In one embodiment, pharmaceutical compositions may comprise an active drug, wherein a single daily dosage unit of the composition, when orally administered to a patient in fasting conditions provides a pharmacokinetic profile for the active drug having:
  i) a $T_{max}$ ranging from about 2.2 hrs to 6 hrs; and
  ii) a mean $C_{max}$ which is less than about 30 ng/ml;

In some embodiments, the oral administration of the active drug provides a pharmacokinetic profile that may further be characterized by a mean $AUC_{0\ h\text{-}tlast}$ of at least 300 ng*ml/h, more preferably of at least 350 ng*ml/h. In another specific embodiment, the mean $t_{max}$ may range from about 2.2 hrs to about 6 hrs. In another embodiment, the $C_{max}$ may range from about 15 ng/ml to about 30 ng/ml.

In another specific embodiment, the active drug may be an active contraceptive drug. In another specific embodiment, the active contraceptive drug may be a POC. In another specific embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In one specific embodiment, the POC may be drospirenone.

The pharmaceutical composition of the invention is particularly appropriate to be used as a contraceptive, in particular, as a POC. The pharmaceutical compositions of the invention may also be used for preparing any other medicaments for which the improvement of the DRSP tolerance may be sought. Such medicaments include, without being limiting to, HRT medicament.

Without wishing to be bound by any theory, the present invention shows that the in vitro dissolution rate of drospirenone is correlated to its pharmacokinetic profile in vivo. A composition displaying a pharmacokinetic profile for drospirenone as fully-described above may exhibit a slow in vitro dissolution rate of drospirenone such that no more than 50% of drospirenone initially present in the said composition is dissolved within 30 minutes.

In one aspect, the present invention provides pharmaceutical compositions comprising drospirenone that is characterized by a slow dissolution rate of drospirenone in vitro. As used herein, by "a slow dissolution rate of drospirenone in vitro" is meant that the release of drospirenone is such that no more than about 50% of drospirenone initially present in the said composition is dissolved within 30 minutes when the said composition is subjected to a dissolution test.

As intended herein, no more than about 50% of the drospirenone encompasses no more than 45%, 40%, 35%, 30%, 25%, 20%, 15%, 10% of the drospirenone initially present in the contraceptive composition. In some embodiments, no more than about 40% of the drospirenone initially present in the composition is dissolved within 30 min.

As used herein, the percentage of drospirenone is related to the amount of drospirenone initially present in the said contraceptive composition.

The in vitro dissolution rate of any active drug of the present invention, including drospirenone, may be assessed by anyone of well-known methods described in the prior art. The in vitro dissolution rate of drospirenone is preferably assessed by the USP XXIII Paddle Method. Briefly, a tablet consisting of the contraceptive composition comprising drospirenone to be tested is placed in 900 mL of water at 37° C. (±0.5° C.). The dissolution test is performed using a USP dissolution test apparatus 2 at a stirring rate of 50 rpm.

In the context of the present invention, the term "active drug" includes any compound intended to furnish pharmacological activity or other direct effect in the diagnosis, cure, mitigation, treatment and/or prevention of a condition. See 21 C.F.R. 210.3(b)(7). Further, "active drugs" include those compounds of the composition that may undergo chemical change during the manufacture of the composition and be present in the final composition in a modified form intended to furnish an activity or effect. Id. As used herein, an "active contraceptive drug" thus means an active drug that may prevent pregnancy when administered in an effective amount to a female patient through its contraceptive effect. The active contraceptive drug may prevent pregnancy to occur by various contraceptive effects. For example, the contraceptive effect may include, but is not limited to, one or more of the inhibition of ovulation, thickening of cervical mucus (which reduces the sperm viability and penetration) and/or preventing or otherwise impeding embryo implantation.

The term "drospirenone" includes drospirenone itself, i.e. the chemical entity identified by the CAS registry Number 67392-87-4, solvates of drospirenone, and derivatives or prodrugs of drospirenone.

Drospirenone may be prepared by well-known methods described in the prior art, for example, described in U.S. Pat. No. 4,129,564, WO9806738, EP11746101 or WO2006061309. The method described in WO2006061309 may be particularly suitable for preparing drospirenone. It goes without saying that the method for preparing drospirenone may be performed so as to meet the Good manufacturing practice (GMP) requirements.

To ensure a good bioavailability of the active drug, a significant amount of the active drug initially comprised in the contraceptive composition has to be released in a reasonable time range. An in vitro dissolution rate of said active drug may be such that at least 50% of the active drug initially present in the said compositions was dissolved in a time range from about 3 hours to about 4 hours. In a specific embodiment, the active drug may be a POC. In another embodiment, the POC may be drospirenone. Indeed, the Applicant showed that a good bioavailability of drospirenone was achieved in the case of compositions comprising drospirenone which had an in vitro dissolution rate of drospirenone such that at least about 50% of the drospirenone initially present in the said compositions was dissolved in a time range from about 3 hours to about 4 hours.

Accordingly, an object of the present invention is a contraceptive composition comprising drospirenone wherein the in vitro dissolution rate of the said drospirenone is such that no more than about 50% of the said drospirenone is dissolved within 30 minutes and such that at least about 50% of the drospirenone is dissolved in a time range from 3 hours to 4 hours.

A time range from about 3 hours to about 4 hours may include, in specific non-limiting embodiments, a time range from 3.25 hours, to 3.5 hours, and from 3.75 hours, to 4 hours.

At least about 50% of the active drug such as drospirenone encompasses at least 50%, 55%, 60%, 65%, 70%, 75%, 80%, 85%, at least 88%, at least 90%, at least 91%, at least 92%, at least 93%, at least 94%, at least 95%, at least 96%, at least 97%, at least 98%, at least 99%, and at least 99.5%.

In some embodiments, at least about 60% of the active drug, such as DRSP, initially present is dissolved in a time range from about 3 hours to about 4 hours. In some other embodiments, the said contraceptive composition is further characterized in that at least about 70% of the active drug, such as drospirenone is dissolved within about 6 hours.

The applicant has shown that specific surface area of DRSP has a direct impact on the in vitro dissolution rate of drospirenone and its in vivo pharmacokinetic profile.

One way to obtain the active drug-containing compositions of the invention is to use the active drug in a particle form having an appropriate specific surface area. Active drugs may be present in the pharmaceutical compositions of the invention in a non-micronized particle form. In a specific embodiment, the active drug may be a POC. For example, it has been also shown that the active drug drospirenone in a particle form having a specific surface area from about 2000 cm$^2$/g to about 8500 cm$^2$/g may be suitable for obtaining the contraceptive compositions of the invention. The specific surface area may be experimentally determined using the BET method (gas adsorption method).

In some embodiments, the contraceptive compositions of the invention comprise active drugs such as drospirenone in a particle form having a specific area from about 2000 cm$^2$/g to about 8500 cm$^2$/g. Such a specific area range which includes values of about 2000 cm$^2$/g, 2500 cm$^2$/g, 3000 cm$^2$/g, 3500 cm$^2$/g, 4000 cm$^2$/g, 4500 cm$^2$/g, 5000 cm$^2$/g, 5500 cm$^2$/g, 6000 cm$^2$/g, 6100 cm$^2$/g, 6200 cm$^2$/g, 6300 cm$^2$/g, 6400 cm$^2$/g, 6500 cm$^2$/g, 6600 cm$^2$/g, 6700 cm$^2$/g, 6800 cm$^2$/g, 6900 cm$^2$/g, 7000 cm$^2$/g, 7500 cm$^2$/g, 8000 cm$^2$/g and 8500 cm$^2$/g.

In a specific embodiment, concerning the size particle distribution, active drugs particles having a diameter greater than 200 µm are preferably avoided. In a specific embodiment, drospirenone particles having a diameter greater than 200 µm are preferably avoided in order to not drastically impair the in vitro dissolution rate and, thus, the in vivo bioavailability since such particles are poorly soluble. In a specific embodiment, drospirenone may preferably have a d50 of less than about 70 µm. In a preferred embodiment, the d50 of the drospirenone particles may range from about 10 µm to about 60 µm. A d50 ranges from about 10 µm to about 60 µm encompasses a d50 of about 10 µm, of about 15 µm, of about 20 µm, of about 25 µm, of about 30 µm, of about 35 µm, of about 40 µm, of about 45 µm, of about 50 µm, of about 55 µm and of about 60 µm.

In some embodiments, the particle size distribution of the active drug present in the composition according to the invention may be characterized by:
 (i) a d90 particle size less than about 100 µm, and/or
 (ii) a d50 particle size ranging from about 10 µm to about 60 µm and/or
 (iii) a d10 particle size more than about 3 µm.

In some other embodiments, the d50 of the active drug particles may range from about 10 µm to about 30 µm. In a specific embodiment, the active drug may be a POC. In such embodiments, the particle size distribution of the POC present in the composition according to the invention is characterized by at least one of the following characteristics:
 (i) a d90 particle size less than about 100 µm,
 (ii) a d50 particle size ranging from about 10 µm to about 30 µm and
 (iii) a d10 particle size more than about 3 µm.

In a specific embodiment, the particle size distribution of, drospirenone present in the composition according to the invention may be characterized by:
 (iv) a d90 particle size less than about 100 µm, and/or
 (v) a d50 particle size ranging from about 10 µm to about 60 µm and/or
 (vi) a d10 particle size more than about 3 µm.

In other specific embodiments, the d50 of drospirenone particles may range from about 10 µm to about 30 µm. In such embodiments, the particle size distribution of the drospirenone present in the composition according to the invention is characterized by at least one of the following characteristics:
 (iv) a d90 particle size less than about 100 µm,
 (v) a d50 particle size ranging from about 10 µm to about 30 µm and
 (vi) a d10 particle size more than about 3 µm.

As used herein, the term "about" before a "specific value" defines a range from "the specific value minus 10% of the specific value" to "the specific value plus 10% of the specific value". For example, "about 50" defines a range from 45 to 55. In addition, it may define a range where "the specific value minus at least 20% of the specific value" to "the specific value plus at least 20% of the specific value." Further, it may define a range where "the specific value minus at least 30% of the specific value" to "the specific value plus at least 30% of the specific value" and so on.

As used herein, by "d90 particle size" is meant that the particle size distribution is such that at least 90% of the particles have a particle size diameter of less than the specified value.

As used herein, by "d50 particle size" is meant that the particle size distribution is such that at least 50% of the particles have a particle size diameter of less than the specified value.

As used herein, by "d10 particle size" is meant that the particle size distribution is such that at least 10% of the particles have a particle size diameter of less than the specified value.

d90 particle size less than about 100 µm may include d90 particle sizes less than about 90 µm, 80 µm, 70 µm, 60 µm, 55 µm, 50 µm, 45 µm, 40 µm, 38 µm, 36 µm, 34 µm, 32 µm, 30 µm, 28 µm, 26 µm, 24 µm, 22 µm, 20 µm, and 20 µm.

d50 particle size values ranging from about 10 µm to about 30 µm may include values of about 10 µm, 11 µm, 12 µm, 13 µm, 14 µm, 15 µm, 16 µm, 18 µm, 19 µm, 20 µm, 21 µm, 22 µm, 23 µm, 24 µm, 25 µm, 26 µm, 27 µm, 28 µm, 29 µm, 30 µm.

d10 particle size values more than about 3 µm may include d10 particle size values more than about 3 µm, 3.5 µm 4.5 µm, 5 µm, 6 µm, 7 µm, 8 µm, 9 µm, 10 µm, 11 µm, and 12 µm. It goes without saying that d10 particle size value is smaller than d50 particle size value which is smaller than d90 particle value.

The active drug (such as drospirenone) particle size distribution, in particular d90, d10 and d50 values, may be determined by well-known methods of the prior art such as sieve analysis, laser diffraction methods, photoanalysis or optical counting methods. Laser diffraction methods are particularly preferred. As illustrated in the Example 1, the particle size distribution may be determined by laser diffraction in wet dispersion. The dispersant is preferably water.

In some embodiments, the pharmaceutical composition of the invention may comprise drospirenone in a particle form having a particle size distribution having a combination of two characteristics selected from:
 (i) a d90 particle size less than about 100 µm,
 (ii) a d50 particle size ranging from about 10 µm to about 30 µm and
 (iii) a d10 particle size more than about 3 µm.

In other words, the particle size distribution of DRSP display a combination of characteristics selected from characteristic (i) and characteristic (ii), characteristic (i) and characteristic (iii), and, characteristic (ii) and characteristic (iii).

In some other embodiments, the pharmaceutical composition of the invention comprising drospirenone in a non-micronized form having a particle size distribution characterized in that:
 (i) d90 particle size is less than about 100 µm,
 (ii) d50 particle size ranging from about 10 µm to about 30 µm and
 (iii) d10 particle size is more than about 3 µm In a preferred embodiment, the DRSP particle distribution may be further characterized in that the d90 particle size value is less than about 50 μm and in that no particle has a size greater than 80 μm.

In some embodiments, the contraceptive composition of the invention may comprise drospirenone in a particle form having a d90 particle size which ranges from about 20 μm to about 40 μm, a d50 particle size which ranges from about 10 μm to about 30 μm and a d10 which ranges from about 3 μm to about 9 μm and wherein no particle has a size greater than 80 μm, more preferably no particle has a size greater than about 60 μm.

In some other embodiments, the contraceptive composition of the invention may comprise drospirenone in a particle form having:
  (i) a d90 particle size which ranges from about 30 μm to about 40 μm,
  (ii) a d50 particle size which ranges from about 15 μm to about 25 μm and
  (iii) a d10 which ranges from about 5 μm to about 9 μm and wherein no particle has a size greater than 80 μm, more preferably no particle has a size greater than 60 μm.

For illustrative purposes, an appropriate particle size distribution of drospirenone according to the invention is shown in FIG. 1.

In some other embodiments, the contraceptive composition of the invention may comprise drospirenone in a particle form having a specific surface area from about 2000 $cm^2/g$ to about 8000 $cm^2/g$ and having a d50 particle size ranges from about 10 μm to 60 μm.

To obtain drospirenone in a particle form having the specific surface area and/or the particle size distribution as described above, one skilled in the art may use well-known methods of the prior art such as a milling process optionally combined with a sieve process. For example, drospirenone, obtained by anyone of the synthesis methods described in the prior art, may be subjected to a ball mill or hammer mill step, optionally followed by vibrating sieve steps. The subsequent vibrating sieve steps may remove the finest and biggest particles of drospirenone which would impair the pharmacokinetic profile and the in vitro dissolution profile of drospirenone.

One skilled in the art may adjust the parameters of the milling and sieve steps by routine experiments to obtain the appropriate particle form of drospirenone. Appropriate mills which may be used include a fluid energy mill, a ball mill or rod mill, a hammer mill, a cutting mill and an oscillating granulator.

An appropriate particle form of, a POC, such as drospirenone may also be prepared by a crystallisation or precipitation process optionally combined with a sieve step in order to fully control the size of POC/drospirenone particles. For example, the precipitation process may comprise the steps of (i) dissolving drospirenone in a water-miscible solvent and then (ii) dispersing the resulting solution in cold water under stirring so that to induce the precipitation of drospirenone. The drospirenone particles may be then recovered by a filtration process.

The water-miscible solvents may be a solvent commonly used in crystallisation or precipitation process such as methanol, ethanol, isopropanol, dimethylformamide, tetrahydrofuran, dioxane or dimethyl sulfoxide, dimethylacetamide or acetone.

Such a process enables one skilled in the art to obtain a POC, such as drospirenone, essentially in a crystallized form.

By routine experiments, one skilled in the art may determine the parameters of the precipitation process to be used so as to obtain the appropriate form of drospirenone. One skilled in the art may adjust the parameters of the said precipitation process (such as the amounts of solvent, of water and optionally that of surfactant to be used) by routine experiments.

As described above, when the pharmaceutical composition of the invention is a contraceptive composition, the said composition may provide a pharmacokinetic profile of drospirenone such that the presence of an estrogenic compound to ensure the contraceptive efficiency of the said compositions is not required.

Accordingly, in specific embodiments, the contraceptive compositions of the invention do not comprise an estrogen, including phytoestrogen. As used herein, the term "estrogen" refers to compounds, such as ethinylestradiol, mestranol or the phytoestrogen 8-prenylnaringenin, that are able to bind and activate estrogen receptors. In other words, the DRSP is present in the contraceptive compositions of the present invention without estrogen, which means that DRSP is not associated with or combined with an estrogen as in the case of combined oral pill.

In some embodiments, drospirenone is the sole contraceptive ingredient comprised in the contraceptive compositions, i.e. the sole active ingredient able to prevent pregnancy when administered to a female patient of child-age bearing.

However, in some specific embodiments of the present invention, drospirenone may be combined with one or more progestogens. The term "progestogen", as used herein, refers to any compound that binds and activates the progesterone receptor.

Progestogens include, but are not limited to, 17-hydroxy progesterone esters, 19-nor-17-hydroxy progesterone esters, 17□-ethinyltestosterone and derivatives thereof, 17□-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17-acetoxy-13-ethyl-17-a-ethinyl-gon-4-en-3-one oxime, cyproterone acetate, gestodene, desogestrel, etonorgestrel, norgestimate, norelgestromin, chlormadione and dienogest.

In some other embodiments, the drospirenone may be combined with one or more active ingredients which do not have contraceptive activities. Such active ingredients include, without being limited to, antiemetic agents, vitamins such as folic acid, vitamin B12, vitamin D, minerals and oligo elements such as iron, iodine, selenium and others.

The contraceptive compositions of the invention may comprise drospirenone in an amount corresponding to a daily dosage which prevents pregnancy when the said contraceptive composition is administered to a woman over a single treatment period of 21 to 28 days.

As described in the Example 3 related to a clinical trial, the oral administration of a single daily dosage unit of a composition according to the invention and comprising 3 mg of DRSP, obtains a mean $AUC_{0\ h\text{-}tlast}$ value of 368 ng*h/ml, which corresponds to 88% of the mean $AUC_{0\ h\text{-}tlast}$ resulting from the oral administration of a single dose of Yasminelle®.

In a specific embodiment, the pharmaceutical compositions of the invention may be a contraceptive composition which comprises drospirenone in an amount corresponding to a daily dose of at least about 2 mg of drospirenone. At least about 2 mg of drospirenone may encompass at least about 3 mg of drospirenone, at least about 3.5 mg of drospirenone, and at least about 4 mg of drospirenone.

In some embodiments, the active daily dosage unit which includes the contraceptive composition as described above may comprise an active drug in amount ranging from about 2 mg to about 6 mg. In a specific embodiment, the POC may be in an amount ranging from about 2 mg to about 6 mg. In another specific embodiment, the POC may be DRSP. A daily dose ranging from about 2 mg to about 6 mg may encompass daily doses of 2.0 mg, 2.5 mg, 3.0 mg, 3.5 mg, 4.0 mg, 4.5 mg, 5.0 mg, 5.5 mg, and 6 mg. In a specific embodiment, the daily dose of the POC, such as DRSP, may be about 2 mg.

In a specific embodiment, the contraceptive compositions of the invention may comprise DRSP in an amount corresponding to a daily dosage which ensures ovulation inhibition when the said contraceptive composition is administered to a woman over a single treatment period of 21 to 28 days.

The daily dose of drospirenone may range from about 3 mg to about 6 mg, and specifically from about 3 mg to about 4.5 mg. In some embodiments, the amount of drospirenone may correspond to a daily dose of about 4.0 mg. However, the daily dose of drospirenone to be administered to a female patient in need thereof may also be adjusted depending on individual factors such as the age, the body weight, the general health and the diet of the female patient. The said daily dose may also vary upon the drug interaction which may occur. The said daily dose may also vary upon the additional biological effect(s), other than the prevention of pregnancy, which may be sought through the administration of DRSP.

The daily dose of drospirenone to be daily administered to a female patient may be lower or higher than the doses previously mentioned. For example, a female patient in peri-menopause may require a higher or lower daily dosage of drospirenone, in order to improve her general conditions and, for example, in order to improve the regularity of her menstrual cycles. The adjustment of the daily dosage may be routinely determined by practitioners.

Figure 6A:
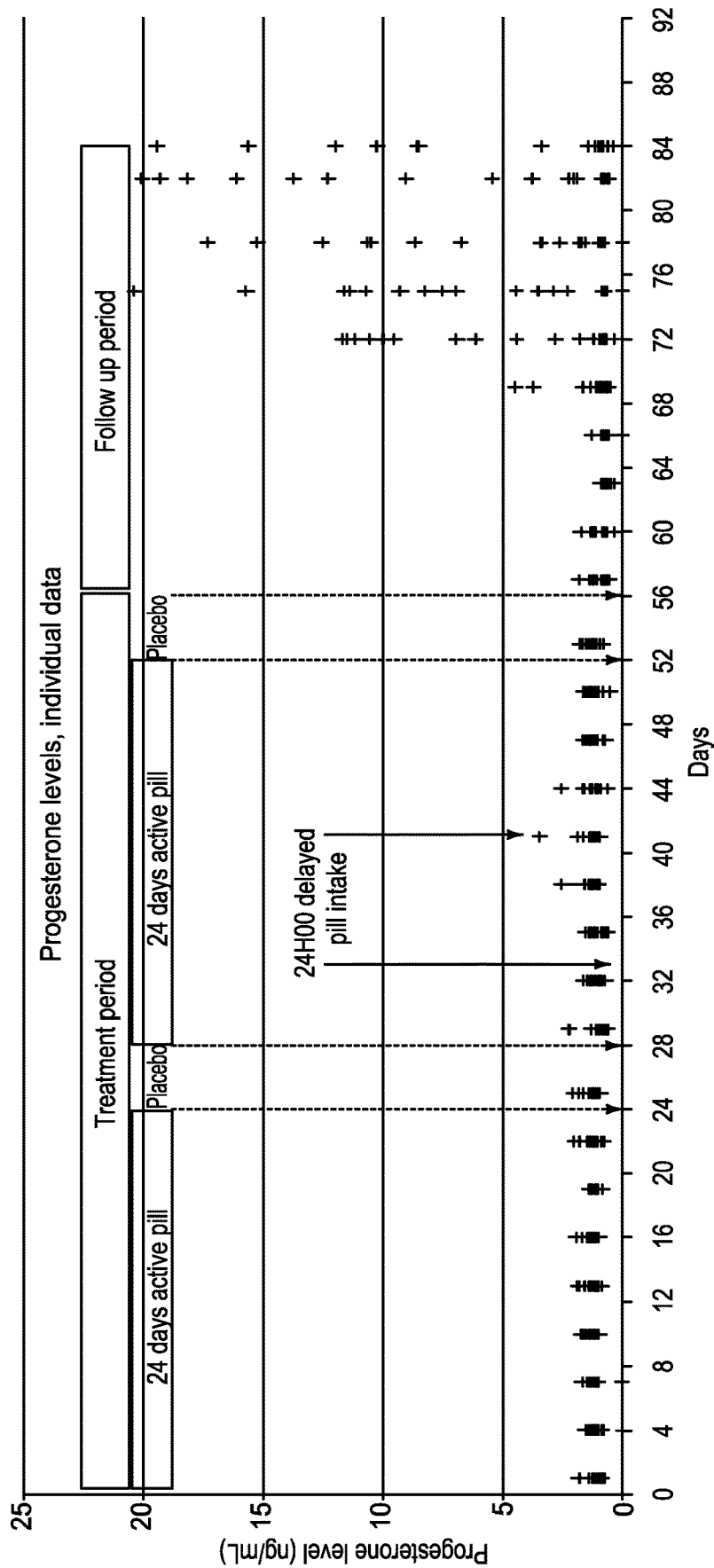
FIGS. 6a and 6b: Individual Plasma Levels of Progesterone and Estradiol in Patients During Treatment Period and Follow Up Period.
Figure 6B:
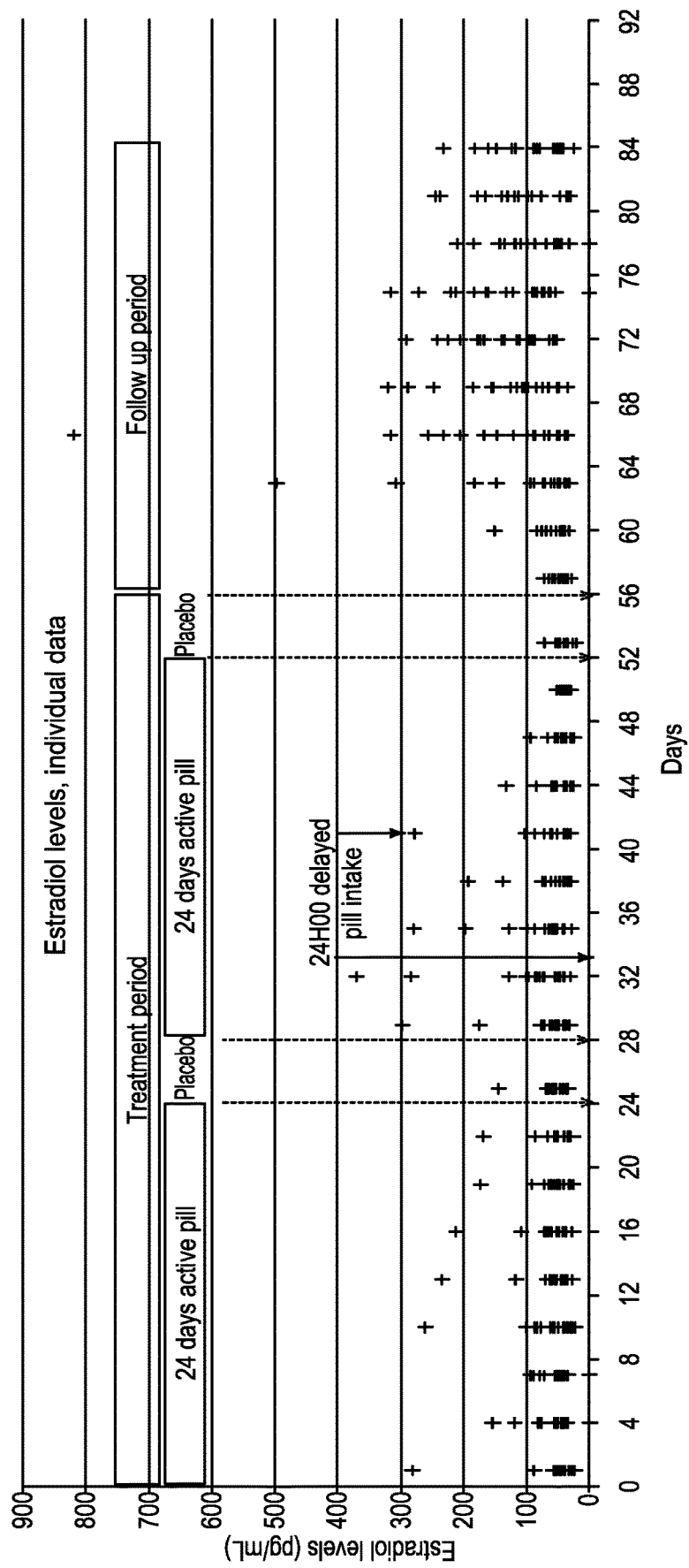

In another embodiment of the present invention, the pharmaceutical composition may comprise an active contraceptive drug that allows for a 24/4 regimen. As defined herein, a "24/4 regimen" is a daily dosing regimen for establishing its contraceptive effect within a period of a total of 28 days that allows for the patient to have an active contraceptive drug administered once a day on 24 days of the 28 period, but allow the patient to skip up to 4 doses of the 28 day daily dosing regimen period. In other words a patient may miss up to 4 doses i.e., 4 days of a 28 day period, without taking the active contraceptive drug, and still continue to prevent pregnancy. A non-limiting example of the 24/4 regimen is depicted in FIGS. 6a-b. As demonstrated, the subjects were administered an active contraceptive drug (DRSP) on days 1-24 and a placebo on days 25-28 of each treatment cycle at a fixed hour. FIGS. 6a and 6b show the 24/4 regimen for two consecutive 28 day periods; the data show the plotted individual values for plasma progesterone levels and plasma estradiol levels, respectively. Accordingly, in a specific embodiment of present invention, the prevention of pregnancy may be due to the inhibition of ovulation.

The results show that during the 2 consecutive 24/4 regimens, no ovulation occurred. Conversely, upon cessation of treatment, during the 28-day follow-up cycle, the progesterone levels increased above 5.04 ng/mL in 17 out of 20 women showing a return of ovulation. The data confirms that the composition of the invention, when used as an active contraceptive drug (DRSP) upon a 24/4 regimen, provided reliable inhibition of ovulation, even due to the patient missing 4 doses during each 28 day period. Accordingly, in a specific embodiment, the present invention may include a pharmaceutical composition comprising an active contraceptive drug, wherein the pharmaceutical composition allows for a 28 day daily dosing regimen, and wherein after initial administration of the active contraceptive drug has established its contraceptive effect in a patient, the patient may skip up to 4 doses within any 28 day daily dosing regimen period.

In another specific embodiment, the active contraceptive drug may be a progestogen-only contraceptive (POC). In another specific embodiment, the POC may be DRSP. In another specific embodiment, the active contraceptive drug may inhibit ovulation. In another specific embodiment, the contraceptive effect may comprise inhibiting ovulation. In a specific embodiment of the present invention, a pharmaceutical composition may comprise a progestogen-only contraceptive (POC) for inhibiting ovulation, wherein the pharmaceutical composition allows for a 28 day daily dosing regimen, and wherein after initial administration of the POC has inhibited ovulation in a patient, the patient may skip up to 4 doses within any 28 day daily dosing regimen period. In a specific embodiment, the POC may be DRSP.

In a specific embodiment, the skipped up to 4 doses may be on non-consecutive days. In another example, only 2 doses of the 4 skipped doses may be on non-consecutive days (i.e. 2 skipped doses are on consecutive days). In another example, only 1 dose of the 4 skipped doses may be on non-consecutive days (i.e. 3 skipped doses are on consecutive days). In another embodiment, the skipped 4 doses may be on consecutive days, and so on.

In another embodiment, the pharmaceutical compositions may comprise a active contraceptive drug that also allows for a 28 day dosing regimen wherein a patient may skip up to two non-consecutive days of the active contraceptive drug, provided the skipped dose is taken within about 24 hrs afterwards. In other words, the prevention of pregnancy may be maintained even if the administration of the active contraceptive drug was delayed for 24 hours in two separate non-consecutive days within the 28 day daily dosing regimen. Accordingly, the day after each non-consecutive skipped dose, two doses are administered to the patient within 24 hrs. FIGS. 6a-b also provides a non-limiting example of this concept. During the second 28 day period, the subjects took one tablet of 4 mg DRSP from day 1 to day 24 with the exception of day 5 and day 13 of the second 28 day period. On these two days, the tablet intake was delayed for 24 hours (i.e., no pill was taken on day 5 and day 13 and a tablet was taken once on day 6 and once on day 14, respectively). The data demonstrates that ovulation inhibition was maintained even if the administration of the tablet was delayed for 24 hours in two separate times within one 28 day period. Thus, in a specific embodiment, the present invention may be a pharmaceutical composition that allows during a 28 day daily dosing regimen for the patient to skip up to two non-consecutive days of an active contraceptive drug, provided the active contraceptive drug skipped dose is taken within about 24 hrs after the up to two skipped non-consecutive days. In another specific embodiment, the up to two skipped non-consecutive days may be included in a 28 day daily dosing regimen that also includes the 24/4 regimen, i.e., one 28 day daily dosing regimen may include 4 days of skipped doses and up to two non-consecutive days where the dose is delayed. In another embodiment, the active contraceptive drug may be a POC. In a specific embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In a specific embodiment the POC may be drospirenone. In another specific embodiment, the daily dose of drospirenone may comprise a dosage amount of at least about 2 mg.

The pharmaceutical compositions of the invention are suitable for patients who are women of child-bearing age. It should be noted that the contraceptive methods of the invention may be suitable for women whose health conditions are not compatible with high peak of drospirenone plasma concentration. Such women include, without being limited to, subjects with renal impairment, women predisposed to hyperkalemia and subjects who concomitantly take potassium sparing drugs. The contraceptive methods of the invention are also particularly suitable for women for whom the administration of estrogens is not recommended. Such women include, without being limited to, women predisposed to cardiovascular disorders, women who smoke and breast-feeding women. In a specific embodiment, the patient may have a higher risk for developing a complication from the administration of an estrogen than the general population. In a specific embodiment, the complication from the administration of an estrogen may be due to the patient having one or more conditions or characteristics selected from the group consisting of a higher risk for developing thromboembolism than the general population, acquired or genetic thrombophilia or hypercoagulability, an age of 35 years or over who smoke cigarettes, a higher risk for stroke than the general population, sickle-cell disease or sickle-cell anemia, a higher risk than the general population for myocardial infarction, and women currently lactating.

In a specific embodiment, the pharmaceutical compositions of the invention may further comprise one or more pharmaceutically acceptable excipients.

The pharmaceutical compositions of the invention may be formulated according to standard methods such as those described e.g., IN REMINGTON: THE SCIENCE AND PRACTICE OF PHARMACY (Lippincott Williams & Wilkins; Twenty first Edition, 2005).

Pharmaceutically acceptable excipients that may be used to formulate the contraceptive composition of the invention are, in particular, described in the HANDBOOK OF PHARMACEUTICALS EXCIPIENTS, AMERICAN PHARMACEUTICAL ASSOCIATION (Pharmaceutical Press; 6th Revised edition, 2009). Examples of appropriate excipients include, but are not limited to, fillers, carriers, diluents, binders, anti-caking agents, plasticizers, disintegrants, lubricants, flavors, buffering agents, stabilizers, colorants, dyes, anti-oxidants, anti-adherents, softeners, preservatives and glidants.

In some embodiments, the contraceptive compositions of the invention may comprise one or more excipients selected from the group of binders, fillers, glidants and lubricants. Examples of fillers include, without being limited to, lactose anhydrous, microcrystalline cellulose, starch, pregelatinized starch, modified starch, dibasic calcium phosphate dihydrate, calcium sulfate trihydrate, calcium sulfate dihydrate, calcium carbonate, lactose, dextrose, sucrose, mannitol and sorbitol and combinations thereof. Examples of lubricants include, without being limited to, magnesium stearate, calcium stearate, zinc stearate, talc, propylene glycol, PEG, stearic acid, vegetable oil, sodium benzoate, sodium lauryl sulfate, magnesium lauryl sulfate, mineral oil polyoxyethylene monostearate and combinations thereof. Examples of binders include, without being limited to, starches, e.g., potato starch, wheat starch, corn starch; gums, such as gum tragacanth, acacia gum and gelatin; microcrystalline cellulose, hydroxypropyl cellulose, hydroxyethyl cellulose and hydroxypropylmethyl cellulose; polyvinyl pyrrolidone and combinations thereof. Examples of glidants include silicon dioxide, magnesium trisilicate, powdered cellulose, starch, talc and tribasic calcium phosphate.

In a specific embodiment, the pharmaceutical compositions according to the invention do not comprise a significant amount of a surfactant agent. For example, a significant amount of a surfactant agent may impair the in vitro dissolution profile of DRSP by increasing its initial rate of dissolution. Surfactant agents include non-ionic surfactants such as polyoxyethylene sorbitan fatty acid esters and ionic surfactants such as sodium lauryl sulphate.

In some embodiments, the pharmaceutical composition of the invention may comprise drospirenone, at least one binder and at least one filler wherein:
  (i) the amount of drospirenone accounts for 1% to 10% by weight
  (ii) the amount of the at least one binder accounts for 50% to 65% by weight and
  (iii) the amount of the at least one filler accounts for 25% to 35% by weight,
  the percentages by weight being related to the total weight of the said contraceptive composition.

In some embodiments, the contraceptive composition may further comprise at least one glidant and at least one lubricant wherein:
  (iv) the amount of the at least one glidant accounts for 0.2% to 6% by weight and
  (v) the amount of the at least one lubricant accounts for 0.2% to 0.6% by weight, the percentages by weight being related to the total weight of the said contraceptive composition.

It goes without saying that the active drug, such as drospirenone, may be used in a particle form having the specific surface area and/or the d90, d10 and d50 particle sizes which are fully-described in the present specification. The said contraceptive composition may optionally comprise additional excipients which may accounts for about 0.1% to about 10% by weight.

In some other embodiments, the contraceptive compositions of the invention comprise drospirenone, at least one binder, at least one filler, at least one glidant, and at least on lubricant wherein:
  (i) the at least one binder is microcrystalline cellulose
  (ii) the at least one filler is anhydrous lactose
  (iii) the at least one glidant is silicon dioxide and
  (iv) the at least one lubricant is magnesium stearate.

The contraceptive compositions according to the invention may be formulated in a gelanic form suitable for oral administration. Such forms include, without being limited to, tablets, caplets, granules, pills, capsules, powders and suspension.

In specific embodiments, the contraceptive compositions may be formulated in a solid form for oral administration such as tablets, capsules, granules, caplets and pills. Such solid forms are particularly appropriate to be used as daily active dosage unit in the contraceptive kit according to the present invention.

When the pharmaceutical composition is formulated in solid forms such as tablets or pills, the solid forms may be conveniently coated with a suitable film-forming agent such as hydroxypropylmethyl cellulose, hydroxypropyl cellulose or ethyl cellulose, to which a suitable excipient may optionally be added, e. g. a softener such as glycerol, propylene glycol, diethylphthalate or glycerol triacetate, a filler such as sucrose, sorbitol, xylitol, glucose or lactose, or a colorant such as titanium hydroxide, etc. The pharmaceutical composition in the form of tablets, pills or granules may be prepared by conventional methods such as direct compression, dry granulation and wet granulation. In some embodiments, the solid forms are obtained by direct compression.

A further object of the invention is to provide a method for preparing the contraceptive composition as described herein which comprises the steps of:
(i) providing drospirenone in a particle form as fully-described previously in the present specification
(ii) providing one or more pharmaceutically acceptable excipients; and
(iii) mixing the drospirenone provided in step (i) with the one or more excipients provided in step (ii).

As fully-described above, the Applicant provides technical guidelines to obtain a composition comprising DRSP in a form such that:
(i) no more than 50% of the drospirenone initially present in the said composition is dissolved within 30 minutes and
(ii) at least 50% of the said drospirenone is dissolved in a time range from 3 hours to 4 hours, when the composition is subjected to an in vitro dissolution test, the percentages of drospirenone being related to the amount of drospirenone initially present in the said composition.

A DRSP containing composition with such an in vitro dissolution profile or the in vivo pharmacokinetic profile fully-described above may be achieved by various other ways.

By routine experiments and in view of his general knowledge, one skilled in the art may modify (i) the particle size distribution of DRSP and (ii) the amounts and the nature of excipients in order to obtain other alternative compositions displaying the in vitro dissolution profile and the in vivo pharmacokinetic profile described in the present application. For example, one skilled in the art may conceive a composition comprising (i) micronized DRSP together with (ii) a slow release agent in order to diminish the dissolution rate of said DRSP. One skilled in the art may also combine (i) large particles of DRSP together with (ii) a surfactant and/or a wetting agent in order to ensure the dissolution of said DRSP. Generally, non-micronized and essentially crystallized form DRSP is preferably used for preparing the pharmaceutical composition of the invention.

2. Contraceptive Methods

In one general embodiment, the present invention provides methods for producing a particular pharmacokinetic profile of an active drug in a patient. The pharmacokinetic profile may be measured in a patient after being orally administered as a single daily dosage unit of the active drug to the patient. In another embodiment, the administration of the active drug to the patient is during fasting conditions. In a specific embodiment, the active drug may inhibit ovulation.

In a specific embodiment, the methods of the present invention may produce a particular pharmacokinetic profile based on $C_{max}$, $t_{max}$, and AUC. In a specific embodiment, the methods may comprise producing a pharmacokinetic profile of an active contraceptive drug in a patient.

In a specific embodiment, the methods may comprise producing a pharmacokinetic profile of an active drug (such as DRSP) in a patient, wherein said pharmacokinetic profile comprises a mean $T_{max}$ ranging from about 2.2 hrs to about 6 hrs, and a mean $C_{max}$ which is less than about 30 ng/ml, wherein said pharmacokinetic profile is measured in said patient after orally administering a single daily dosage unit of said active drug to said patient in fasting conditions. In a specific embodiment, the pharmacokinetic profile may additionally comprise an $AUC_{0\ h\text{-}tlast}$ which is at least about 300 ng·h/ml. In another specific embodiment, the $AUC_{0\ h\text{-}tlast}$ is at least about 350 ng·h/ml. In another specific embodiment, the active drug may be an active contraceptive drug. In another specific embodiment, the active contraceptive drug may be a POC. In another specific embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In one specific embodiment, the POC may be drospirenone.

When orally administered, the pharmaceutical composition of the invention provides a significantly improved pharmacokinetic profile for drospirenone characterized by a similar $AUC_{[0\ h\text{-}tlast]}$, a delayed $t_{max}$ and a reduced $C_{max}$ as compared to that obtained with Yasminelle®. In order to conceive a contraceptive based on the said pharmaceutical composition, the presence of an estrogen such as ethinylestradiol or 8-prenylnaringenin is not required to ensure the ovulation inhibition and the cycle stability.

Moreover it is expected that such compositions may be more reliable than POCs described in the prior art. The contraceptive compositions of the invention which do not comprise an estrogen are thus particularly appropriate to be used as a progestogen-only contraceptive.

Accordingly, another object of the present invention is the use of the pharmaceutical composition as described herein for preparing a contraceptive progestogen-only pill or for preparing a contraceptive kit. A further object of the present invention is to provide an oral contraceptive method for a female patient in need thereof characterized in that it comprises the step of administering active daily dosage units consisting of a pharmaceutical composition as fully-described herein to the female patient over a period of several consecutive days, preferably over a period of 21 to 28 days.

As used herein a contraceptive method relates to a method for preventing pregnancy. As used herein, "an active daily dosage unit" means a dosage unit which is able to prevent pregnancy when daily administered to a female patient over a period selected from periods of 21 to 28 consecutive days.

In specific embodiments, the active daily dosage unit may inhibit ovulation when administered daily to a female patient over a period selected from periods of 21 to 28 consecutive days As used herein, a female patient refers to a woman of child-bearing age, i.e. from puberty to menopause. Women of child-bearing age also include women in peri-menopause.

In a specific embodiment, the said daily dosage units do not comprise an estrogen. In some embodiments, the drospirenone is the sole contraceptive ingredient comprised in the said contraceptive composition.

The contraceptive methods of the invention, in one embodiment, may be performed for a period of time corresponding to the average length of a menstrual cycle, i.e. 28 days, and may be iterated during several consecutive months up to several years or more.

In some embodiments, the contraceptive methods of the invention comprise administering "continuously" daily dosage units of the invention. Such a method does not comprise a free-contraceptive period, i.e. a period in which no contraceptive is administered.

In other embodiments, the contraceptive method of the invention comprises two consecutive phases:
  a first phase wherein active daily dosage units of the invention which do not comprise estrogen are administered to the female patient over a period of 21 to 27 consecutive days and
  a second phase wherein no contraceptive composition is administered to the female patient over a period of 1 to 7 consecutive days.

As used herein, a period of 1 to 7 consecutive days include periods of 1 day, of 2 consecutive days, of 3 consecutive days, of 4 consecutive days, of 5 consecutive days, of 6 consecutive days, and of 7 consecutive days.

As used herein, a period of 21 to 27 consecutive days include periods of 21 consecutive days, of 22 consecutive days, of 23 consecutive days, of 24 consecutive days, of 25 consecutive days, of 26 consecutive days, and of 27 consecutive days.

As mentioned above, the duration of the first phase plus the second phase may be 28 days. In the first phase, the composition of active daily dose units may remain constant, in particular in respect to the daily amount of drospirenone.

In some other embodiments, the composition of the active daily dose units may vary, in particular, in respect to the daily amount of drospirenone.

The second phase may be a free-contraceptive period, i.e. a phase during which no contraceptive ingredient is administered to the female patient. During the said second phase, daily placebo dosage units may be administered to the female patient. In some other cases, no pill is administered to the female patient.

Such a second phase may enable regular menstrual bleedings to occur and thus may enable to mimic the natural menstrual cycle. Moreover, the said second phase enables the secretion of endogenous estradiol, which may benefit bone metabolism of the female patient.

As used herein, the term "active daily dosage unit" refers to physically discrete units suitable as unitary dosages which include a contraceptive composition as fully described hereabove in the present specification. As mentioned previously, the active daily dosage unit may generally comprise a drospirenone amount of about 3.0 mg to about 6.0 mg, more preferably, of about 3.5 mg to about 4.5 mg.

In some embodiments, the first phase of the contraceptive method may last from 21 to 24 consecutive days and the second phase of the contraceptive method may last from 4 to 7 consecutive days.

In some embodiments, the first phase of the contraceptive method may last 24 consecutive days and the second phase of the contraceptive method may last 4 consecutive days.

The contraceptive methods of the invention may provide a high contraceptive efficiency without the disadvantages (i.e., spottings, irregular bleedings . . . ) observed for marketed progestogen-only contraceptive methods such as Cerazette® (Desogestrel). The contraceptive methods exhibit a higher reliability than other progestogen-only contraceptive methods by allowing the patients to be less compliant with treatment (i.e. allowing episotic missing pills) without risking unwanted pregnancy (see Example 4 hereunder).

The contraceptive methods of the invention are suitable for patients who are women of child-bearing age. It should be noted that the contraceptive methods of the invention may be suitable for women whose health conditions are not compatible with high peak of drospirenone plasma concentration. Such women include, without being limited to, subjects with renal impairment, women predisposed to hyperkalemia and subjects who concomitantly take potassium sparing drugs. The contraceptive methods of the invention are also particularly suitable for women for whom the administration of estrogens is not recommended. Such women include, without being limited to, women predisposed to cardiovascular disorders, women who smoke and breast-feeding women. In a specific embodiment, the patient may have a higher risk for developing a complication from the administration of an estrogen than the general population. In a specific embodiment, the complication from the administration of an estrogen may be due to the patient having one or more conditions or characteristics selected from the group consisting of a higher risk for developing thromboembolism than the general population, acquired or genetic thrombophilia or hypercoagulability, an age of 35 years or over who smoke cigarettes, a higher risk for stroke than the general population, sickle-cell disease or sickle-cell anemia, a higher risk than the general population for myocardial infarction, and women currently lactating.

In another embodiment, the methods of the present invention may comprise administering a pharmaceutical composition comprising an active contraceptive drug, wherein the pharmaceutical composition allows for a 24/4 regimen. Specifically, the methods may comprise administering a composition comprising an active contraceptive drug, wherein the pharmaceutical composition allows for a 28 day daily dosing regimen, and wherein after initial administration of the active contraceptive drug has established its contraceptive effect in a patient, the patient may skip up to 4 doses within any 28 day daily dosing regimen period. In another embodiment, the skipped up to 4 doses may be consecutive or non-consecutive days. In another embodiment, the methods may include a dosing regimen that allows for administration of the tablet to be delayed for 24 hours in two separate times within one day daily dosing regimen. In a specific embodiment, the methods may include administering a pharmaceutical composition that further allows during a 28 day daily dosing regimen for the patient to skip up to two non-consecutive days of a an active contraceptive drug, provided the an active contraceptive drug skipped dose is taken within about 24 hrs after the up to two skipped non-consecutive days. In another embodiment, the methods may allow for the administration of an active contraceptive drug that allows for the 24/4 regimen and the up to two delayed non-consecutive days regimen. In another specific embodiment, the active contraceptive drug may inhibit ovulation. In another specific embodiment, the contraceptive effect may comprise inhibiting ovulation.

In another embodiment, the methods of the present invention may comprise administering a pharmaceutical composition comprising a progestogen-only contraceptive (POC) for inhibiting ovulation, wherein the pharmaceutical composition allows for a 24/4 regimen. Specifically, the methods may comprise administering a composition comprising a POC for inhibiting ovulation, wherein the pharmaceutical composition allows for a 28 day daily dosing regimen, and wherein after initial administration of the POC has inhibited ovulation in a patient, the patient may skip up to 4 doses within any 28 day daily dosing regimen period. In another embodiment, the skipped up to 4 doses may be consecutive or non-consecutive days. In another embodiment, the methods may include a dosing regimen that allows for administration of the tablet to be delayed for 24 hours in two separate times within one day daily dosing regimen. In a specific embodiment, the methods may include administering a pharmaceutical composition that further allows during a 28 day daily dosing regimen for the patient to skip up to two non-consecutive days of a POC, provided the POC skipped dose is taken within about 24 hrs after the up to two skipped non-consecutive days. In another embodiment, the methods may allow for the administration of a POC that allows for the 24/4 regimen and the up to two delayed non-consecutive days regimen. In another specific embodiment, the POC may be drospirenone.

The present invention may also comprise methods for sizing drospirenone to a particular particle size. To obtain drospirenone in a particle form having the specific surface area and/or the particle size distribution as described above, one skilled in the art may use well-known methods in the art such as a milling process optionally combined with a sieve process. In a specific embodiment, the methods may comprise sizing drospirenone to a d50 particle size which may, in a specific embodiment, range from about 10 μm to about 60 In a specific embodiment, the methods may comprise:
  (i) sizing drospirenone to a d50 particle size which ranges from about 10 μm to about 60 μm by subjecting said drospirenone to one or mills selected from the group consisting of a ball mill, a hammer mill, a fluid energy mill, a rod mill, a cutting mill and an oscillating granulator.

The methods of the present invention may adjust the parameters of the milling and sieve steps by routine experiments to obtain the appropriate particle form of drospirenone. Appropriate mills which may be used include a fluid energy mill, a ball mill or rod mill, a hammer mill, a cutting mill and an oscillating granulator.

An appropriate particle form of a POC, such as drospirenone, may also be prepared by a crystallisation or precipitation process optionally combined with a sieve step in order to fully control the size of POC/drospirenone particles. For example, the precipitation process may comprise the steps of (i) dissolving drospirenone in a water-miscible solvent and then (ii) dispersing the resulting solution in cold water under stirring so that to induce the precipitation of drospirenone. The drospirenone particles may be then recovered by a filtration process.

The water-miscible solvents may be a solvent commonly used in crystallisation or precipitation process such as methanol, ethanol, isopropanol, dimethylformamide, tetrahydrofuran, dioxane or dimethyl sulfoxide, dimethylacetamide or acetone.

Such a process enables one skilled in the art to obtain a POC, such as drospirenone, essentially in a crystallized form.

By routine experiments, one skilled in the art may determine the parameters of the precipitation process to be used so as to obtain the appropriate form of drospirenone. One skilled in the art may adjust the parameters of the said precipitation process (such as the amounts of solvent, of water and optionally that of surfactant to be used) by routine experiments.

3. Contraceptive Kits

The present invention also provides contraceptive kits based on the contraceptive compositions as fully-described in the present application. Such a kit is particularly suitable for use in the contraceptive methods as described above.

The said contraceptive kits may comprise one or more packaging units. One or more packaging units may include, without being limited to, 1 packaging unit, 2 packaging units, 3 packaging units, 4 packaging units, 5 packaging units and 6 packaging units or more.

Each packaging unit may comprise from 21 to 28 daily active dosage units. As fully described above, each daily active dosage unit may include a contraceptive composition of the invention.

In some embodiments, the contraceptive kit may comprise one or more packaging units wherein each packaging unit comprises 21 to 28 daily active dosage units and wherein each daily active dosage unit comprises drospirenone in a non-micronized particle form such that:
  (i) no more than 50% of the drospirenone initially present in the said daily active dosage unit is dissolved within 30 minutes; and
  (ii) at least 50% of the said drospirenone is dissolved in a time range from 3 hours to 4 hours when the daily active dosage unit is subjected to an in vitro dissolution test, the percentages of drospirenone being related to the amount of drospirenone initially present in the said daily active dosage unit In one embodiment, the contraceptive kit may comprise one or more packaging units wherein each packaging unit comprises 21 to 28 daily active dosage units and wherein the oral administration of a daily active dosage unit provides a pharmacokinetic profile for an active drug characterized by one or more of the following features:
  (i) a mean $t_{max}$ of at least about 2.2 h and
  (ii) a mean $C_{max}$ which is less than about 30 ng/ml.

In some embodiments, the oral administration of the said daily active dosage unit provides a pharmacokinetic profile that may further be characterized by a mean $AUC_{0\ h\text{-}tlast}$ of at least 300 ng*ml/h, more preferably of at least 350 ng*ml/h. In another specific embodiment, the mean $t_{max}$ may range from about 2.2 hrs to about 6 hrs. In another embodiment, the $C_{max}$ may range from about 15 ng/ml to about 30 ng/ml.

In another specific embodiment, the active drug may be an active contraceptive drug. In another specific embodiment, the active contraceptive drug may be a POC. In another specific embodiment, the POC may be selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest. In one specific embodiment, the POC may be drospirenone.

In a specific embodiment, the contraceptive kits may comprise one or more packaging units wherein each packaging unit comprises 21 to 28 daily active dosage units and wherein the oral administration of a daily active dosage unit provides a pharmacokinetic profile for DRSP characterized by one or more of the following features:

(iii) a mean $t_{max}$ of at least about 2.2 h and
(iv) a mean $c_{max}$ which is less than about 30 ng/ml.

In some embodiments, the oral administration of the daily active dosage unit provides a pharmacokinetic profile further characterized by a mean $AUC_{0\ h\text{-}tlast}$ of at least 300 ng*ml/h, more preferably of at least 350 ng*ml/h. In another specific embodiment, the mean $t_{max}$ may range from about 2.2 hrs to about 6 hrs. In another embodiment, the $C_{max}$ may range from about 15 ng/ml to about 30 ng/ml.

As fully described above, in a specific embodiment, the daily active dosage units do not comprise any estrogen or estrogen derivative such as ethinyl estradiol, mestranol or 8-prenylnaringenin. In other words, the DRSP may be present in the daily active dosage units without estrogen.

In more embodiments, DRSP is the sole contraceptive ingredient comprised within the daily active dosage units. In some other embodiments, the contraceptive kit may comprise one or more packaging units wherein each packaging unit comprises 21 to 28 daily active dosage units and wherein:

(a) the amount of the drospirenone in each daily active dosage unit is at least 2 mg, without estrogen, and
(b) the oral administration of a daily active dosage unit provides a pharmacokinetic profile for DRSP characterized by the following features:
(i) a mean $t_{max}$, ranges from 2.2 h to 6 h and
(ii) a mean $C_{max}$ which is less than about 30 ng/ml.

In other embodiments, the contraceptive kit comprises one or more packaging units wherein each packaging unit comprises 21 to 28 daily active dosage units and wherein (a) the amount of drospirenone in each daily active dosage unit is at least 2 mg without estrogen; and
(b) each daily active dosage unit comprises drospirenone in a form such that:
(i) no more than 50% of the drospirenone initially present in the said daily active dosage unit is dissolved within 30 minutes; and
(ii) at least 50% of the said drospirenone is dissolved in a time range from 3 hours to 4 hours,
when the daily active dosage unit is subjected to an in vitro dissolution test according to the USP XXIII Paddle Method, the percentages of drospirenone being related to the amount of drospirenone initially present in the said daily active dosage unit.

Each packaging unit may optionally comprise from 1 to 7 daily dosage units of a pharmaceutically acceptable placebo. In some embodiments, the contraceptive kit may be designed so that each packaging unit comprises 28 daily dosage units and no daily dosage unit of a pharmaceutically acceptable placebo. Such a contraceptive kit is particularly appropriate to perform the contraceptive method of the invention which includes administering "continuously" DRSP without a free-contraceptive period.

In other embodiments, each packaging unit may comprise:

21 to 27 active daily dosage units consisting of a contraceptive composition as fully described in the present application; and
optionally, 1 to 7 daily dosage units of a pharmaceutically acceptable placebo.

Such a contraceptive kit is particularly appropriate to perform the contraceptive method of the invention which comprises:

a first phase wherein active daily dosage units of the invention which do not comprise estrogen are administered to the female patient over a period of 21 to 27 consecutive days followed by
a second phase wherein no contraceptive composition is administered to the female patient over a period of 1 to 7 consecutive days.

In some other embodiments, each packaging unit of the kit comprises 24 daily dosage units comprising an effective amount of a contraceptive composition as described herein and, optionally, 4 daily dosage units of a pharmaceutically acceptable placebo.

In a specific embodiment, the kits of the present invention may comprise one or more packaging units for a 24/4 dosing regimen. In a specific embodiment, the kits may comprise one or more packaging units wherein each packaging unit may comprise up to 28 daily active daily dosage units comprising an active contraceptive drug in a pharmaceutical composition, wherein the pharmaceutical composition allows for a 28 day daily dosing regimen, and wherein after initial administration of the active contraceptive drug has established its contraceptive effect in a patient, the patient may skip up to 4 doses within any 28 day daily dosing regimen period. In another embodiment, the skipped up to 4 doses may be on consecutive or non-consecutive days. In another embodiment, the kits may include packaging units that comprises a dosing regimen that allows for administration of the tablet to be delayed for 24 hours in two separate times within one 28 day daily dosing regimen period. In a specific embodiment, the kits may allow for administering a pharmaceutical composition that further allows during a 28 day daily dosing regimen for the patient to skip up to two non-consecutive days of an active contraceptive drug, provided the an active contraceptive drug skipped dose is taken within about 24 hrs after the up to two skipped non-consecutive days. In another embodiment, the kits may comprise a composition for administration of an active contraceptive drug that allows for the 24/4 regimen and the up to two delayed non-consecutive days regimen. In another specific embodiment, the active contraceptive drug may inhibit ovulation. In another specific embodiment, the contraceptive effect may comprise inhibiting ovulation.

In another specific embodiment, the kits may comprise one or more packaging units wherein each packaging unit may comprise up to 28 daily active daily dosage units comprising a POC for inhibiting ovulation, wherein the pharmaceutical composition allows for a 28 day daily dosing regimen, and wherein after initial administration of the POC has inhibited ovulation in a patient, the patient may skip up to 4 doses within any 28 day daily dosing regimen period. In another embodiment, the skipped up to 4 doses may be on consecutive or non-consecutive days. In another embodiment, the kits may include packaging units that comprises a dosing regimen that allows for administration of the tablet to be delayed for 24 hours in two separate times within one 28 day daily dosing regimen period. In a specific embodiment, the kits may allow for administering a pharmaceutical composition that further allows during a 28 day daily dosing regimen for the patient to skip up to two non-consecutive days of a POC, provided the POC skipped dose is taken within about 24 hrs after the up to two skipped non-consecutive days. In another embodiment, the kits may comprise a composition for administration of a POC that allows for the 24/4 regimen and the up to two delayed non-consecutive days regimen. In another specific embodiment, the POC may be drospirenone.

The packaging units as described above may have one of the conventional forms usually used for oral contraceptives. For example, the packaging unit may be a conventional blister pack comprising the appropriate number of dosage units in a sealed blister pack with a cardboard, paperboard, foil or plastic backing and enclosed in a suitable cover. Each blister container may be conveniently numbered or marked in order to facilitate compliance.

The packaging unit may contain daily dosage units in the order in which they are to be taken, i.e. starting with the first of the at least 21 dosage units that contain the combination of drospirenone optionally followed by 7 or less empty blisters, or by 7 or less dosage units comprising a pharmaceutically acceptable placebo.

The kit of the invention may comprise other appropriate components such as instructions for use.

The following examples are illustrative and are not intended to limit the scope of the invention as claimed.

EXAMPLES

Example 1

Preparation of Tablets a. Preparation of Drospirenone

Drospirenone was prepared according to a process similar to that described in WO2006/061309. In order to obtain DRSP with an appropriate particle size distribution, DRSP was subjected to an additional process of precipitation as mentioned in the present application.

Five batches of DRSP were prepared by variants of the above-mentioned precipitation process.

The analysis of the particle size distribution of each batch was performed by laser diffraction method in wet dispersion (Helos sensor, Sympatec with the wet disperser Quixel). The dispersant used was water. The full particle dispersion was ensured by ultrasonication.

The specific area was determined by the BET method. The results obtained are shown in table 1 below.

TABLE 1 particle size distribution parameters and specific area of DRSP batches

| | DRSP Batch | | | | |
|---|---|---|---|---|---|
| | PR100003 | 080169 | 080204 | 080257 | 080053 |
| d50 (µm) | 22.4 | 24.5 | 13.1 | 12.6 | 19.8 |
| d90 (µm) | 37.4 | 37.1 | 24.8 | 23.4 | 34.2 |
| d10 (µm) | 5.9 | 2.9 | 4.4 | 5.3 | 7.2 |
| d99 (µm) | 56.1 | 48.9 | 34.5 | 35.3 | 44.8 |
| Specific area (m²/g) | 0.26 | 0.45 | 0.83 | 0.77 | 0.63 |

The cumulative distribution function and the probability density function for batch 080053 are shown in FIG. 1.

b. Preparation of Tablets According to the Present Invention

The tablets are prepared by direct compression. The composition of tablets is described hereunder.

TABLE 2 composition of tablets (A-3mg, inventive)

| Material | mg/tablet | (%) |
|---|---|---|
| Drospirenone (Batch 080053) | 3.00 | 4.74 |
| Microcrystalline cellulose 102 | 36.48 | 57.60 |
| Anhydrous lactose DCL21 | 20.16 | 31.83 |

TABLE 2-continued composition of tablets (A-3mg, inventive)

| Material | mg/tablet | (%) |
|---|---|---|
| Silicon dioxide | 3.36 | 5.31 |
| Magnesium stearate | 0.33 | 0.53 |
| TOTAL | 63.33 | 100.00 |

Example 2

In Vitro Dissolution Profiles a. Comparison of Tablets A-3 mg (DRSP) with Yasminelle® (Comparative)

The rate of dissolution of drospirenone from the tablets prepared in Example 1 (A-3 mg) was determined by the USP XXIII Paddle Method using a USP Dissolution Test Apparatus 2 including 6 covered glass vessels and 6 paddles.

Tablets were placed in 900 ml water at a temperature of 37° C.±(0.5° C.) and stirred at 50 rpm. The amount of drospirenone released in water was measured over several hours. The mean percentages of DRSP released (which were related to the amount of drospirenone initially present in the each tablet) were calculated and plotted versus time in order to provide the in vitro dissolution profile of DRSP.

Figure 2:
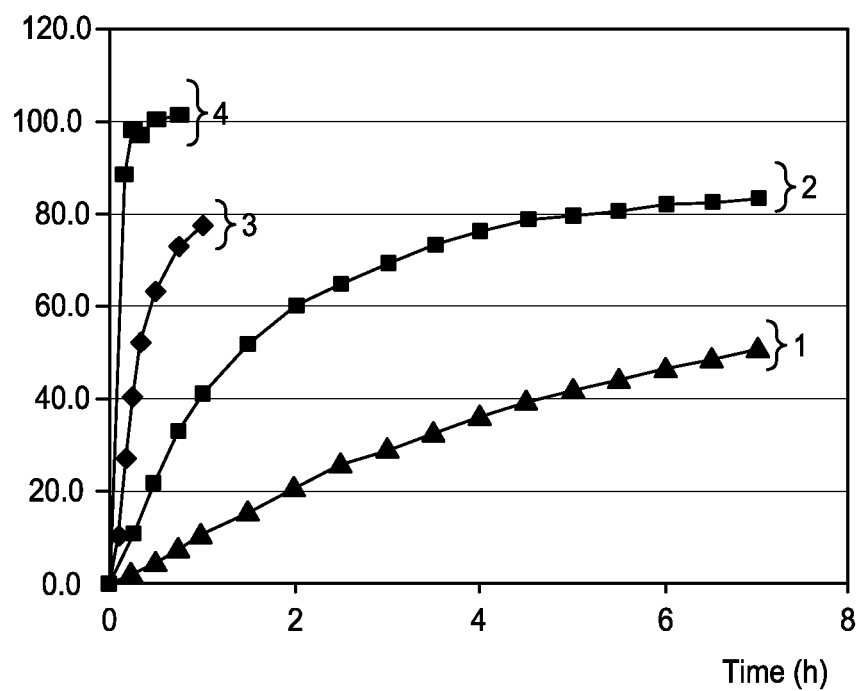
FIG. 2: In Vitro Dissolution Profiles

The in vitro dissolution profile of tablets A-3 mg (inventive) is shown in FIG. 2 (see curve no 2).

FIG. 2 also provides the dissolution profile obtained for Yasminelle®—tablets which comprised micronized DRSP (comparative) (see curve no 4).

Surprisingly, the initial dissolution rate for tablets obtained in Example 1 (A-3 mg) was significantly reduced as compared to that of the Yasminelle® tablet since only about 22% of DRSP initially present in the tablets was released within 30 min (versus almost 100% for Yasminelle® in 30 min). The final dissolution percentage of DRSP from tablets obtained in Example 1 was more than 80%. As described in Example 3, Part 1, such an in vitro dissolution profile is correlated with a different and improved pharmacokinetic profile as compared to Yasminelle®.

b. Examples of Other In Vitro Dissolution Profiles

In order to illustrate the correlation between the in vitro dissolution profile of drospirenone and its pharmacokinetic profile upon oral administration, two other types of DRSP-containing tablets (comparative) were prepared. The composition of these tablets is distinct from that of tablet A-3 mg. Each tablet comprises 3 mg of DRSP in a non-micronized form.

The first type of tablet (CO1-3 mg) provides a rapid dissolution in vitro since about 60% of DRSP initially present in tablets were released within 30 min according to the USP XXIII Paddle Method (see curve no 3, FIG. 2).

The second type of tablet (CO2-3 mg) displays a very low dissolution rate of DRSP in vitro. No more than of 5% of DRSP initially present in tablets were released within 30 min and no more than about 40% of the said DRSP was dissolved within 4 hours (see curve no 1, FIG. 2).

Example 3

Pharmacokinetic Studies

Part 1: Evaluation of the Pharmacokinetics Parameters for the Composition According to the Invention (Tablet A-3 mg) as Compared to Yasminelle®

Objectives:

The main objective of the present trial was to assess the bioavailability of an oral test preparation containing drospirenone at 3.0 mg (tablets described in Example 1 obtained from batch 080053 (i.e. A-3 mg), called hereunder "test product" hereunder) as compared to a market standard (Yasminelle Schering AG, called hereunder "reference product") after oral administration of a single dose of drospirenone at 3.0 mg under fasting conditions in two different periods, 7 days apart. Yasminelle® comprises 3.0 mg DRSP in micronized form and 0.030 mg of ethinylestradiol.

In order to investigate the relative bioavailability of the products, the 90% confidence intervals for the intra-individual ratios (test vs. reference) for the endpoint(s) ($AUC_{0\text{-}tlast}$ and $C_{max}$ of drospirenone) were determined.

The secondary objective of the present trial was to investigate the safety of both preparations on the basis of safety clinical and laboratory examinations (at the beginning and at the end of the trial) and registration of adverse events and/or adverse drug reactions.

Methodology:

The study was conducted as a monocentric, open, randomized, single-dose, two-period crossover trial in healthy female volunteers, with duration of hospitalization of approximately 12 h-13 h after dosing on day 1 and with a real wash-out period of 7 days.

| | |
|---|---|
| Subjects (planned and analyzed): | - planned for completion: 10<br>- enrolled: 19<br>- screened only: 5<br>- randomized: 14<br>- drop-outs: 0<br>- completed as per protocol: 14<br>- data set for pharmacokinetic analysis: 14<br>- data set for statistical analysis: 14<br>- data set for safety analysis: 14 |
| Diagnosis and main criteria for inclusion: | [1] female Caucasian<br>[2] age between 18 and 40 years<br>[3] physically and mentally healthy as judged by means of a medical, standard laboratory and gynecological examination<br>[4] non-smokers since at least 6 months (confirmed by urine cotinine test)<br>[5] use of an effective non-hormonal method of contraception<br>List of accepted contraceptive methods<br>- combination of two barrier methods (female/male condoms, diaphragms, spermicides)<br>- intrauterine device (inert or copper-releasing IUD)<br>- existing sterilization (female tubal occlusion) |

Duration of Treatment:

Each volunteer received in a random way an oral single dose of 1 tablet of the test product or 1 of the reference drug on two single occasions, always under fasting conditions. Both study periods were separated by a real wash-out phase of at least 7 days.

Blood Sampling Points in Each Study Period:

Pre-dose, and 0:30, 1:00, 1:30, 2:00, 3:00, 4:00, 5:00, 6:00, 8:00, 12:00, 24:00, 48:00 and 72:00 hours post dosing with separation of plasma. For each endpoint, the quantification of DRSP in plasma was performed according to an analytical method adapted from Kirk et al., (*Rapid Communications in mass Spectrometry*, 2006, 20:1247-1252). Briefly, Drospirenone was extracted from human EDTA plasma using a solid-phase extraction procedure with HLB 60 mg Oasis cartridges and afterwards derivatized with Girard-P solution, then injected into a liquid chromatograph equipped with a tandem mass spectrometry detector. This method enables the determination of drospirenone in human EDTA plasma over the range 0.25 to 100.40 ng/mL.

Criteria for Evaluation:

Pharmacokinetics:
  Primary endpoints: $AUC_{0\text{-}tlast}$ and $C_{max}$ of drospirenone
  Secondary endpoint: $t_{max}$ of drospirenone
  Additional endpoints: not planned Safety
  Adverse events, clinical and laboratory screening parameters.

Statistical Methods:
For Pharmacokinetic Endpoints:
  parametric method (ANOVA-log) for $AUC_{0\text{-}tlast}$ and $C_{max}$ of drospirenone
  covariates in the model: sequence, treatment, period, volunteer within sequence
  non-parametric method (Hauschke et al. 1990) $t_{max}$ of drospirenone
  90% confidence interval for the ratios (test vs. reference) for $AUC_{0\text{-}tlast}$ and $C_{max}$ of drospirenone For Evaluation of Safety:
  descriptive statistical evaluation only.

Bioavailability:

The 90% confidence intervals of log-transformed values were calculated for the intra-individual ratio test vs. reference for AUC0-tlast and $C_{max}$ of drospirenone (and then only interpreted in a descriptive way, and not compared with the usual acceptance ranges for the respective parameters (CPMP/EWP/QWP/1401/98, July 2001) as the current trial did not have the aim of proving bioequivalence). The 90% confidence interval was calculated for the intra-individual ratio for the difference of $t_{max}$ (test-reference) and descriptively assessed.

Results

Pharmacokinetics:

A total number of 14 volunteers completed the trial according to the protocol. The samples of 14 volunteers were analyzed and 14 volunteers were subjected to statistical evaluation. The endpoints of the analysis of drospirenone after an oral single dose of 1 tablet (drospirenone 3.0 mg) of the test preparation or 1 film-coated tablet (0.03 mg ethinyl estradiol and 3 mg drospirenone) of the reference product of the 14 volunteers who were subject to pharmacokinetic and statistical evaluation are summarized in table 3 hereunder.

TABLE 3

Pharmacokinetic endpoints (primary, secondary, and additional) of drospirenone for test product (TEST) and reference product (REFERENCE).

TEST (N = 14)

| Variable | geom.mean | arithm.mean | SD | CV | Range | median |
|---|---|---|---|---|---|---|
| AUC0-tlast [ng*h/ml−] | 360.96 | 368.55 | 75.83 | 20.6 | 234.72-482.91 | 359.33 |
| AUC0-inf [ng*h/ml−] | 452.93 | 462.00 | 93.26 | 20.2 | 312.60-624.12 | 463.65 |
| AUCres [%] | 19.12 | 20.04 | 6.62 | 33.0 | | 17.70 |
| Cmax [ng/mL] | 16.46 | 17.36 | 5.50 | 31.6 | 12.13-33.70 6.39-27.79 | 17.41 |
| tmax | — | 3.57 | 1.01 | 28.3 | 2.00-5.00 | 3.50 |
| MRT [h] | — | 44.08 | 9.69 | 22.0 | 33.64-64.18 | 40.89 |
| $t^{1/2}$ [h] | — | 31.87 | 6.29 | 19.7 | 24.59-44.43 | 29.42 |

REFERENCE (N = 14)

| Variable | geom.mean | arithm.mean | SD | CV | Range | median |
|---|---|---|---|---|---|---|
| AUC0-tlast [ng*h/mL] | 414.60 | 418.58 | 60.46 | 14.4 | 337.80-527.81 | 397.70 |
| AUC0-inf [ng*h/mL] | 503.65 | 509.25 | 77.76 | 15.3 | 386.08-654.48 | 510.74 |
| AUCres [%] | 17.12 | 17.58 | 4.18 | 23.8 | 11.19-27.61 | 18.47 |
| Cmax [ng/mL] | 34.91 | 35.43 | 6.32 | 17.8 | 24.30-45.96 | 35.24 |
| tmax | | 1.57 | 0.55 | 35.0 | 1.00-3.00 | 1.50 |
| MRT [h] | | 38.81 | 6.45 | 16.6 | 29.68-56.00 | 39.39 |
| $t^{1/2}$ [h]] | | 29.78 | 4.41 | 14.8 | 25.21-43.30 | 28.47 |

The 90% confidence intervals for the intra-individual ratios (test/reference) for $AUC_{0-tlast}$ and $C_{max}$ of drospirenone, as well as differences (test-reference) for $t_{max}$ of drospirenone are presented in table 4 hereunder.

TABLE 4

90% confidence intervals of drospirenone

| Variable | Point estimator | confidence limits*** | ANOVA- (%) |
|---|---|---|---|
| AUC0-tlast (ratio test/reference) | 0.8706* | 0.8081-0.9380* | 11.1% |
| Cmax (ratio test/reference) | 0.4715* | 0.3930-0.5658* | 27.6% |
| tmax [h] (difference test-reference) | 1.7650** | 1.5000-2.5000** | |

Figure 3A:
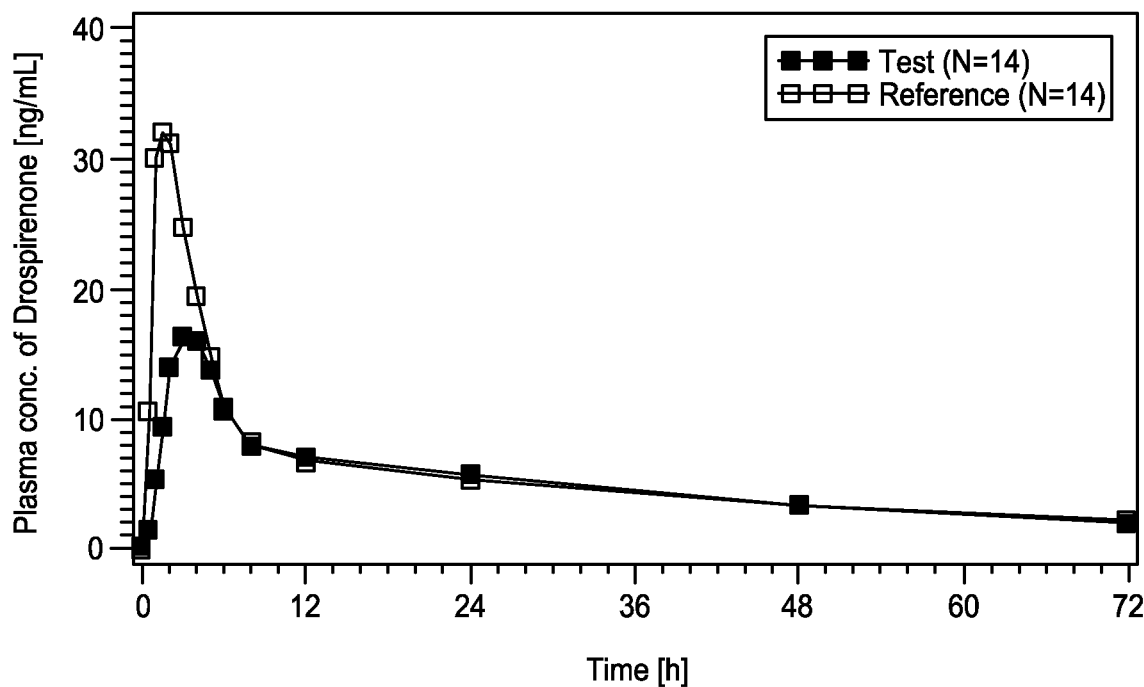
FIG. 3a and FIG. 3b: Mean Drospirenone Serum Concentration Versus Time Curves

*parametric confidence interval
**non-parametric confidence interval
14 volunteers subjected to statistical evaluation The concentration-time curves of drospirenone after administration of an oral single dose of 1 tablet of the test preparation and tablet of the reference product are to be found in FIG. 3a for both preparations (arithmetic means).

The evaluation of bioavailability of the primary endpoints $AUC_{0-tlast}$ and $C_{max}$ of drospirenone was based on a parametric method (ANOVA-log).

The 90%-confidence interval calculated by means of ANOVA-log for the first primary endpoint, intra-individual ratio (T/R) of $AUC_{0-tlast}$ of was between 0.8081 and 0.9380. The 90%-confidence interval calculated by means of ANOVAlog for the second primary endpoint intra-individual ratio (T/R) of $C_{max}$ of drospirenone was between 0.3930 and 0.5658. The secondary endpoint $t_{max}$ the 90%-confidence interval for the intra-individual differences was between 1.5000 and 2.5000 hours. The point estimator for the difference of $t_{max}$ of drospirenone was 106 minutes (the concentration maxima after administration of the test preparation being observed later).

It is well known in the art that drospirenone isomerizes into a biologically inactive isomer in acidic conditions, including in the acidic conditions that are encountered in the human stomach.

When conducting the present pharmacokinetics study, assays for detecting the eventual presence of the inactive isomer of drospirenone in the plasma of the treated women have been performed. The results have shown that the amount of inactive isomer of drospirenone in the plasma samples collected from the clinically tested women subjects was below the detectable level (<1 ng/ml), which means that the pharmaceutical composition that has been used is adapted to release the full amount of drospirenone in its biologically active form to the target organs.

Safety:

The test formulation and the reference drug were well tolerated. Seventeen non-serious adverse events (AEs) were registered in 11 subjects in the course of the trial:

nine AEs were observed in 8 subjects after administration of test product eight AEs were observed in 7 subjects after administration of reference drug.

All adverse events were assessed as not serious. All adverse events were assessed as possibly related by the investigator. All AEs resolved completely within relative short frame time. The results of laboratory screening gave no indications for adverse events or adverse drug reactions.

CONCLUSIONS

Based on the $AUC_{0-tlast}$ of drospirenone, the extent of absorption of the test product is similar to that of the reference product but the rate of absorption is significantly delayed resulting in an increased $t_{max}$ and decreased $C_{max}$. The tolerability of test product and the reference product was similarly good.

Part 2: Evaluation of Other Comparative Tablets CO1-3 mg and CO2-3 mg as Compared to Yasminelle®

The main objective of this second trial was to further illustrate the correlation between in vitro dissolution profile and pharmacokinetics parameters for oral tablets comprising DRSP. The oral test tablets were tablet CO1-3 mg and tablet CO2-3 mg which display a rapid in vitro dissolution rate for DRSP and a very slow dissolution rate for DRSP, respectively (see Example 2b).

The reference product was Yasminelle®. The methodology for this second trial was similar to that of the trial described in part 1 hereabove.

Briefly, the bioavailability of two oral test preparations (namely CO1-3 mg and CO2-3 mg) as compared to that of the market standard (Yasminelle®, Schering AG) was assessed after oral administration of a single tablet in each case (corresponding to 3 mg of DRSP) under fasting conditions in three different periods, 7 days apart. In order to investigate the relative bioavailability of the products, the 90% confidence intervals for the intraindividual ratios (CO1-3 mg vs. reference product and CO2-3 mg vs. reference product) for the endpoint(s) ($AUC_{0-tlast}$ and $C_{max}$ of drospirenone) was determined.

The study was conducted as a monocentric, open, randomized, single-dose, three-period crossover trial in healthy female volunteers, with a duration of hospitalization of approximately 12 h-13 h after dosing.

Each volunteer received randomly an oral single dose of drospirenone 3.0 mg (either 1 test tablet CO1-3 mg or 1 test tablet CO2-3 mg or 1 film-coated tablet of Yasminelle®) on three single occasions under fasting conditions.

The three study periods were separated by a real wash-out phase of between 7 days and 10 days.

| Subjects (planned and analyzed): | - planned for completion: 10<br>- enrolled: 18<br>- screened only: 4<br>- randomized: 14<br>- drop-outs: 0<br>- completed as per protocol: 14<br>- data set for pharmacokinetic analysis: 14<br>- data set for statistical analysis: 14<br>- data set for safety analysis: 14 |
|---|---|

Results

Figure 3B:
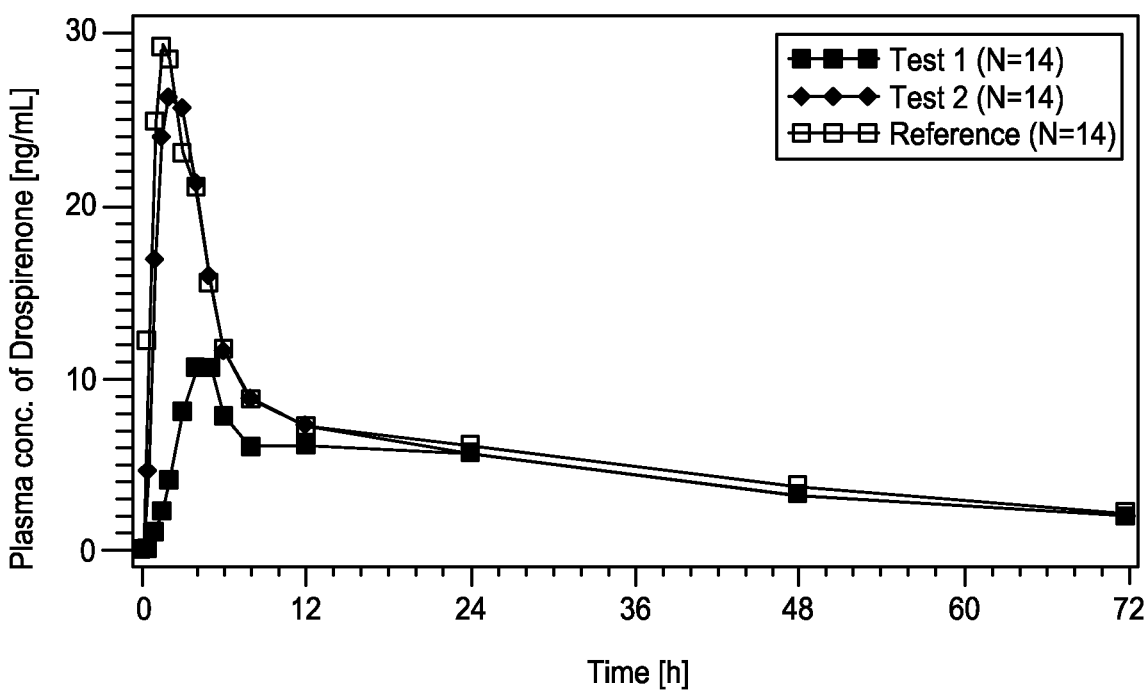

The concentration-time curves of drospirenone after administration of an oral single dose of 1 tablet of each product (namely, CO1-3 mg, CO2-3 mg and Yasminelle®) are in FIG. 3b (arithmetic means). As a reminder, CO1-3 mg displayed a rapid dissolution rate for DRSP in vitro (about 60% within 30 min). The pharmacokinetic profile obtained for CO1-3 mg is very close to that of Yasminelle® except for the $C_{max}$. Interestingly, the mean $C_{max}$ of CO1-3 mg was 30 ng/ml versus 36 ng/ml for Yasminelle®. The $AUC_{0\ h-tlast}$ for CO1-3 mg was similar to that of Yasminelle® (410.58 ng*h/ml versus 440.14 ng*h/ml).

On the other hand, CO2-3 mg surprisingly displays a very low dissolution rate of DRSP in vitro since no more than of 5% of DRSP initially present in tablets were released within 30 min and no more than about 40% of the said DRSP was dissolved within 4 hours. The composition displays a reduced $C_{max}$ and a delayed $t_{max}$ as compared to Yasminelle®. However, the mean AUC of said composition was low.

These pharmacokinetics results combined with in vitro results described in Example 2 illustrate the correlation between the in vitro dissolution rate of DRSP and its pharmacokinetics profile (in particular for $C_{max}$ and $t_{max}$), upon oral administration.

Example 4

Simulation Curves Based on Experimental Data Obtained in the Clinical Trial Described in Example 3, Part 1

The DRSP mean plasma concentration versus time curves, which is expected to be obtained from the oral administration of one tablet described in table 2 but containing 4 mg of DRSP from batch 80053 (namely, A-4 mg), was extrapolated from experimental data obtained in the clinical trial described in Example 3 with the assumption that the DRSP plasma concentration is proportional to the administered oral amount of DRSP.

Figure 4A:
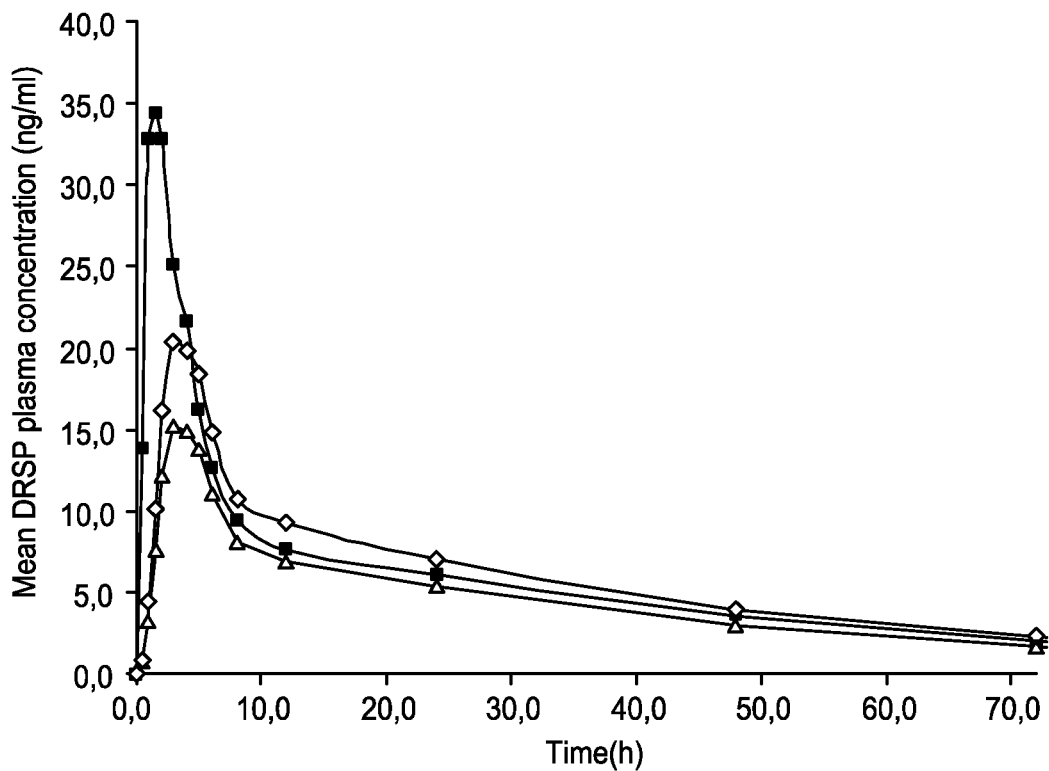
FIGS. 4a, 4b and 4c: Simulation Based on Pharmacokinetic Results from Clinical Trial Described in Example 3

The resulting curve for tablet A-4 mg is shown in FIG. 3a and FIG. 4a and compared with that obtained with Yasminelle® and with the tablet A-3 mg described in table 2.

Figure 4B:
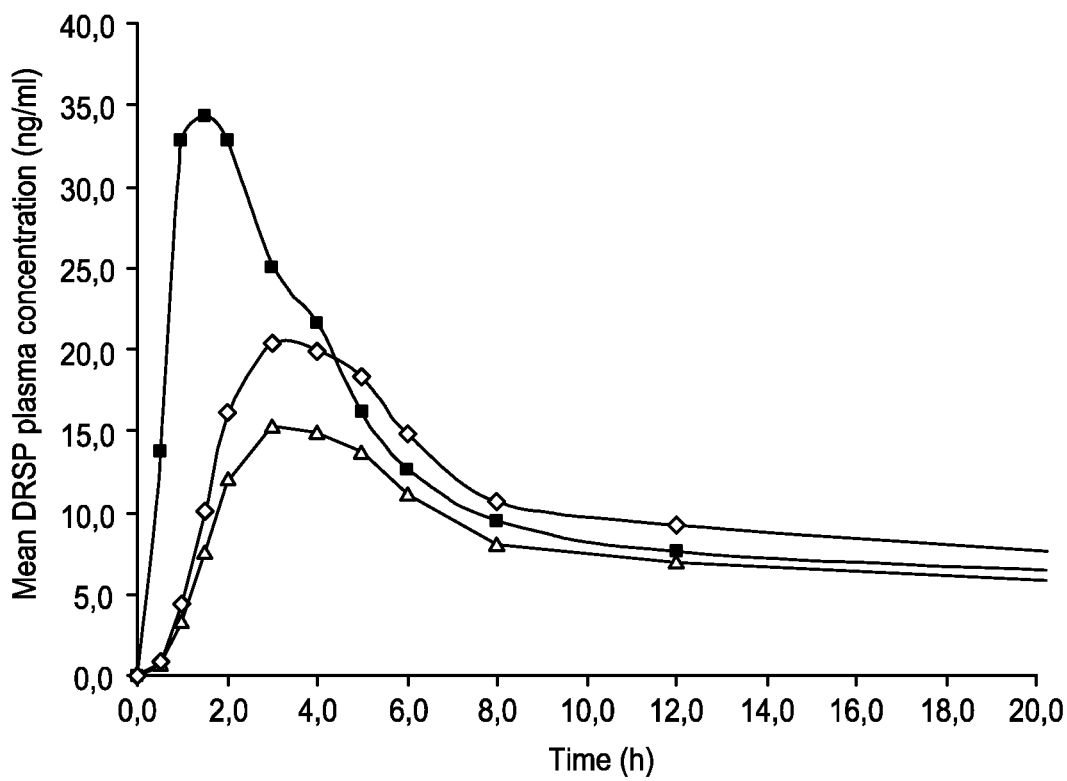

As illustrated in FIGS. 4a and 4b, increasing the DRSP amount from 3 mg to 4 mg in the tablet described in table 2 is expected not to modify the $t_{max}$, which may remain significantly delayed as compared to that of Yasminelle®. The $C_{max}$ is expected to be increased but to remain significantly lower than that of Yasminelle® (no more than 60% that of Yasminelle®). Interestingly, the mean plasma concentration is expected to be higher than that of Yasminelle® after the concentration peak.

Figure 4C:
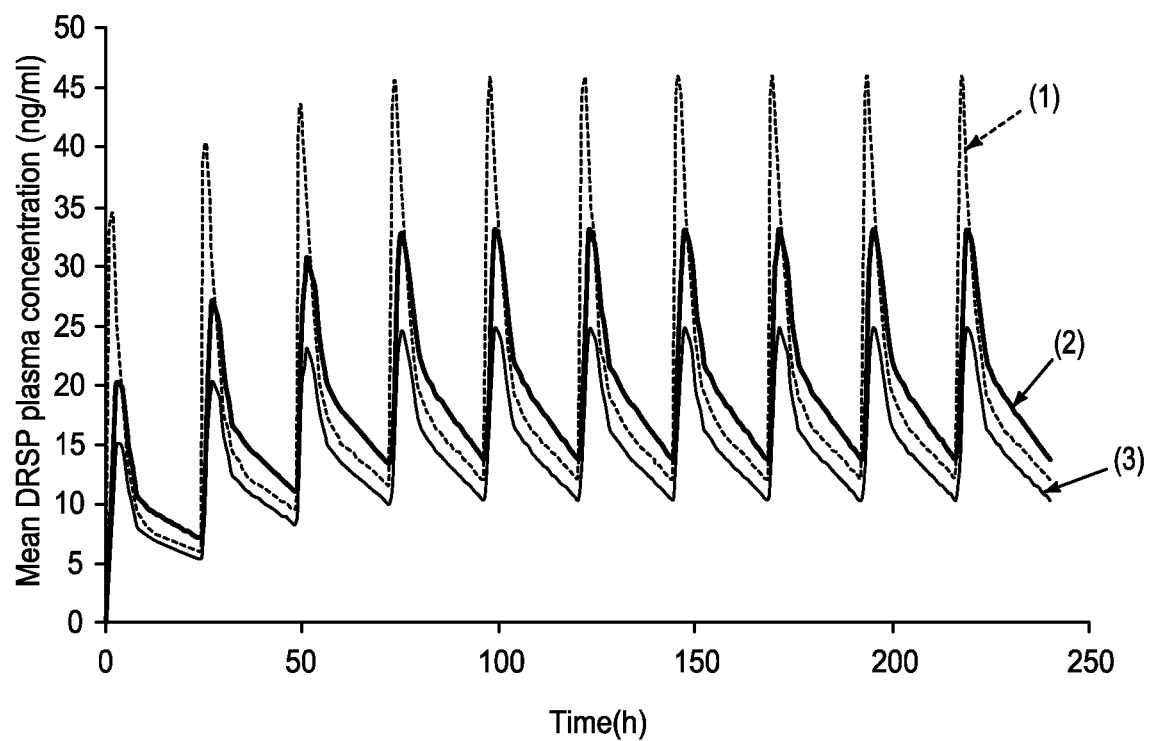

FIG. 4c shows the mean DRSP plasma concentration versus time curves which are expected to result from the repeated administration every 24 hours of one tablet of Yasminelle® (curve no 1), one tablet of A-3 mg (curve no 3) and one tablet of A-4 mg (curve n° 2).

The curves obtained for the compositions of the invention (namely curves n° 3 and no 2) show less difference between mean $C_{max}$ and mean C (minimal DRSP concentration) than the Yasminelle® composition. The repeated administration of the compositions of the invention thus provides a more stable DRSP plasma concentration with lower $C_{max}$ than Yasminelle®. Such a fact improves the bleeding profile and reduces the side effects of DRSP when the compositions of the invention are used as a contraceptive.

In the case of tablet A-4 mg, it should be noted that the mean plasma concentration is higher than that obtained of Yasminelle® for the time period between $t_{max}$ and the time of the next tablet intake, which provides a higher contraceptive reliability. Thus, Tablet A-4 mg is expected to be appropriate as a progestogen-only pill.

Example 5

Another Example of Composition According to the Invention

Part 1: In Vitro Dissolution Profile

Tablets (B-4 mg) were prepared as described in Example 1 from DRSP batch No PR100003. Each tablet comprises 4.0 mg of DRSP and excipients in a similar amount to that described in Table 1. The tablets (B-4 mg) were further coated with a suitable film-forming agent, as described in the specification.

Figure 5A:
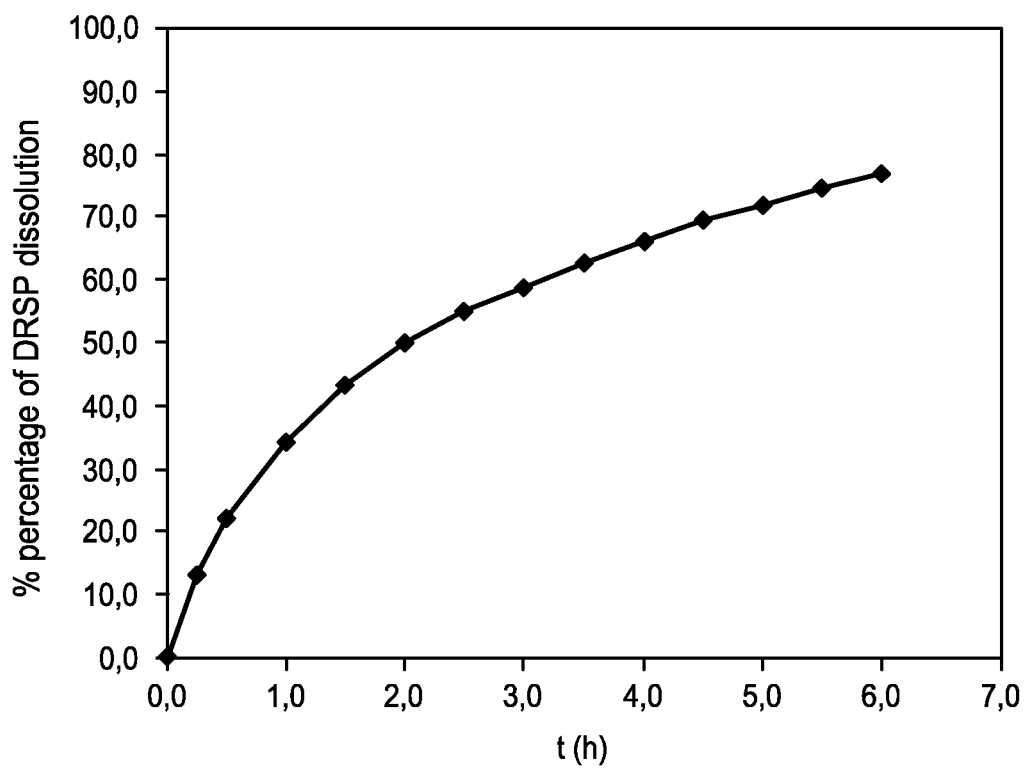
FIG. 5a and FIG. 5b: In Vitro Dissolution Profile and Mean Drospirenone Serum Concentration Versus Time Curve for Tablet Comprising 4 mg of DRSP (B-4 mg).

The resulting tablets were subjected to a dissolving in vitro test as described in Example 2. The mean in vitro dissolution profile of said tablets is shown in FIG. 5a.

The initial dissolution rate for DRSP was significantly reduced as compared to Yasminelle® since only about 22% of DRSP initially present in tablets were released within 30 min. However, about 66% and about 77% of DRSP initially present in tablets were released within 4 h and 6 h respectively.

The in vitro dissolution profile for tablets B-4 mg was similar to that of tablet A-3 mg (see example 1). Such a fact illustrates that the specific area of DRSP does not significantly impair its in vitro dissolution if the said DRSP displays appropriate d50, d90 and d10.

| Subjects (planned and analyzed): | - planned for completion: 10<br>-enrolled: 15<br>- screened only: 5<br>-randomized: 10<br>- drop-outs: 0<br>- completed as per protocol: 10<br>- data set for pharmacokinetic analysis: 10<br>- data set for statistical analysis: 10<br>- data set for safety analysis: 10 |
|---|---| b. Results

Yasminelle® and the test product were well-tolerated by all the patients.

Figure 5B:
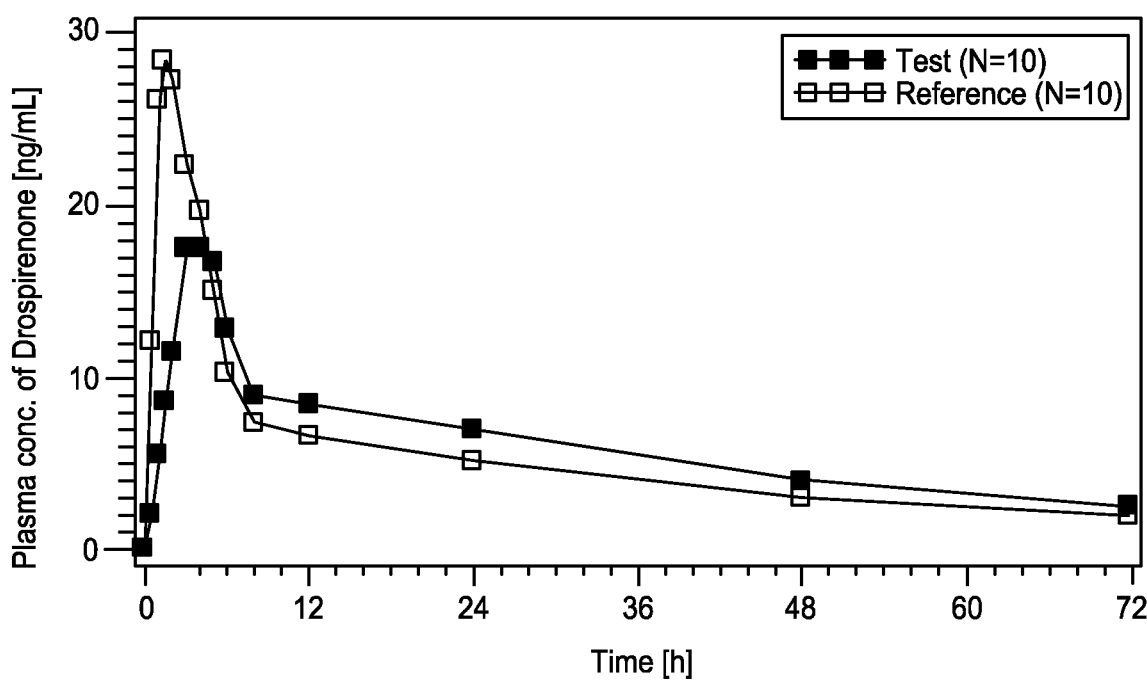

The concentration-time curves of drospirenone after administration of an oral single dose of 1 tablet of each product (namely, tablet B-4 mg and Yasminelle®) are to be found in FIG. 5b (arithmetic means). The results of said trial are further shown in table 5 hereunder.

TABLE 5

Pharmacokinetic endpoints of drospirenone for tablet B-4 mg (TEST) and Yasminelle ® (REFERENCE)

TEST (N = 10)

| Variable | geom.mean | arithm.mean | SD | CV | range | median |
|---|---|---|---|---|---|---|
| AUCO-tlast [ng*h/mL] | 428.07 | 438.85 | 104.53 | 23.8 | 320.74-634.58 | 419.05 |
| Cmax [ng/mL] | 18.96 | 19.81 | 6.14 | 31.0 | 12.42-30.17 | 19.40 |
| tmax [h] | — | 3.900 | 0.876 | 22.5 | 3.000-5.000 | 4.000 |

REFERENCE (N = 10)

| Variable | geom.mean | arithm.mean | SD | CV | range | median |
|---|---|---|---|---|---|---|
| AUCO-tlast [ng*h/mL] | 386.68 | 394.88 | 90.22 | 22.8 | 271.57-615.65 | 391.49 |
| Cmax [ngh/mL] | 32.52 | 32.85 | 4.85 | 14.8 | 23.97-42.80 | 33.39 |
| tmax [h] | — | 1.700 | 0.979 | 54.1 | 1.000-4.000 | 1.500 |

Part 2: Evaluation of the Pharmacokinetics Parameters for the Composition According to the Invention (Tablet B-4 mg) as Compared to Yasminelle® a. Methodology

The pharmacokinetics parameters for tablet B-4 mg were determined as described in Example 1, part 1.

Briefly, the bio availability of the test preparation (namely B-4 mg) as compared to that of the market standard (Yasminelle®, Schering AG) was assessed after oral administration of a single tablet in each case under fasting conditions in three different periods, 7 days apart.

The DRSP oral dose was 3 mg for Yasminelle® versus 4 mg for tablet B-4 mg (inventive). In order to investigate the relative bioavailability of the products, the 90% confidence intervals for the intraindividual ratios (B-4 mg versus Yasminelle®) for the endpoint(s) ($AUC_{0\text{-}tlast}$ and $C_{max}$ of drospirenone) were determined.

The study was conducted as a monocentric, open, randomized, single-dose, three-period crossover trial in healthy female volunteers, with duration of hospitalization of approximately 12 h-13 h after dosing.

Each volunteer randomly received an oral single dose of drospirenone (either one test tablet B-4 mg or one tablet of Yasminelle®) on two single occasions under fasting conditions. Both study periods were separated by a real wash-out phase of between 7 days and 10 days.

The pharmacokinetics profile for DRSP obtained after the oral administration of one tablet B-4 mg correlated with the DRSP pharmacokinetics profile expected on the basis of simulations (see Example 4).

The mean $t_{max}$ for tablet B-4 mg was significantly delayed as compared to that of Yasminelle® (3.9 h versus 1.7 h). Furthermore, the mean $C_{max}$ obtained for tablet B-4 mg was significantly lower than that of Yasminelle® (19.8 versus 32.9 ng*h/ml). The mean $C_{max}$ for tablet B-4 mg corresponded to about 58% of Yasminelle® $C_{max}$ whereas, in Example 1, the mean $C_{max}$ for tablet A-3 mg corresponded to 49% of that of Yasminelle®; the increase of DRSP dose in tablets did not induce a significant change in mean $C_{max}$ values.

On the other hand, the increase of DRSP dose significantly improved the mean $AUC_{0\ h\text{-}tlast}$ since the mean $AUC_{0\ h\text{-}tlast}$ for tablet B-4 mg was 111% of Yasminelle. In Example 1, the mean $AUC_{0\ h\text{-}tlast}$ for tablet A-3 mg was only 86% of that of Yaminelle®.

In other words, the present results clearly show that compositions of the invention allow for a high value of mean $AUC_{0\ h\text{-}tlast}$ combined with a low mean $C_{max}$ and a delayed mean $t_{max}$ for DRSP, as compared to Yasminelle®. The repeated administration of tablets B-4 mg every 24 hours will certainly provide a DRSP plasma concentration profile similar to that expected for tablet A-4 mg (see FIG. 4C, curve no 2).

Accordingly, the compositions of the present invention, such as tablet A-4 mg and tablet B-4 mg, are appropriate to be used as contraceptive-only pills. Such contraceptives have a good tolerance and to prevent the occurrence of side-effects related to high and fluctuated DRSP plasma concentrations.

Part 3: Evaluation of the Contraceptive Efficiency of the Pharmaceutical Composition According to the Invention The aim of the study is to illustrate that a contraceptive pill according to the invention which comprises DRSP as the sole contraceptive agent and which is administered upon a 24/4 regimen allows for the inhibition of ovulation even in the case of episodic delay of administering the pill.

The contraceptive pill is made of 24 tablets B-4 mg as defined in Example 5, Part 2 hereabove and 4 placebo tablets.

a. Methodology

The study was an open-label monocentric trial. Subjects eligible for the study were aged 20-30 years, had a body mass index <30 kg/m², regular menstrual cycles (at least 4 regular cycles in the past 6 months) and were willing to use condoms during the entire duration of the study. Excluded were subjects with a (suspected) pregnancy, active or past thromboembolic disorder, present or past severe hepatic disease, carcinoma of the endometrium or other known or suspected estrogen-dependent neoplasia, undiagnosed vaginal bleeding, use of liver enzyme-inducing drugs and other drugs.

A total of 20 women were enrolled in this trial and performed the two treatment cycles and the follow-up cycle.

Blood sampling for hormonal determination (progesterone, 17-beta-estradiol, FSH and LH) was performed every 3 days from day 1 to day 84 and assessments of weight, blood pressure and heart rate were performed at each visit. Serum progesterone, 17-beta-estradiol, FSH and LH concentrations were measured with validated commercial in vitro diagnostic kits (VIDAS, ELFA Biomerieux). Internal controls were included in each set of samples.

Two urine pregnancy tests were performed during the study:
at the visit on day 1 of the first cycle in order to verify the exclusion criterion "pregnant woman" just before starting the study treatment (the subject was to be excluded if this test was positive); and
at the visit on day 7 of the follow-up cycle.

The occurrence of ovulation during treatment was determined on the basis of serum progesterone concentration, using the criteria of Landgren et al. Thus, an ovulation was judged to have occurred in case of progesterone concentrations >5.04 ng/ml-sustained for at least 2 consecutive progesterone samples.

b. Results

FIGS. 6a and 6b show the plotted individual values for plasma progesterone levels and plasma estradiol levels, respectively. For all women, progesterone level values were systematically lower than 5.04 ng/ml during the entire treatment period (including placebo period). The maximum value of progesterone was observed to be 3 ng/mL for a sole woman and for only one time during the treatment periods (including placebo period).

These results surprisingly show that during the 2 cycles, no ovulation occurred. Conversely, upon cessation of treat-

TABLE 6

| Parameters of enrolled patients | | | | | | |
|---|---|---|---|---|---|---|
| | Age | Weight (kg) | BMI (Kg/m²) | Systolic blood pressure (mmHg) | Diastolic blood pressure (mmHg) | Heart rate (beats/mm) |
| Mean ± Std dev | 24.6 ± 2.4 | 60.28 ± 7.95 | 22.76 3.19 | 110.3 ± 10.3 | 64.1 ± 7.0 | 65.4 ± 5.7 |
| Median | 24.5 | 59.1 | 22.39 | 115.0 | 62.5 | 64.0 |
| Min, Max | 20;29 | 50.0;79.2 | 18.1;30.0 | 90;120 | 50;80 | 58;80 |

The subjects received daily treatment with tablets containing 4 mg DRSP with a 24/4 regimen during two cycles. The subjects started treatment on the 1st day of the cycle (i.e., the first day of onset of vaginal bleeding) following the screening visit. The subjects took one tablet of 4 mg DRSP from day 1 to day 24 and one placebo tablet from day 25 to day 28 of each treatment cycle at a fixed hour, with the exception of day 5 and day 13 of the second cycle. On these two days, the tablet intake was delayed for 24 hours (i.e., no pill was taken on day 5 and day 13 and a tablet was taken once on day 6 and once on day 14, respectively). The complete study consisted of a 56-day treatment period and a 28-day post-treatment follow-up period. After informed consent was obtained, the subjects underwent a gynecological examination and a general medical examination, including 12-lead ECG, hematology, biochemistry and urinalysis laboratory tests. After compliance with the eligibility criteria was confirmed, and after performing a urine pregnancy test with a negative result on the first day of onset of vaginal bleeding, the subject was included in the study and began taking the study medication.

ment, during the 28-day follow-up cycle, the progesterone levels increased above 5.04 ng/mL in 17 out of 20 women showing a return of ovulation. The minimum time to the first level of progesterone to be above 5.04 ng/mL was on day 15 after the last placebo tablet.

During the 2 cycles under treatment, the mean estradiol levels were significantly lower in comparison with those measured during the follow-up cycle. Noticeably, the secretion of estradiol is not totally inhibited during the treatment period.

To conclude, the data surprisingly demonstrate that the compositions of the invention, when used as a POC upon a 24/4 regimen, provided reliable inhibition of ovulation even in the presence of a placebo period. This ovulation inhibition was maintained even if the intake of the tablet was delayed for 24 hours in two separate times within one cycle. In view of these experimental data, the compositions of the present invention exhibit similar reliability and efficiency as traditional combined pill such as Yasmine®, but with less side-effects, for example, on the cardiovascular system.

Example 6

Another Example Composition According to the Invention

Tablets comprising 4 mg of drospirenone (C-4 mg) are prepared by direct compression. The composition of tablets is described hereunder.

TABLE 7

Composition of tablets (C-4 mg, inventive)

| Material | mg/tablet |
|---|---|
| Drospirenone (PR 100311) | 4.00 |
| Microcrystalline cellulose PH102 | 33.02 |
| Anhydrous lactose PS = 20%, < 45 μm | 17.50 |
| Silicon dioxide | 0.29 |
| Magnesium stearate | 0,33 |
| Coating (Opadry II 85F18422 white) | 1.65 |
| TOTAL | 56.75 |

DRSP batch PR100311 is characterized by a specific area of 0.66 m²/g. The in vitro dissolution rate and the pharmacokinetic parameters for these tablets were determined as described in Example 2 and Example 3, respectively.

TABLE 8

In vitro DRSP dissolution rate and DRSP pharmacokinetic profile for tablets C-4 mg

| In vitro Dissolution | % of DRSP dissolved within 30 min | 45.8 |
|---|---|---|
| | % of DRSP dissolved within 4h | 88.3 |
| Pharmacokinetics | Mean Cmax (ng/ml) | 26 |
| | Mean $t_{max}$ (h) | 3.6 |
| | Mean $AUC_{0-tlast}$ (ng*h/mL) | 643 |

Exemplary Embodiments

The following embodiments are included within the scope of the disclosure:

Embodiment 1. A pharmaceutical composition comprising an active contraceptive drug, wherein said pharmaceutical composition allows for a 28 day daily dosing regimen, and wherein after initial administration of said active contraceptive drug has established its contraceptive effect in a patient, said patient may skip up to 4 doses within any 28 day daily dosing regimen period.

Embodiment 2. The pharmaceutical composition of embodiment 1, wherein said pharmaceutical composition further allows during said 28 day daily dosing regimen for said patient to skip up to two non-consecutive days of said active contraceptive drug, provided said active contraceptive drug skipped dose is taken within about 24 hrs after said up to two skipped non-consecutive days.

Embodiment 3. The pharmaceutical composition of embodiment 1, wherein said skipped up to 4 doses are on non-consecutive days.

Embodiment 4. The pharmaceutical composition of embodiment 1, wherein said skipped up to 4 doses are on consecutive days.

Embodiment 5. The pharmaceutical composition of embodiment 1, wherein said active contraceptive drug inhibits ovulation.

Embodiment 6. The pharmaceutical composition of embodiment 1, wherein said contraceptive effect comprises inhibiting ovulation.

Embodiment 7. The pharmaceutical composition of embodiment 1, wherein said active contraceptive drug is a progestogen-only contraceptive (POC).

Embodiment 8. The pharmaceutical composition of embodiment 7, wherein said POC is selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest.

Embodiment 9. The pharmaceutical composition of embodiment 8, wherein said POC is drospirenone.

Embodiment 10. The pharmaceutical composition of embodiment 9, wherein each daily dose of drospirenone comprises a dosage amount of at least about 2 mg.

Embodiment 11. The pharmaceutical composition of embodiment 1, wherein each daily dose of said active contraceptive drug, when orally administered to a patient in fasting conditions, provides a pharmacokinetic profile for said active contraceptive drug having:
 i) a $T_{max}$ ranging from about 2.2 hrs to 6 hrs; and
 ii) a mean $C_{max}$ which is less than about 30 ng/ml.

Embodiment 12. The pharmaceutical composition of embodiment 11, wherein said pharmacokinetic profile for said active contraceptive drug additionally comprises an $AUC_{0\ h\text{-}tlast}$, which is at least 300 ng·h/ml.

Embodiment 13. The pharmaceutical composition of embodiment 12, wherein said $AUC_{0\ h\text{-}tlast}$ is at least 350 ng·h/ml.

Embodiment 14. The pharmaceutical composition of embodiment 11, wherein the mean $C_{max}$ ranges from about 15 ng/ml to about 30 ng/ml.

Embodiment 15. The pharmaceutical composition of any one of embodiments 10-14, wherein said active contraceptive drug comprises a progestogen-only contraceptive (POC).

Embodiment 16. The pharmaceutical composition of any one of embodiments 10-14, wherein said active contraceptive drug comprises drospirenone.

Embodiment 17. The pharmaceutical composition of embodiment 9, wherein said patient is a women and has one or more conditions or characteristics selected from the group consisting of being predisposed to hyperkalemia, suffering from kidney, liver or adrenal diseases, and being on daily, long-term treatment for a chronic condition with medications predisposed to hyperkalemia.

Embodiment 18. The pharmaceutical composition of embodiment 17, wherein said medications predisposed to hyperkalemia are selected from one or more of the group consisting of a non-steroidal anti-inflammatory, potassium-sparing diuretics, potassium supplementation medication, angiotensin-converting enzyme (ACE) inhibitors, angiotensin-II receptor antagonists and heparin.

Embodiment 19. The pharmaceutical composition of embodiment 9, wherein said patient is in need to improve tolerance for said drospirenone.

Embodiment 20. The pharmaceutical composition of embodiment 19, wherein said patient is preparing for Hormone Replacement Therapy medicaments.

Embodiment 21. The pharmaceutical composition of embodiment 9, wherein said patient has a higher risk for developing a complication from the administration of an estrogen than the general population.

Embodiment 22. The pharmaceutical composition of embodiment 21, wherein said complication from the administration of an estrogen is due to said patient having one or more conditions or characteristics selected from the group consisting of a higher risk for developing thromboembolism than the general Population, acquired or genetic thrombophilia or hypercoagulability, an age of 35 years or over who smoke cigarettes, a higher risk for stroke than the general Population, sickle-cell disease or sickle-cell anemia, a higher risk than the general Population for myocardial infarction, and women currently lactating.

Embodiment 23. A method comprising administering a composition comprising an active contraceptive drug, wherein said pharmaceutical composition allows for a 28 day daily dosing regimen, and wherein after initial administration of said active contraceptive drug has established its contraceptive effect in a patient, said patient may skip up to 4 doses within any 28 day daily dosing regimen period.

Embodiment 24. The method of embodiment 23, wherein said pharmaceutical composition further allows during said 28 day daily dosing regimen for said patient to skip up to two non-consecutive days of said active contraceptive drug, provided said active contraceptive drug skipped dose is taken within about 24 hrs after said up to two skipped non-consecutive days.

Embodiment 25. The method of embodiment 23, wherein said skipped up to 4 doses are on non-consecutive days.

Embodiment 26. The method of embodiment 23, wherein said skipped up to 4 doses are on consecutive days.

Embodiment 27. The method of embodiment 23, wherein said active contraceptive drug inhibits ovulation.

Embodiment 28. The method of embodiment 23, wherein said contraceptive effect comprises inhibiting ovulation.

Embodiment 29. The method of embodiment 23, wherein said active contraceptive drug is a progestogen-only contraceptive (POC).

Embodiment 30. The method of embodiment 29, wherein said POC is selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest.

Embodiment 31. The method of embodiment 30, wherein said POC is drospirenone.

Embodiment 32. The method of embodiment 31, wherein each daily dose of drospirenone comprises a dosage amount of at least about 2 mg.

Embodiment 33. The method of embodiment 23, wherein each daily dose of said active contraceptive drug, when orally administered to a patient in fasting conditions, provides a pharmacokinetic profile for said active contraceptive drug having:
  i) a $T_{max}$ ranging from about 2.2 hrs to 6 hrs; and
  ii) a mean $C_{max}$ which is less than about 30 ng/ml.

Embodiment 34. The method of embodiment 33, wherein said pharmacokinetic profile additionally comprises an $AUC_{0\ h\text{-}tlast}$ which is at least 300 ng·h/ml.

Embodiment 35. The method of embodiment 34, wherein said $AUC_{0\ h\text{-}tlast}$ is at least 350 ng·h/ml.

Embodiment 36. The method of embodiment 33, wherein said mean $C_{max}$ ranges from about 15 ng/ml to about 30 ng/ml.

Embodiment 37. The method of any one of embodiments 33-36, wherein said active contraceptive drug comprises a progestogen-only contraceptive (POC).

Embodiment 38. The method of any one of embodiments 33-36, wherein said active contraceptive drug comprises drospirenone.

Embodiment 39. The method of embodiment 31, wherein said patient is a woman and has one or more conditions or characteristics selected from the group consisting of being predisposed to hyperkalemia, suffering from kidney, liver or adrenal diseases, and being on daily, long-term treatment for a chronic condition with medications predisposed to hyperkalemia.

Embodiment 40. The method of embodiment 39, wherein said medications predisposed to hyperkalemia are selected from one or more of the group consisting of a non steroidal anti-inflammatory, potassium-sparing diuretics, potassium supplementation medication, angiotensin-converting enzyme (ACE) inhibitors, angiotensin-II receptor antagonists and heparin.

Embodiment 41. The method of embodiment 31, wherein said patient is in need to improve tolerance for said drospirenone.

Embodiment 42. The method of embodiment 41, wherein the patient is preparing for Hormone Replacement Therapy medicaments.

Embodiment 43. The method of embodiment 31, wherein said patient has a higher risk for developing a complication from the administration of an estrogen than the general population.

Embodiment 44. The method of embodiment 43, wherein said complication from the administration of an estrogen is due to said patient having one or more conditions or characteristics selected from the group consisting of a higher risk for developing thromboembolism than the general population, acquired or genetic thrombophilia or hypercoagulability, an age of 35 years or over who smoke cigarettes, a higher risk for stroke than the general Population, sickle-cell disease or sickle-cell anemia, a higher risk than the general population for myocardial infarction, and women currently lactating.

Embodiment 45. A kit comprising one or more packaging units wherein each packaging unit comprises up to 28 daily active dosage units comprising an active contraceptive drug in a pharmaceutical composition, wherein said pharmaceutical composition allows for a 28 day daily dosing regimen, and wherein after initial administration of said active contraceptive drug has established its contraceptive effect in a patient, said patient may skip up to 4 doses within any 28 day daily dosing regimen period.

Embodiment 46. The kit of embodiment 45, wherein said pharmaceutical composition further allows during said 28 day daily dosing regimen for said patient to skip up to two non-consecutive days of said active contraceptive drug, provided said active contraceptive drug skipped dose is taken within about 24 hrs after said up to two skipped non-consecutive days.

Embodiment 47. The kit of embodiment 45, wherein said skipped up to 4 doses are on non-consecutive days.

Embodiment 48. The kit of embodiment 45, wherein said skipped up to 4 doses are on consecutive days.

Embodiment 49. The kit of embodiment 45, wherein said active contraceptive drug inhibits ovulation.

Embodiment 50. The kit of embodiment 45, wherein said contraceptive effect comprises inhibiting ovulation.

Embodiment 51. The kit of embodiment 46, wherein said active contraceptive drug is a progestogen-only contraceptive (POC).

Embodiment 52. The kit of embodiment 51, wherein said POC is selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest.

Embodiment 53. The kit of embodiment 52, wherein said POC is drospirenone. Embodiment 54. The kit of embodiment 53, wherein each daily dose of drospirenone comprises a dosage amount of at least about 2 mg.

Embodiment 55. The kit of embodiment 45, wherein each daily dose of said active contraceptive drug, when orally administered to a patient in fasting conditions, provides a pharmacokinetic profile for said active contraceptive drug having:
  i) a $T_{max}$ ranging from about 2.2 hrs to 6 hrs; and
  ii) a mean $C_{max}$ which is less than about 30 ng/ml.

Embodiment 56. The kit of embodiment 55, wherein said pharmacokinetic profile additionally comprises an $AUC_{0\ h\text{-}tlast}$ which is at least 300 ng·h/ml.

Embodiment 57. The kit of embodiment 56, wherein said $AUC_{0\ h\text{-}tlast}$ is at least 350 ng·h/ml.

Embodiment 58. The kit of embodiment 55, wherein said mean $C_{max}$ ranges from about 15 ng/ml to about 30 ng/ml.

Embodiment 59. The kit of any one of embodiments 55-58, wherein said active contraceptive drug comprises a progestogen-only contraceptive (POC).

Embodiment 60. The kit of any one of embodiments 55-58, wherein said active contraceptive drug comprises drospirenone.

Embodiment 61. The kit of embodiment 53, wherein said patient is a woman and has one or more conditions or characteristics selected from the group consisting of being predisposed to hyperkalemia, suffering from kidney, liver or adrenal diseases, and being on daily, long-term treatment for a chronic condition with medications predisposed to hyperkalemia.

Embodiment 62. The kit of embodiment 61, wherein said medications predisposed to hyperkalemia are selected from one or more of the group consisting of a non steroidal anti-inflammatory, potassium-sparing diuretics, potassium supplementation medication, angiotensin-converting enzyme (ACE) inhibitors, angiotensin-II receptor antagonists and heparin.

Embodiment 63. The kit of embodiment 53, wherein said patient is in need to improve tolerance for said drospirenone.

Embodiment 64. The kit of embodiment 63, wherein the patient is preparing for Hormone Replacement Therapy medicaments.

Embodiment 65. The kit of embodiment 53, wherein said patient has a higher risk for developing a complication from the administration of an estrogen than the general population.

Embodiment 66. The kit of embodiment 65, wherein said complication from the administration of an estrogen is due to said patient having one or more conditions or characteristics selected from the group consisting of a higher risk for developing thromboembolism than the general population, acquired or genetic thrombophilia or hypercoagulability, an age of 35 years or over who smoke cigarettes, a higher risk for stroke than the general population, sickle-cell disease or sickle-cell anemia, a higher risk than the general population for myocardial infarction, and women currently lactating.

Embodiment 67. A method comprising producing a pharmacokinetic profile of an active drug in a patient, wherein said pharmacokinetic profile comprises a mean $T_{max}$ ranging from about 2.2 hrs to about 6 hrs, and a mean $C_{max}$ which is less than about 30 ng/ml, wherein said pharmacokinetic profile is measured in said patient after orally administering a single daily dosage unit of said active drug to said patient in fasting conditions.

Embodiment 68. The method of embodiment 67, wherein said pharmacokinetic profile additionally comprises an $AUC_{0\ h\text{-}tlast}$ which is at least 300 ng·h/ml. Embodiment 69. The method of embodiment 68, wherein said $AUC_{0\ h\text{-}tlast}$ is at least 350 ng·h/ml.

Embodiment 70. The method of embodiment 67, wherein said active drug is an active contraceptive drug.

Embodiment 71. The method of embodiment 70, wherein said active contraceptive drug inhibits ovulation.

Embodiment 72. The method of embodiment 70, wherein said active contraceptive drug is a progestogen-only contraceptive (POC).

Embodiment 73. The method of embodiment 72, wherein said POC is selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest.

Embodiment 74. The method of embodiment 73, wherein said POC is drospirenone.

Embodiment 75. The method of embodiment 74, wherein said drospirenone is the only administered active contraceptive drug.

Embodiment 76. The method of embodiment 75, wherein said patient is a woman and has one or more conditions or characteristics selected from the group consisting of being predisposed to hyperkalemia, suffering from kidney, liver or adrenal diseases, and being on daily, long-term treatment for a chronic condition with medications predisposed to hyperkalemia.

Embodiment 77. The method of embodiment 76, wherein said medications predisposed to hyperkalemia are selected from one or more of the group consisting of a non steroidal anti-inflammatory, potassium-sparing diuretics, potassium supplementation medication, angiotensin-converting enzyme (ACE) inhibitors, angiotensin-II receptor antagonists and heparin.

Embodiment 78. The method of embodiment 75, wherein said patient is in need to improve tolerance for said drospirenone.

Embodiment 79. The method of embodiment 78, wherein the patient is preparing for Hormone Replacement Therapy medicaments.

Embodiment 80. The method of embodiment 75, wherein said patient has a higher risk for developing a complication from the administration of an estrogen than the general population.

Embodiment 81. The method of embodiment 80, wherein said complication from the administration of an estrogen is due to said patient having one or more conditions or characteristics selected from the group consisting of a higher risk for developing thromboembolism than the general population, acquired or genetic thrombophilia or hypercoagulability, an age of 35 years or over who smoke cigarettes, a higher risk for stroke than the general population, sickle-cell disease or sickle-cell anemia, a higher risk than the general population for myocardial infarction, and women currently lactating.

Embodiment 82. A pharmaceutical composition comprising an active drug, wherein a single daily dosage unit of said composition, when orally administered to a patient in fasting conditions provides a pharmacokinetic profile for said active drug having:
  i) a $T_{max}$ ranging from about 2.2 hrs to 6 hrs; and
  ii) a mean $C_{max}$ which is less than about 30 ng/ml;

Embodiment 83. The pharmaceutical composition of embodiment 82, wherein said pharmacokinetic profile additionally comprises an $AUC_{0\ h\text{-}tlast}$ which is at least 300 ng·h/ml.

Embodiment 84. The pharmaceutical composition of embodiment 83, said $AUC_{0\ h\text{-}tlast}$ is at least 350 ng·h/ml.

Embodiment 85. The pharmaceutical composition of embodiment 82, wherein said active drug is an active contraceptive drug.

Embodiment 86. The pharmaceutical composition of embodiment 85, wherein said active contraceptive drug inhibits ovulation.

Embodiment 87. The pharmaceutical composition of embodiment 85, wherein said active contraceptive drug is a progestogen-only contraceptive (POC).

Embodiment 88. The pharmaceutical composition of embodiment 87, wherein said POC is selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest.

Embodiment 89. The pharmaceutical composition of embodiment 88, wherein said POC is drospirenone.

Embodiment 90. The pharmaceutical composition of embodiment 89, wherein said patient is a woman and has one or more conditions or characteristics selected from the group consisting of being predisposed to hyperkalemia, suffering from kidney, liver or adrenal diseases, and being on daily, long-term treatment for a chronic condition with medications predisposed to hyperkalemia.

Embodiment 91. The pharmaceutical composition of embodiment 90, wherein said medications predisposed to hyperkalemia are selected from one or more of the group consisting of a non steroidal anti-inflammatory, potassium-sparing diuretics, potassium supplementation medication, angiotensin-converting enzyme (ACE) inhibitors, angiotensin-II receptor antagonists and heparin.

Embodiment 92. The pharmaceutical composition of embodiment 89, wherein said patient is in need to improve tolerance for said drospirenone.

Embodiment 93. The pharmaceutical composition of embodiment 92, wherein the patient is preparing for Hormone Replacement Therapy medicaments.

Embodiment 94. The pharmaceutical composition of embodiment 89, wherein said patient has a higher risk for developing a complication from the administration of an estrogen than the general population.

Embodiment 95. The pharmaceutical composition of embodiment 94, wherein said complication from the administration of an estrogen is due to said patient having one or more conditions or characteristics selected from the group consisting of a higher risk for developing thromboembolism than the general population, acquired or genetic thrombophilia or hypercoagulability, an age of 35 years or over who smoke cigarettes, a higher risk for stroke than the general population, sickle-cell disease or sickle-cell anemia, a higher risk than the general population for myocardial infarction, and women currently lactating.

Embodiment 96. The pharmaceutical composition of embodiment 89, wherein each daily dosage unit of drospirenone comprises a dosage amount of at least about 2 mg.

Embodiment 97. A pharmaceutical composition comprising an active drug, wherein:
  (a) a daily active oral dosage unit of said composition comprises an amount of said active drug of at least 2 mg, and
  (b) the said daily active oral dosage unit comprises said active drug in a form such that when subjected to an in vitro dissolution test according to the USP XXIII Paddle Method:
    (iii) no more than 50% of said active drug initially present in the said daily active dosage unit is dissolved within 30 minutes, and
    (iv) at least 50% of the said active drug is dissolved in a time range from 3 hours to 4 hours.

Embodiment 98. The pharmaceutical composition of embodiment 97, wherein said active drug is an active contraceptive drug.

Embodiment 99. The pharmaceutical composition of embodiment 98, wherein said active contraceptive drug is a progestogen-only contraceptive (POC).

Embodiment 100. The pharmaceutical composition of embodiment 99, wherein said POC is selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest.

Embodiment 101. The pharmaceutical composition of embodiment 100, wherein said POC is drospirenone.

Embodiment 102. The pharmaceutical composition of embodiment 101, wherein each daily dosage unit of drospirenone comprises a dosage amount of at least about 2.0 mg to about 6.0 mg.

Embodiment 103. The pharmaceutical composition of embodiment 102, wherein each daily dosage unit of drospirenone comprises a dosage amount of at least about 3.0 mg to about 4.5 mg.

Embodiment 104. A kit comprising one or more packaging units wherein each packaging unit comprises 21 to 28 daily active dosage units comprising an active drug and
wherein a single active dosage unit, when orally administered under fasting conditions, is adapted to provide a pharmacokinetic profile for said active drug having:
  i) a $T_{max}$ ranging from about 2.2 hrs to 6 hrs; and
  ii) a mean $C_{max}$ which is less than about 30 ng/ml.

Embodiment 105. The kit of embodiment 104, wherein said pharmacokinetic profile additionally comprises an $AUC_{0\ h\text{-}tlast}$ which is at least 300 ng·h/ml.

Embodiment 106. The kit of embodiment 105, wherein said $AUC_{0\ h\text{-}tlast}$ is at least 350 ng·h/ml.

Embodiment 107. The kit of embodiment 104, wherein said mean $C_{max}$ ranges from about 15 ng/ml to about 30 ng/ml.

Embodiment 108. The kit of embodiment 104, wherein said active drug is an active contraceptive drug.

Embodiment 109. The kit of embodiment 108, wherein said active contraceptive drug is a progestogen-only contraceptive (POC).

Embodiment 110. The kit of embodiment 109, wherein said POC is selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest.

Embodiment 111. The kit of embodiment 110, wherein said POC is drospirenone.

Embodiment 112. The kit of embodiment 111, wherein said patient is a woman and has one or more conditions or characteristics selected from the group consisting of being predisposed to hyperkalemia, suffering from kidney, liver or adrenal diseases, and being on daily, long-term treatment for a chronic condition with medications predisposed to hyperkalemia.

Embodiment 113. The kit of embodiment 112, wherein said medications predisposed to hyperkalemia are selected from one or more of the group consisting of a non steroidal anti-inflammatory, potassium-sparing diuretics, potassium supplementation medication, angiotensin-converting enzyme (ACE) inhibitors, angiotensin-II receptor antagonists and heparin.

Embodiment 114. The kit of embodiment 111, wherein said patient is in need to improve tolerance for said drospirenone.

Embodiment 115. The kit of embodiment 114, wherein the patient is preparing for Hormone Replacement Therapy medicaments.

Embodiment 116. The kit of embodiment 111, wherein said patient has a higher risk for developing a complication from the administration of an estrogen than the general population.

Embodiment 117. The kit of embodiment 116, wherein said complication from the administration of an estrogen is due to said patient having one or more conditions or characteristics selected from the group consisting of a higher risk for developing thromboembolism than the general population, acquired or genetic thrombophilia or hypercoagulability, an age of 35 years or over who smoke cigarettes, a higher risk for stroke than the general population, sickle-cell disease or sickle-cell anemia, a higher risk than the general population for myocardial infarction, and women currently lactating.

Embodiment 118. The kit embodiment 111, wherein each daily dosage unit of drospirenone comprises a dosage amount of at least about 2 mg.

Embodiment 119. The kit of embodiment 118, wherein the amount of drospirenone in each daily active unit dosage ranges from about 2.0 mg to about 6.0 mg.

Embodiment 120. The kit of embodiment 119, wherein the amount of drospirenone in each daily active unit dosage ranges from about 3.0 mg to about 4.5 mg.

Embodiment 121. A contraceptive kit comprising one or more packaging units wherein each packaging unit comprises 21 to 28 daily active dosage units and wherein
  (a) each daily active dosage unit comprises at least about 2 mg drospirenone without estrogen, and
  (b) each daily active dosage unit comprises said drospirenone in a form such that when subjected to an in vitro dissolution test according to the USP XXIII Paddle Method:
  (i) no more than about 50% of the drospirenone initially present in the said daily active dosage unit is dissolved within 30 minutes and (ii) at least about 50% of the drospirenone is dissolved in a time range from 3 hours to 4 hours.

Embodiment 122. The kit of embodiment 121, wherein said drospirenone is the sole contraceptive ingredient.

Embodiment 123. The kit of embodiment 122, wherein the amount of drospirenone in each daily active unit dosage ranges from about 2.0 mg to about 6.0 mg.

Embodiment 124. The kit of embodiment 123, wherein the amount of drospirenone in each daily active unit dosage ranges from about 3.0 mg to about 4.5 mg.

Embodiment 125. A pharmaceutical composition comprising a progestogen-only contraceptive (POC) wherein said POC has a d50 particle size which ranges from about 10 to about 60

Embodiment 126. The pharmaceutical composition of embodiment 125, wherein said d50 particle size ranges from about 10 μm to about 30 μm.

Embodiment 127. The pharmaceutical composition of embodiment 125, wherein the surface area of said particles may be from about 2000 $cm^2$/g to about 8500 $cm^2$/g.

Embodiment 128. The pharmaceutical composition of embodiment 127, wherein the surface area of said particles may be from one or more selected from the group consisting of about 2000 $cm^2$/g, about 2500 $cm^2$/g, about 3000 $cm^2$/g, about 3500 $cm^2$/g, about 4000 $cm^2$/g, about 4500 $cm^2$/g, about 5000 $cm^2$/g, about 5500 $cm^2$/g, about 6000 $cm^2$/g, about 6100 $cm^2$/g, about 6200 $cm^2$/g, about 6300 $cm^2$/g, about 6400 $cm^2$/g, about 6500 $cm^2$/g, about 6600 $cm^2$/g, about 6700 $cm^2$/g, about 6800 $cm^2$/g, about 6900 $cm^2$/g, about 7000 $cm^2$/g, about 7500 $cm^2$/g, about 8000 $cm^2$/g and about 8500 $cm^2$/g.

Embodiment 129. The pharmaceutical composition of embodiment 125, wherein said POC is selected from one or more of the group consisting of drospirenone, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, norgestrel, d-17α-acetoxy-13β-ethyl-17α-a-ethinyl-gon-4-en-3-one oxime, cyproterone acetate, gestodene, desogestrel, etonorgestrel, norgestimate, norelgestromin, chlormadione and dienogest.

Embodiment 130. The pharmaceutical composition of embodiment 129, wherein said POC is drospirenone.

Embodiment 131. The pharmaceutical composition of embodiment 130, wherein a single daily dosage unit of said composition, when orally administered to a patient in fasting conditions provides a pharmacokinetic profile for said drospirenone having:
  i) a $T_{max}$ ranging from about 2.2 hrs to 6 hrs; and
  ii) a mean $C_{max}$ which is less than about 30 ng/ml.

Embodiment 132. The pharmaceutical composition of embodiment 131, wherein said pharmacokinetic profile additionally comprises an $AUC_{0\ h\text{-}tlast}$ which is at least 300 ng·h/ml.

Embodiment 133. A method comprising:
  (i) sizing drospirenone to a d50 particle size which ranges from about 10 μm to about 60 μm by subjecting said drospirenone to one or mills selected from the group consisting of a ball mill, a hammer mill, a fluid energy mill, a rod mill, a cutting mill and an oscillating granulator.

Embodiment 134. The method of embodiment 133, further comprising the step of subjecting drospirenone to a vibrating sieve.

Embodiment 135. A method comprising: sizing drospirenone to a d50 particle size which ranges from about 10 μm to about 60 μm by:
  (i) dissolving drospirenone in a water-miscible solvent; and
  (ii) dispersing the resulting solution in cold water under stirring so that to induce the precipitation of drospirenone.

Embodiment 136. The method of embodiment 135, further comprising the step of subjecting drospirenone to a vibrating sieve.

Embodiment 137. The method of embodiment 135, wherein said water-miscible solvent is selected from one or more of the group consisting of methanol, ethanol, isopropanol, dimethylformamide, tetrahydrofuran, dioxane or dimethyl sulfoxide, dimethylacetamide and acetone.

Embodiment 138. The method of embodiment 137, wherein said water-miscible solvent is dimethylacetamide.

Embodiment 139. A pharmaceutical composition comprising a progestogen-only contraceptive (POC), wherein said pharmaceutical composition allows for a 28 day daily dosing regimen, and wherein after initial administration of said POC has inhibited ovulation in a patient, said patient may skip up to 4 doses within any 28 day daily dosing regimen period.

Embodiment 140. The pharmaceutical composition of embodiment 139, wherein said pharmaceutical composition further allows during said 28 day daily dosing regimen for said patient to skip up to two non-consecutive days of said POC, provided said POC skipped dose is taken within about 24 hrs after said up to two skipped non-consecutive days.

Embodiment 141. The pharmaceutical composition of embodiment 139, wherein said skipped up to 4 doses are on non-consecutive days.

Embodiment 142. The pharmaceutical composition of embodiment 139, wherein said skipped up to 4 doses are on consecutive days.

Embodiment 143. The pharmaceutical composition of embodiment 139, wherein said POC inhibits ovulation.

Embodiment 144. A pharmaceutical composition comprising drospirenone for inhibiting ovulation, wherein said pharmaceutical composition allows for a 28 day daily dosing regimen, and wherein after initial administration of said drospirenone has established its contraceptive effect in a patient, said patient may skip up to 4 doses within any 28 day daily dosing regimen period.

Embodiment 145. The pharmaceutical composition of embodiment 144, wherein said drospirenone inhibits ovulation.

Embodiment 146. The pharmaceutical composition of embodiment 144, wherein said pharmaceutical composition further allows during said 28 day daily dosing regimen for said patient to skip up to two non-consecutive days of said drospirenone, provided said drospirenone skipped dose is taken within about 24 hrs after said up to two skipped non-consecutive days.

Embodiment 147. The pharmaceutical composition of embodiment 144, wherein said skipped up to 4 doses are on non-consecutive days.

Embodiment 148. The pharmaceutical composition of embodiment 144, wherein said skipped up to 4 doses are on consecutive days.

Embodiment 149. A method comprising administering a composition comprising a progestogen-only contraceptive (POC), wherein said pharmaceutical composition allows for a 28 day daily dosing regimen, and wherein after initial administration of said POC has established its contraceptive effect in a patient, said patient may skip up to 4 doses within any 28 day daily dosing regimen period.

Embodiment 150. The method of embodiment 149, wherein said pharmaceutical composition further allows during said 28 day daily dosing regimen for said patient to skip up to two non-consecutive days of said POC, provided said POC skipped dose is taken within about 24 hrs after said up to two skipped non-consecutive days.

Embodiment 151. The method of embodiment 149, wherein said skipped up to 4 doses are on non-consecutive days.

Embodiment 152. The method of embodiment 149, wherein said skipped up to 4 doses are on consecutive days.

Embodiment 153. The method of embodiment 149, wherein said POC inhibits ovulation.

Embodiment 154. A method comprising administering a pharmaceutical composition comprising drospirenone to a patient, wherein said pharmaceutical composition allows for a 28 day daily dosing regimen, and wherein after initial administration of said drospirenone has established its contraceptive effect in a patient, said patient may skip up to 4 doses within any 28 day daily dosing regimen period.

Embodiment 155. The method of embodiment 154, wherein said pharmaceutical composition further allows during said 28 day daily dosing regimen for said patient to skip up to two non-consecutive days of said drospirenone, provided said drospirenone skipped dose is taken within about 24 hrs after said up to two skipped non-consecutive days. Embodiment 156. The method of embodiment 154, wherein said skipped up to 4 doses are on non-consecutive days.

Embodiment 157. The method of embodiment 154, wherein said skipped up to 4 doses are on consecutive days.

Embodiment 158. The method of embodiment 154, wherein said drospirenone inhibits ovulation.

Embodiment 159. A kit comprising one or more packaging units wherein each packaging unit comprises up to 28 daily active dosage units comprising a progestogen-only contraceptive (POC) in a pharmaceutical composition, wherein said pharmaceutical composition allows for a 28 day daily dosing regimen, and wherein after initial administration of said POC has established its contraceptive effect in a patient, said patient may skip up to 4 doses within any 28 day daily dosing regimen period.

Embodiment 160. The kit of embodiment 159, wherein said pharmaceutical composition further allows during said 28 day daily dosing regimen for said patient to skip up to two non-consecutive days of said POC, provided said POC skipped dose is taken within about 24 hrs after said up to two skipped non-consecutive days.

Embodiment 161. The kit of embodiment 159, wherein said skipped up to 4 doses are on non-consecutive days.

Embodiment 162. The kit of embodiment 159, wherein said skipped up to 4 doses are on consecutive days.

Embodiment 163. The kit of embodiment 159, wherein said POC inhibits ovulation.

Embodiment 164. A kit comprising one or more packaging units wherein each packaging unit comprises up to 28 daily active dosage units comprising drospirenone in a pharmaceutical composition, wherein said pharmaceutical composition allows for a 28 day daily dosing regimen, and wherein after initial administration of said drospirenone has established its contraceptive effect in a patient, said patient may skip up to 4 doses within any 28 day daily dosing regimen period.

Embodiment 165. The kit of embodiment 164, wherein said pharmaceutical composition further allows during said 28 day daily dosing regimen for said patient to skip up to two non-consecutive days of said drospirenone, provided said drospirenone skipped dose is taken within about 24 hrs after said up to two skipped non-consecutive days.

Embodiment 166. The kit of embodiment 164, wherein said skipped up to 4 doses are on non-consecutive days.

Embodiment 167. The kit of embodiment 164, wherein said skipped up to 4 doses are on consecutive days.

Embodiment 168. The kit of embodiment 164, wherein said drospirenone inhibits ovulation.

What is claimed is:

1. A pharmaceutical composition comprising:
   particles comprising 6β,7β:15β,16β-Dimethylene-3-oxo-17α-pregn-4-ene-21,17-carbolactone having a diameter less than 10 micrometers (μm); and
   one or more pharmaceutically acceptable excipients,
   wherein the pharmaceutical composition does not comprise estrogen; and
   wherein the pharmaceutical composition is formulated such that:
   (1) when orally administered to a patient under fasting conditions, the pharmaceutical composition provides a pharmacokinetic profile for the 6β,7β:15β,16β-Dimethylene-3-oxo-17α-pregn-4-ene-21,17-carbolactone comprising:
     (i) a mean $T_{max}$ ranging from 2.2 hours to 6 hours; and
     (ii) a mean $C_{max}$ of less than 30 ng/ml; and
   (2) no more than 50% of the 6β,7β:15β,16β-Dimethylene-3-oxo-17α-pregn-4-ene-21,17-carbolactone initially present in the pharmaceutical composition is dissolved within 30 minutes if subjected to an in vitro dissolution test according to the USP XXIII Paddle Method.

2. The pharmaceutical composition of claim 1, wherein the one or more pharmaceutically acceptable excipients comprises a filler.

3. The pharmaceutical composition of claim 2, wherein the filler comprises lactose anhydrous, microcrystalline cellulose, starch, pregelatinized starch, modified starch, dibasic calcium phosphate dihydrate, calcium sulfate trihydrate, calcium sulfate dihydrate, calcium carbonate, lactose, dextrose, sucrose, mannitol, sorbitol, or a combination thereof.

4. The pharmaceutical composition of claim 1, wherein the one or more pharmaceutically acceptable excipients comprises a lubricant.

5. The pharmaceutical composition of claim 4, wherein the lubricant comprises magnesium stearate, calcium stearate, zinc stearate, talc, propylene glycol, PEG, stearic acid, vegetable oil, sodium benzoate, sodium lauryl sulfate, magnesium lauryl sulfate, mineral oil polyoxyethylene monostearate, or a combination thereof.

6. The pharmaceutical composition of claim 1, wherein the one or more pharmaceutically acceptable excipients comprises a binder.

7. The pharmaceutical composition of claim 6, wherein the binder comprises a starch, a gum, microcrystalline cellulose, hydroxypropyl cellulose, hydroxyethyl cellulose, hydroxypropylmethyl cellulose, polyvinyl pyrrolidone, or a combination thereof.

8. The pharmaceutical composition of claim 7, wherein the starch comprises potato starch, wheat starch, corn starch, or a combination thereof.

9. The pharmaceutical composition of claim 7, wherein the gum comprises gum tragacanth, acacia gum, gelatin, or a combination thereof.

10. The pharmaceutical composition of claim 1, wherein the one or more pharmaceutically acceptable excipients comprises a glidant.

11. The pharmaceutical composition of claim 10, wherein the glidant comprises silicon dioxide, magnesium trisilicate, powdered cellulose, starch, talc, tribasic calcium phosphate, or a combination thereof.

12. The pharmaceutical composition of claim 1, wherein the pharmaceutical composition is formulated as a tablet or a capsule.

13. The pharmaceutical composition of claim 12, wherein the pharmaceutical composition further comprises a coating.

14. The pharmaceutical composition of claim 13, wherein the coating comprises hydroxypropylmethyl cellulose, hydroxypropyl cellulose, ethyl cellulose, or a combination thereof.

15. The pharmaceutical composition of claim 1,
   wherein the pharmaceutical composition is formulated such that at least 50% of the 6β,7β:15β,16β-Dimethylene-3-oxo-17α-pregn-4-ene-21,17-carbolactone initially present in the pharmaceutical composition is dissolved within 4 hours if subjected to the in vitro dissolution test according to the USP XXIII Paddle Method.

16. The pharmaceutical composition of claim 1, wherein the 6β,7β:15β,16β-Dimethylene-3-oxo-17α-pregn-4-ene-21,17-carbolactone is present in an amount ranging from 2 milligrams (mg) to 6 mg.

17. The pharmaceutical composition of claim 16, wherein the amount of the 6β,7β:15β,16β-Dimethylene-3-oxo-17α-pregn-4-ene-21,17-carbolactone present ranges from 3.0 mg to 4.5 mg.

18. The pharmaceutical composition of claim 16, wherein the amount of the 6β,7β:15β,16β-Dimethylene-3-oxo-17α-pregn-4-ene-21,17-carbolactone present is 3.5 mg.

19. The pharmaceutical composition of claim 16, wherein the amount of the 6β,7β:15β,16β-Dimethylene-3-oxo-17α-pregn-4-ene-21,17-carbolactone present is 4.0 mg.

20. The pharmaceutical composition of claim 1, wherein the pharmaceutical composition is formulated such that at least 55% of the 6β,7β:15β,16β-Dimethylene-3-oxo-17α-pregn-4-ene-21,17-carbolactone initially present in the pharmaceutical composition is dissolved within 4 hours if subjected to the in vitro dissolution test according to the USP XXIII Paddle Method.

21. The pharmaceutical composition of claim 1, wherein the pharmacokinetic profile further comprises an $AUC_{0\ h\text{-}tlast}$ of at least 300 ng*h/ml.

22. The pharmaceutical composition of claim 1, wherein the pharmacokinetic profile further comprises an $AUC_{0\ h\text{-}tlast}$ of at least 350 ng*h/ml.

23. The pharmaceutical composition of claim 1, wherein the mean $C_{max}$ ranges from 15 ng/ml to less than 30 ng/ml.

24. The pharmaceutical composition of claim 15, wherein the mean $C_{max}$ ranges from 15 ng/ml to less than 30 ng/ml.

25. The pharmaceutical composition of claim 15, wherein the pharmaceutical composition comprises from 3.0 mg to 4.5 mg of the 6β,7β:15β,16β-Dimethylene-3-oxo-17α-pregn-4-ene-21,17-carbolactone.

26. The pharmaceutical composition of claim 20, wherein the pharmaceutical composition comprises from 3.0 mg to 4.5 mg of the 6β,7β:15β,16β-Dimethylene-3-oxo-17α-pregn-4-ene-21,17-carbolactone.

27. The pharmaceutical composition of claim 21, wherein the pharmaceutical composition comprises from 3.0 mg to 4.5 mg of the 6β,7β:15β,16β-Dimethylene-3-oxo-17α-pregn-4-ene-21,17-carbolactone.

28. The pharmaceutical composition of claim 22, wherein the pharmaceutical composition comprises from 3.0 mg to 4.5 mg of the 6β,7β:15β,16β-Dimethylene-3-oxo-17α-pregn-4-ene-21,17-carbolactone.

29. The pharmaceutical composition of claim 23, wherein the pharmaceutical composition comprises from 3.0 mg to 4.5 mg of the 6β,7β:15β,16β-Dimethylene-3-oxo-17α-pregn-4-ene-21,17-carbolactone.

30. The pharmaceutical composition of claim 24, wherein the pharmaceutical composition comprises from 3.0 mg to 4.5 mg of the 6β,7β:15β,16β-Dimethylene-3-oxo-17α-pregn-4-ene-21,17-carbolactone.

* * * * *